US005766853A

United States Patent [19]
Parma et al.

[11] Patent Number: 5,766,853
[45] Date of Patent: Jun. 16, 1998

[54] METHOD FOR IDENTIFICATION OF HIGH AFFINITY NUCLEIC ACID LIGANDS TO SELECTINS

[75] Inventors: David H. Parma; Brian James Hicke; Larry Gold. all of Boulder, Colo.

[73] Assignee: NeXstar Pharmaceuticals, Inc., Boulder, Colo.

[21] Appl. No.: 472,255

[22] Filed: Jun. 7, 1995

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and a continuation-in-part of Ser. No. 964,624, Oct. 21, 1992, Pat. No. 5,496,938.

[51] Int. Cl.$^6$ .................. C12Q 1/68; G01N 33/53; C07H 19/00; C07H 21/02
[52] U.S. Cl. .................. 435/6; 435/7.1; 536/22.1; 536/23.1; 536/24.33; 536/25.4
[58] Field of Search .................. 435/6, 7.1; 536/22.1, 536/23.1, 24.33, 25.4

[56] References Cited

U.S. PATENT DOCUMENTS

| | | | |
|---|---|---|---|
| 5,270,163 | 12/1993 | Gold et al. | 435/6 |
| 5,459,015 | 10/1995 | Janjic et al. | 435/6 |
| 5,472,841 | 12/1995 | Jayasena et al. | 435/6 |
| 5,475,096 | 12/1995 | Gold et al. | 536/23.1 |
| 5,476,766 | 12/1995 | Gold et al. | 435/6 |
| 5,484,891 | 1/1996 | Lasky et al. | 530/387.3 |
| 5,489,677 | 2/1996 | Sanghvi et al. | 536/22.1 |
| 5,496,938 | 3/1996 | Gold et al. | 536/22.1 |
| 5,503,978 | 4/1996 | Schneider et al. | 435/6 |
| 5,527,894 | 6/1996 | Gold et al. | 536/22.1 |
| 5,543,293 | 8/1996 | Gold et al. | 435/6 |
| 5,567,588 | 10/1996 | Gold et al. | 435/6 |
| 5,580,737 | 12/1996 | Polisky et al. | 435/6 |
| 5,587,468 | 12/1996 | Allen et al. | 536/22.1 |
| 5,595,877 | 1/1997 | Gold et al. | 435/6 |

FOREIGN PATENT DOCUMENTS

| | | | |
|---|---|---|---|
| 2183661 | 6/1987 | United Kingdom. | |
| 8906694 | 7/1989 | WIPO. | |
| WO 92/14843 | 9/1992 | WIPO | C12Q 1/68 |

OTHER PUBLICATIONS

Cassels, et al., (1990) *J. of Biol. Chem.* 265 :14127–14135.
DeFreese, et al., (1993) *J. Am. Chem. Soc.* 115 :7549–7550.
Ellington et al., (1990) Abstract presented at 1990 meeting on RNA Processing, Cold Spring Harbor Laboratory. Cold Spring Harbor, NY. p. 84.
Foxall et al., (1992) *J Cell Biol.* 117 :895–902.
Glick et al., (1991) *J. Biol. Chem.* 266 :23660–23669.
Green et al., (1995) *Glycobiology* 5 :29–38.
Immundo et al., (1995) *Proc. Natl. Acad. Sci.* 92 :3019–3025.
Jacob et al., (1995) *Biochemistry* 34 :1210–1217.
Joyce, Gerald F. (1989) *Gene* 82 :83–87.
Joyce et al., (1989) *Nucl. Acids Res.* 17 :711–722.
Karlsson, Karl-Anders (1989) *Annu.Rev.Biochem.* 58 :309–50.
Kinzler et al., (1989) *Nucl. Acids Res.* 17 :3645–3653.
Kramer et al., (1974) *J.Mol.Biol.* 89 :719–736.
Lee, Y.C. (1992) *FASEB J.* 6 :3139–3200.
Levisohn et al., (1968) *Proc. Natl. Acad. Sci. USA* 60 :866–872.
Levisohn et al., (1969) *Proc. Natl. Acad. Sci. USA* 63 :805.
Lucas et al., (1994) *Science* 263 :814–817.
Ma et al., (1993) *Circ.* 88 :649–658.
Martens et al., (1995) *J. Biol. Chem.* 270 :21129–21136.
Mihelcic et al., (1994) *Blood* 84 :2322–2328.
Monsigny et al., (1979) *J.Biochem.* 98 :39–45.
Mulligan et al., (1993) *Nature* 364 :149–151.
Mulligan et al., (1993) *J. Immun.* 151 :6410–6417.
Mulligan et al., (1993) *J.Exp. Med.* 178 :623–631.
Mulligan et al., (1992) *J. Clin. Invest.* 90 :1600–1607.
Mulligan et al., (1994) *J. Immun.* 832–840.
Nagata et al., (1974) *J. Biol. Chem.* 249:3116–3122.
Nelson et al., (1993) *Amer. Soc. Clin. Inv.* 91 :1157–1166.
Nelson et al., (1994) *J. Biol. Chem.* 269:15060–15066.
Nelson et al., (1993) *Blood* 82 :3235–3258.
Oliphant et al., (1989) *Mol. Cell. Biol.* 9 :2944.
Oliphant et al., (1988) *Nucl. Acids. Res.* 16 :7673.
Oliphant et al., (1987) *Meth. Enzym.* 155 :568.
Oliphant et al., (1986) *Gene* 44 :177.
Orlandi et al., (1992) *J. Cell. Biol.* 116 :901–909.
Petri, William A. Jr. (1991) *ASM News* 57 :299–306.
Phillips et al., (1990) *Science* 250 :1130–1132.
Robertson et al., (1990) *Nature* 344 :467–468.
Seekamp et al., (1991) *Amer. J. Path.* 144 :592–598.
Saitoh et al., (1991) *FEBS* 282 :385–387.
Sherblom et al., (1994) *J. Biol. Chem.* 263 :5418–5424.
Thiesen et al., (1990) *Nucl. Acids Res.* 18 :3203–3209.
Todderud et al., (1992) *J. Leuk. Biol.* 52:85–88.
Tyrrell et al., (1991) *Proc. Natl. Acad. Sci. USA* 88 :10372–10376.
Van Landschoot et al., (1977) *Eur. J.Biochem.* 79 :275–283.
Watowich et al., (1994) *Structure* 2:719–731.
Watson et al., (1991) *Nature* 349:164–166.
Watson et al., (1990) *J. Cell. Biol.* 110:2221–2229.
Winn et al., (1993) *Amer. Soc. Clin. Inv.* 92:2042–2047.
Wright, Christine Schubert and Joachim Jaeger (1993) *J. Mol. Biol.* 232:620–638.
Yednock et al., (1987) *J. Cell. Biol.* 104:713–723.
Yuen et al., (1994) *J. Biol. Chem.* 269:1595–1598.

*Primary Examiner*—Ardin H. Marschel
*Assistant Examiner*—Jezia Riley
*Attorney, Agent, or Firm*—Swanson & Bratschun, LLC

[57] ABSTRACT

This invention discloses high-affinity oligonucleotide ligands to lectins, specifically nucleic acid ligands having the ability to bind to the lectins, wheat germ agglutinin. L-selectin, E-selectin and P-selectin. Also disclosed are the methods for obtaining such ligands.

9 Claims, 10 Drawing Sheets

SEQ ID NO:174

SEQ ID NO:175

SEQ ID NO:176

(SEQ ID NO:67)
FIGURE 7A
(SEQ ID NO:84)
FIGURE 7B
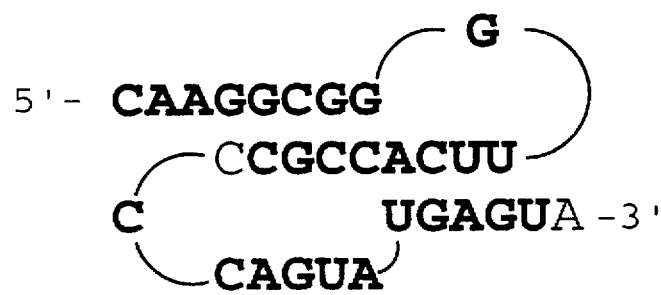
(SEQ ID NO:78)
FIGURE 7C

```
           G  Y                    ssDNA Family 1
        Y        T
        G        A       Co-variation and Secondary Structure
        G        A
        A        A                     Base Pairs
          A    A
          A    C       AT    TA    GC    CG    GT    TG    GA    AG    AA    OTHER
            C-G        --    --    --    22    --    --    --    --    --     --
            A-T        17     3     1     1    --    --    --    --    --     --
            T-A         2    16    --    --     1    --    --    --    --      3
            G A         1     6    --    --     1    --     9     2     2      1
            N-N'        8     4     7    --     1     1    --    --     1     --
            N-N'       --     2     7    10     2    --    --    --    --      1
            N-N'        3    --     2     3     4    --    --    --    --     10
        5'- N-N' -3'   --    --    --    --     1    --    --    --    --     21
```

SEQ ID NO:177

FIGURE 10

SEQUENCE LISTING ( 1 ) GENERAL INFORMATION:

( i i i ) NUMBER OF SEQUENCES: 173

( 2 ) INFORMATION FOR SEQ ID NO:1:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:1:

```
GGGAAAAGCG AAUCAUACAC AAGANNNNNN NNNNNNNNNN NNNNNNNNNN      50
NNNNNNNNNN NNNNNNNNNN NNNNGCUCCG CCAGAGACCA ACCGAGAA         98
```

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:2:

UAAUACGACU CACUAUAGGG AAAAGCGAAU CAUACACAAG A        41

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:3:

UUCUCGGUUG GUCUCUGGCG GAGC        24

( 2 ) INFORMATION FOR SEQ ID NO:4:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:4:

GGGAAAAGCG AAUCAUACAC AAGAAUGGUU GGCCUGGGCG CAGGCUUCGA        50

AGACUCGGCG GGAACGGGAA UGGCUCCGCC AGAGACCAAC CGAGAA        96

( 2 ) INFORMATION FOR SEQ ID NO:5:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:5:

GGGAAAAGCG AAUCAUACAC AAGACAGGCA CUGAAAACUC GGCGGGAACG    50

AAAGUAGUGC CGACUCAGAC GCGUGCUCCG CCAGAGACCA ACCGAGAA    98

( 2 ) INFORMATION FOR SEQ ID NO:6:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:6:

GGGAAAAGCG AAUCAUACAC AAGAAGUCUG GCCAAAGACU CGGCGGGAAC    50

GUAAAACGGC CAGAAUUGCU CCGCCAGAGA CCAACCGAGA A    91

( 2 ) INFORMATION FOR SEQ ID NO:7:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:7:

GGGAAAAGCG AAUCAUACAC AAGAGUAGGA GGUUCCAUCA CCAGGACUCG    50

GCGGGAACGG AAGGUGAUGS GCUCCGCCAG AGACCAACCG AGAA    94

( 2 ) INFORMATION FOR SEQ ID NO:8:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:8:

GGGAAAAGCG AAUCAUACAC AAGAACAAGG AUCGAUGGCG AGCCGGGGAG    50

GGCUCGGCGG GAACGAAAUC UGCUCCGCCA GAGACCAACC GAGAA    95

( 2 ) INFORMATION FOR SEQ ID NO:9:

( i ) SEQUENCE CHARACTERISTICS:

(A) LENGTH: 97 base pairs
(B) TYPE: nucleic acid
(C) STRANDEDNESS: single
(D) TOPOLOGY: linear (i i) MOLECULE TYPE: RNA (i x) FEATURE:
(D) OTHER INFORMATION: All C's are 2'-NH2 cytosine (i x) FEATURE:
(D) OTHER INFORMATION: All U's are 2'-NH2 uracil (x i) SEQUENCE DESCRIPTION: SEQ ID NO:9:

| GGGAAAAGCG | AAUCAUACAC | AAGAUUGGGC | AGGCAGAGCG | AGACCGGGGG | 50 |
| CUCGGCGGGA | ACGGAACAGG | AAUGCUCCGC | CAGAGACCAA | CCGAGAA | 97 |

(2) INFORMATION FOR SEQ ID NO:10:

(i) SEQUENCE CHARACTERISTICS:
(A) LENGTH: 97 base pairs
(B) TYPE: nucleic acid
(C) STRANDEDNESS: single
(D) TOPOLOGY: linear (i i) MOLECULE TYPE: RNA (i x) FEATURE:
(D) OTHER INFORMATION: All C's are 2'-NH2 cytosine (i x) FEATURE:
(D) OTHER INFORMATION: All U's are 2'-NH2 uracil (x i) SEQUENCE DESCRIPTION: SEQ ID NO:10:

| GGGAAAAGCG | AAUCAUACAC | AAGAAAGGGA | UGGGAUUGGG | ACGAGCGGCC | 50 |
| AAGACUCGGC | GGGAACGAAG | GGUGCUCCGC | CAGAGACCAA | CCGAGAA | 97 |

(2) INFORMATION FOR SEQ ID NO:11:

(i) SEQUENCE CHARACTERISTICS:
(A) LENGTH: 96 base pairs
(B) TYPE: nucleic acid
(C) STRANDEDNESS: single
(D) TOPOLOGY: linear (i i) MOLECULE TYPE: RNA (i x) FEATURE:
(D) OTHER INFORMATION: All C's are 2'-NH2 cytosine (i x) FEATURE:
(D) OTHER INFORMATION: All U's are 2'-NH2 uracil (x i) SEQUENCE DESCRIPTION: SEQ ID NO:11:

| GGGAAAAGCG | AAUCAUACAC | AAGACUCGGC | GGGAACGAAA | GUGUCAUGGU | 50 |
| AGCAAGUCCA | AUGGUGGACU | CUGCUCCGCC | AGAGACCAAC | CGAGAA | 96 |

(2) INFORMATION FOR SEQ ID NO:12:

(i) SEQUENCE CHARACTERISTICS:
(A) LENGTH: 98 base pairs
(B) TYPE: nucleic acid
(C) STRANDEDNESS: single
(D) TOPOLOGY: linear (i i) MOLECULE TYPE: RNA (i x) FEATURE:
(D) OTHER INFORMATION: All C's are 2'-NH2 cytosine (i x) FEATURE:

( D ) OTHER INFORMATION: All U's are 2'-NH2 uracil ( x i ) SEQUENCE DESCRIPTION: SEQ ID NO:12:

GGGAAAAGCG AAUCAUACAC AAGACUCGGC GGGAACGUGA AGUGGGUAGG        50

UAGCUGAAGA CGGUCUGGGC GCCAGCUCCG CCAGAGACCA ACCGAGAA         98

( 2 ) INFORMATION FOR SEQ ID NO:13:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:13:

GGGAAAAGCG AAUCAUACAC AAGAAAGGGA UGGGAUUGGG ACGAGCGGCC        50

AAGACUCGGC GGGAACGAAG GGUCCGCUCC GCCAGAGACC AACCGAGAA        99

( 2 ) INFORMATION FOR SEQ ID NO:14:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:14:

GGGAAAAGCG AAUCAUACAC AAGACUCGGC GGGAACGAAG UGUGUGAGUA        50

ACGAUCACUU GGUACUAAAA GCCCGCUCCG CCAGAGACCA ACCGAGAA         98

( 2 ) INFORMATION FOR SEQ ID NO:15:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:15:

GGGAAAAGCG AAUCAUACAC AAGACUCGGC GGGAAUCGAA AGUGUACUGA        50

AUUAGAACGG UGGGCCUGCU CAUCGUGCUC CGCCAGAGAC CAACCGAGAA       100

( 2 ) INFORMATION FOR SEQ ID NO:16:

( i ) SEQUENCE CHARACTERISTICS:
    ( A ) LENGTH: 103 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:16:

| | | | | | |
|---|---|---|---|---|---|
| GGGAAAAGCG | AAUCAUACAC | AAGACUCGGC | GGGAAUCGUA | AUGUGGAUGA | 50 |
| UAGCACGAUG | GCAGYAGUAG | UCGGACCGCG | CUCCGCCAGA | GACCAACCGA | 100 |
| GAA | | | | | 103 |

( 2 ) INFORMATION FOR SEQ ID NO:17:

( i ) SEQUENCE CHARACTERISTICS:
    ( A ) LENGTH: 98 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:17:

| | | | | | |
|---|---|---|---|---|---|
| GGGAAAAGCG | AAUCAUACAC | AAGACAGCGG | CGGAGUCAGU | GAAAGCGUGG | 50 |
| GGGGYGCGGG | AGGUCUACCC | UGACGCUCCG | CCAGAGACCA | ACCGAGAA | 98 |

( 2 ) INFORMATION FOR SEQ ID NO:18:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:18:

| | | | | | |
|---|---|---|---|---|---|
| GGGAAAAGCG | AAUCAUACAC | AAGACGGCUG | UGUGUGGUAG | CGUCAUAGUA | 50 |
| GGAGUCGUCA | CGAACCAAGG | CGCUCCGCCA | GAGACCAACC | GAGAA | 95 |

( 2 ) INFORMATION FOR SEQ ID NO:19:

( i ) SEQUENCE CHARACTERISTICS:
    ( A ) LENGTH: 98 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:

(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:19:

| | | | | | |
|---|---|---|---|---|---|
| GGGAAAAGCG | AAUCAUACAC | AAGACGGCUG | UGUGGUGUUG | GAGCGUCAUA | 50 |
| GUAGGAGUCG | UCACGAACCA | AGGCGCUCCG | CCAGAGACCA | ACCGAGAA | 98 |

(2) INFORMATION FOR SEQ ID NO:20:

(i) SEQUENCE CHARACTERISTICS:
(A) LENGTH: 97 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:20:

| | | | | | |
|---|---|---|---|---|---|
| GGGAAAAGCG | AAUCAUACAC | AAGACGAUGC | GAGGCAAGAA | AUGGAGUCGU | 50 |
| UACGAACCCU | CUUGCAGUGC | GCGGCUCCGC | CAGAGACCAA | CCGAGAA | 97 |

(2) INFORMATION FOR SEQ ID NO:21:

(i) SEQUENCE CHARACTERISTICS:
(A) LENGTH: 95 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:21:

| | | | | | |
|---|---|---|---|---|---|
| GGGAAAAGCG | AAUCAUACAC | AAGACGUGCG | GAGCAAAUAG | GGGAUCAUGG | 50 |
| AGUCGUACGA | ACCGUUAUCG | CGCUCCGCCA | GAGACCAACC | GAGAA | 95 |

(2) INFORMATION FOR SEQ ID NO:22:

(i) SEQUENCE CHARACTERISTICS:
(A) LENGTH: 97 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:22:

| | | | | | |
|---|---|---|---|---|---|
| GGGAAAAGCG | AAUCAUACAC | AAGACUGGGG | AGCAGGAUAU | GAGAUGUGCG | 50 |
| GGGCAAUGGA | GUCGUGACGA | ACCGCUCCGC | CAGAGACCAA | CCGAGAA | 97 |

( 2 ) INFORMATION FOR SEQ ID NO:23:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:23:

```
GGGAAAAGCG   AAUCAUACAC   AAGAGUCCGC   CCCCAGGGAU   GCAACGGGGU        50
GGCUCUAAAA   GGCUUGGCUA   AGCUCCGCCA   GAGACCAACC   GAGAA             95
```

( 2 ) INFORMATION FOR SEQ ID NO:24:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:24:

```
GGGAAAAGCG   AAUCAUACAC   AAGAGAGAAU   GAGCAUGGCC   GGGGCAGGAA        50
GUGGGUGGCA   ACGGAGGCCA   GCUCCGCCAG   AGACCAACCG   AGAA              94
```

( 2 ) INFORMATION FOR SEQ ID NO:25:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:25:

```
GGGAAAAGCG   AAUCAUACAC   AAGAGAUACA   GCGCGGGUCU   AAAGACCUUG        50
CCCCUAGGAU   GCAACGGGGU   GGCUCCGCCA   GAGACCAACC   GAGAA             95
```

( 2 ) INFORMATION FOR SEQ ID NO:26:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:26:

```
GGGAAAAGCG  AAUCAUACAC  AAGAUGAAGG  GUGGUAAGAG  AGAGUCUGAG      50

CUCGUCCUAG  GGAUGCAACG  GCAGCUCCGC  CAGAGACCAA  CCGAGAA         97
```

( 2 ) INFORMATION FOR SEQ ID NO:27:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:27:

```
GGGAAAAGCG  AAUCAUACAC  AAGACAAACC  UGCAGUCGCG  CGGUGAAACC      50

UAGGGUUGCA  ACGGUACAUC  GCUGUGCUCC  GCCAGAGACC  AACCGAGAA       99
```

( 2 ) INFORMATION FOR SEQ ID NO:28:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:28:

```
GGGAAAAGCG  AAUCAUACAC  AAGAGUGGAC  UGGAAUCUUC  GAGGACAGGA      50

ACGUUCCUAG  GGAUGCAACG  GACGCUCCGC  CAGAGACCAA  CCGAGAA         97
```

( 2 ) INFORMATION FOR SEQ ID NO:29:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:29:

```
GGGAAAAGCG  AAUCAUACAC  AAGAGUGUAC  CAAUGGAGGC  AAUGCUGCGG      50

GAAUGGAGGC  CUAGGGAUGC  AACGCUCCGC  CAGAGACCAA  CCGAGAA         97
```

( 2 ) INFORMATION FOR SEQ ID NO:30:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:30:

```
GGGAAAAGCG  AAUCAUACAC  AAGAGUCCCU  AGGGAUGCAA  CGGGCAGCAU    50
UCGCAUAGGA  GUAAUCGGAG  GUCGCUCCGC  CAGAGACCAA  CCGAGAA       97
```

( 2 ) INFORMATION FOR SEQ ID NO:31:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:31:

```
GGGAAAAGCG  AAUCAUACAC  AAGAGCCUAG  GGAUGCAACG  GCGAAUGGAU    50
AGCGAUGUCG  UGGACAGCCA  GGUGCUCCGC  CAGAGACCAA  CCGAGAA       97
```

( 2 ) INFORMATION FOR SEQ ID NO:32:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:32:

```
GGGAAAAGCG  AAUCAUACAC  AAGAAUCGAA  CCUAGGGAUG  CAACGGUGAA    50
GGUUGUGAGG  AUUCGCCAUU  AGGCGCUCCG  CCAGAGACCA  ACCGAGAA      98
```

( 2 ) INFORMATION FOR SEQ ID NO:33:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:33:

| | | | | | |
|---|---|---|---|---|---|
| GGGAAAAGCG | AAUCAUACAC | AAGAGCUAGG | GAUGCCGCAG | AAUGGUCGCG | 50 |
| GAUGUAAUAG | GUGAAGAUUG | UUGCGCUCCG | CCAGAGACCA | ACCGAGAA | 98 |

( 2 ) INFORMATION FOR SEQ ID NO:34:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:34:

| | | | | | |
|---|---|---|---|---|---|
| GGGAAAAGCG | AAUCAUACAC | AAGAGGACCU | AGGGAUGCAA | CGGUCCGACC | 50 |
| UUGAUGCGCG | GGUGUCCAAG | CUACGCUCCG | CCAGAGACCA | ACCGAGAA | 98 |

( 2 ) INFORMATION FOR SEQ ID NO:35:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:35:

| | | | | | |
|---|---|---|---|---|---|
| GGGAAAAGCG | AAUCAUACAC | AAGAAAGGGA | GGAGCUAGAG | AGGGAAAGGU | 50 |
| UACUACGCGC | CAGAAUAGGA | UGUGCUCCGC | CAGAGACCAA | CCGAGAA | 97 |

( 2 ) INFORMATION FOR SEQ ID NO:36:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:36:

| | | | | | |
|---|---|---|---|---|---|
| GGGAAAAGCG | AAUCAUACAC | AAGACCAACG | UACAUCGCGA | GCUGGUGGAG | 50 |

AGUUCAUGAG GGUGUUACGG GGUGCUCCGC CAGAGACCAA CCGAGAA            97

( 2 ) INFORMATION FOR SEQ ID NO:37:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:37:

GGGAAAAGCG AAUCAUACAC AAGACCCAAC GUGUCAUCGC GAGCUGGCGG            50

AGAGUUCAUG AGGGUUACGG GUGCUCCGCC AGAGACCAAC CGAGAA            96

( 2 ) INFORMATION FOR SEQ ID NO:38:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:38:

GGGAAAAGCG AAUCAUACAC AAGAGUUGGU GCGAGCUGGG GCGGCGAGAA            50

GGUAGGCGGU CCGAGUGUUC GAAUGCUCCG CCAGAGACCA ACCGAGAA            98

( 2 ) INFORMATION FOR SEQ ID NO:39:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:39:

GGGAAAAGCG AAUCAUACAC AAGACUGGCA AGRAGUGCGU GAGGGUACGU            50

UAGGGGUGUU UGGGCCGAUC GCAUGCUCCG CCAGAGACCA ACCGAGAA            98

( 2 ) INFORMATION FOR SEQ ID NO:40:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:40:

```
GGGAAAAGCG AAUCAUACAC AAGAUUGGUC GUACUGGACA GAGCCGUGGU        50
AGAGGGAUUG GGACAAAGUG UCAGCUCCGC CAGAGACCAA CCGAGAA           97
```

( 2 ) INFORMATION FOR SEQ ID NO:41:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:41:

```
GGGAAAAGCG AAUCAUACAC AAGAUGUGAG AAAGUGGCCA ACUUUAGGAC        50
GUCGGUGGAC UGYGCGGGUA GGCUCGCUCC GCCAGAGACC AACCGAGAA         99
```

( 2 ) INFORMATION FOR SEQ ID NO:42:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:42:

```
GGGAAAAGCG AAUCAUACAC AAGACAGGCA GAUGUGUCUG AGUUCGUCGG        50
AGUAGACGUC GGUGGACGCG GAACGCUCCG CCAGAGACCA ACCGAGAA          98
```

( 2 ) INFORMATION FOR SEQ ID NO:43:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:43:

```
GGGAAAAGCG AAUCAUACAC AAGAUGUGAU UAGGCAGUUG CAGCCGCCGU        50
```

```
GCGGAGACGU GACUCGAGGA UUCGCUCCGC CAGAGACCAA CCGAGAA          97
```

( 2 ) INFORMATION FOR SEQ ID NO:44:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:44:

```
GGGAAAAGCG AAUCAUACAC AAGAUGCCGG UGGAAAGGCG GGUAGGUGAC          50
CCGAGGAUUC CUACCAAGCC AUGCUCCGCC AGAGACCAAC CGAGAA             96
```

( 2 ) INFORMATION FOR SEQ ID NO:45:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:45:

```
GGGAAAAGCG AAUCAUACAC AAGAGAGGUG RAUGGGAGAG UGGAGCCCGG          50
GUGACUCGAG GAUUCCCGUG CUCCGCCAGA GACCAACCGA GAA                93
```

( 2 ) INFORMATION FOR SEQ ID NO:46:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:46:

```
GGGAAAAGCG AAUCAUACAC AAGAGUCAUG CUGUGGCUGA ACAUACUGGU          50
GAAAGUUCAG UAGGGUGGAU ACAGCUCCGC CAGAGACCAA CCGAGAA            97
```

( 2 ) INFORMATION FOR SEQ ID NO:47:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear (  i  i  ) MOLECULE TYPE: RNA (  i  x  ) FEATURE:
    ( D ) OTHER INFORMATION: All C's are 2'-NH2 cytosine (  i  x  ) FEATURE:
    ( D ) OTHER INFORMATION: All U's are 2'-NH2 uracil (  x  i  ) SEQUENCE DESCRIPTION: SEQ ID NO:47:

| GGGAAAAGCG | AAUCAUACAC | AAGACCGGGG | AUGGUGAGUC | GGGCAGUGUG | 50 |
| ACCGAACUGG | UGCCCGCUGA | GAGCUCCGCC | AGAGACCAAC | CGAGAA | 96 |

( 2 ) INFORMATION FOR SEQ ID NO:48:

( i ) SEQUENCE CHARACTERISTICS:
    ( A ) LENGTH: 97 base pairs
    ( B ) TYPE: nucleic acid
    ( C ) STRANDEDNESS: single
    ( D ) TOPOLOGY: linear (  i  i  ) MOLECULE TYPE: RNA (  i  x  ) FEATURE:
    ( D ) OTHER INFORMATION: All C's are 2'-NH2 cytosine (  i  x  ) FEATURE:
    ( D ) OTHER INFORMATION: All U's are 2'-NH2 uracil (  x  i  ) SEQUENCE DESCRIPTION: SEQ ID NO:48:

| GGGAAAAGCG | AAUCAUACAC | AAGAACACUA | ACCAGGUCUC | UGAACGCGGG | 50 |
| ACGGAGGUGU | GGGCGAGGUG | GAAGCUCCGC | CAGAGACCAA | CCGAGAA | 97 |

( 2 ) INFORMATION FOR SEQ ID NO:49:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear (  i  i  ) MOLECULE TYPE: RNA (  i  x  ) FEATURE:
    ( D ) OTHER INFORMATION: All C's are 2'-NH2 cytosine (  i  x  ) FEATURE:
    ( D ) OTHER INFORMATION: All U's are 2'-NH2 uracil (  x  i  ) SEQUENCE DESCRIPTION: SEQ ID NO:49:

| GGGAAAAGCG | AAUCAUACAC | AAGACCGUCU | CCCGAGAACC | AGGCAGAGGA | 50 |
| CGUGCUGAAG | GAGCUGCAUC | UAGAAGCUCC | GCCAGAGACC | AACCGAGAA | 99 |

( 2 ) INFORMATION FOR SEQ ID NO:50:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear (  i  i  ) MOLECULE TYPE: RNA (  i  x  ) FEATURE:
    ( D ) OTHER INFORMATION: All C's are 2'-NH2 cytosine (  i  x  ) FEATURE:
    ( D ) OTHER INFORMATION: All U's are 2'-NH2 uracil (  x  i  ) SEQUENCE DESCRIPTION: SEQ ID NO:50:

```
GGGAAAAGCG  AAUCAUACAC  AAGACCGUCU  CCGAGAACCA  GGCAGAGGAG         50

GUGCUGAAGG  RGCUGGCAUC  UACAAGCUCC  GCCAGAGACC  AACCGAGAA          99
```

( 2 ) INFORMATION FOR SEQ ID NO:51:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:51:

```
GGGAAAAGCG  AAUCAUACAC  AAGACCCGCA  CAUAAUGUAG  GGAACAAUGU         50

UAUGGCGGAA  UUGAUAACCG  GUGCUCCGCC  AGAGACCAAC  CGAGAA             96
```

( 2 ) INFORMATION FOR SEQ ID NO:52:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:52:

```
GGGAAAAGCG  AAUCAUACAC  AAGACGAUGU  UAGCGCCUCC  GGGAGAGGUU         50

AGGGUCGUGC  GGNAAGAGUG  AGGUGCUCCG  CCAGAGACCA  ACCGAGAA           98
```

( 2 ) INFORMATION FOR SEQ ID NO:53:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:53:

```
GGGAAAAGCG  AAUCAUACAC  AAGAGGUACG  GGCGAGACGA  GAUGGACUUA         50

UAGGUCGAUG  AACGGGUAGC  AGCUCGCUCC  GCCAGAGACC  AACCGAGAA          99
```

( 2 ) INFORMATION FOR SEQ ID NO:54:

( i ) SEQUENCE CHARACTERISTICS:
        ( A ) LENGTH: 96 base pairs
        ( B ) TYPE: nucleic acid
        ( C ) STRANDEDNESS: single ( D ) TOPOLOGY: linear ( i i ) MOLECULE TYPE: RNA ( i x ) FEATURE:
            ( D ) OTHER INFORMATION: All C's are 2'-NH2 cytosine ( i x ) FEATURE:
            ( D ) OTHER INFORMATION: All U's are 2'-NH2 uracil ( x i ) SEQUENCE DESCRIPTION: SEQ ID NO:54:

```
GGGAAAAGCG AAUCAUACAC AAGACGGUUG CUGAACAGAA CGUGAGUCUU        50
GGUGAGUCGC ACAGAUUGUC CUGCUCCGCC AGAGACCAAC CGAGAA            96
```

( 2 ) INFORMATION FOR SEQ ID NO:55:

( i ) SEQUENCE CHARACTERISTICS:
            ( A ) LENGTH: 97 base pairs
            ( B ) TYPE: nucleic acid
            ( C ) STRANDEDNESS: single
            ( D ) TOPOLOGY: linear ( i i ) MOLECULE TYPE: RNA ( i x ) FEATURE:
            ( D ) OTHER INFORMATION: All C's are 2'-NH2 cytosine ( i x ) FEATURE:
            ( D ) OTHER INFORMATION: All U's are 2'-NH2 uracil ( x i ) SEQUENCE DESCRIPTION: SEQ ID NO:55:

```
GGGAAAAGCG AAUCAUACAC AAGAACUGAG UAAGGUCUGG CGUGGCAUUA        50
GGUUAGUGGG AGGCUUGGAG UAGGCUCCGC CAGAGACCAA CCGAGAA           97
```

( 2 ) INFORMATION FOR SEQ ID NO:56:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: RNA ( i x ) FEATURE:
            ( D ) OTHER INFORMATION: All C's are 2'-NH2 cytosine ( i x ) FEATURE:
            ( D ) OTHER INFORMATION: All U's are 2'-NH2 uracil ( x i ) SEQUENCE DESCRIPTION: SEQ ID NO:56:

```
AAGACUCGGC GGGAACGAAA                                         20
```

( 2 ) INFORMATION FOR SEQ ID NO:57:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: RNA ( i x ) FEATURE:
            ( D ) OTHER INFORMATION: All C's are 2'-NH2 cytosine ( i x ) FEATURE:
            ( D ) OTHER INFORMATION: All U's are 2'-NH2 uracil ( x i ) SEQUENCE DESCRIPTION: SEQ ID NO:57:

```
GGAGUCGUGA CGAACC                                             16
```

( 2 ) INFORMATION FOR SEQ ID NO:58:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:58:

CCUAGGGAUG CAACGG     16

( 2 ) INFORMATION FOR SEQ ID NO:59:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:59:

RCUGGGAGRG UGGGUGUU     18

( 2 ) INFORMATION FOR SEQ ID NO:60:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:60:

UGUGNNNNAG UNNNNNNNNN UAGACGUCGG UGGACNNNGC GG     42

( 2 ) INFORMATION FOR SEQ ID NO:61:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:61:

GGGNNNGUGA CYCGRGGAYU C                                                                    2 1

( 2 ) INFORMATION FOR SEQ ID NO:62:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:62:

UGANCNNACU GGUGNNNGNG NAG                                                                  2 3

( 2 ) INFORMATION FOR SEQ ID NO:63:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:63:

GUCUCYGAAC NNGGNAGGAN GUGNUGGAGN UG                                                        3 2

( 2 ) INFORMATION FOR SEQ ID NO:64:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:64:

GGGAGGACGA UGCGGNNNN NNNNNNNNN NNNNNNNNN NNNNNNNNN                                         5 0

NNNNNCAGAC GACUCGCCCG A                                                                    7 1

( 2 ) INFORMATION FOR SEQ ID NO:65:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:65:

TAATACGACT CACTATAGGG AGGACGATGC GG                                32

( 2 ) INFORMATION FOR SEQ ID NO:66:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:66:

TCGGGCGAGT CGTCCTG                                                 17

( 2 ) INFORMATION FOR SEQ ID NO:67:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:67:

GGGAGGACGA UGCGGCGCGU AUGUGUGAAA GCGUGUGCAC GGAGGCGUCU             50

ACAAUCAGAC GACUCGCCCG A                                            71

( 2 ) INFORMATION FOR SEQ ID NO:68:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:68:

GGGAGGACGA UGCGGGGCAU UGUGUGAAUA GCUGAUCCCA CAGGUAACAA             50

CAGCACAGAC GACUCGCCCG A                                            71

( 2 ) INFORMATION FOR SEQ ID NO:69:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:69:

GGGAGGACGA UGCGGUAAUG UGUGAAUCAA GCAGUCUGAA UAGAUUAGAC      50

AAAAUCAGAC GACUCGCCCG A                                    71

( 2 ) INFORMATION FOR SEQ ID NO:70:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:70:

GGGAGGACGA UGCGGAUGUG UGAGUAGCUG AGCGCCCGAG UAUGAWACCU      50

GACUACAGAC GACUCGCCCG A                                    71

( 2 ) INFORMATION FOR SEQ ID NO:71:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:71:

GGGAGGACGA UGCGGAAACC UUGAUGUGUG AUAGAGCAUC CCCCAGGCGA      50

CGUACCAGAC GACUCGCCCG A                                    71

( 2 ) INFORMATION FOR SEQ ID NO:72:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:72:

GGGAGGACGA UGCGGUUGAG AUGUGUGAGU ACAAGCUCAA AAUCCCGUUG     50

GAGGCAGACG ACUCGCCCGA     70

( 2 ) INFORMATION FOR SEQ ID NO:73:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:73:

GGGAGGACGA UGCGGUAGAG GUAGUAUGUG UGGGAGAUGA AAAUACUGUG     50

GAAAGCAGAC GACUCGCCCG A     71

( 2 ) INFORMATION FOR SEQ ID NO:74:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:74:

GGGAGGACGA UGCGGAAAGU UAUGAGUCCG UAUAUCAAGG UCGACAUGUG     50

UGAAUCAGAC GACUCGCCCG A     71

( 2 ) INFORMATION FOR SEQ ID NO:75:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:75:

GGGAGGACGA UGCGGCACGA AAAACCCGAA UUGGGUCGCC CAUAAGGAUG     50

UGUGACAGAC GACUCGCCCG A     71

( 2 ) INFORMATION FOR SEQ ID NO:76:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:76:

```
GGGAGGACGA UGCGGGUAAA GAGAUCCUAA UGGCUCGCUA GAUGUGAUGU        50

GAAACCAGAC GACUCGCCCG A                                       71
```

( 2 ) INFORMATION FOR SEQ ID NO:77:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:77:

```
GGGAGGACGA UGCGGUAACA ACAAUCAAGG CGGGUUCACC GCCCCAGUAU        50

GAGUGCAGAC GACUCGCCCG A                                       71
```

( 2 ) INFORMATION FOR SEQ ID NO:78:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:78:

```
GGGAGGACGA UGCGGUAACA ACAAUCAAGG CGGGUUYACC GCCCCAGUAU        50

GAGUACAGAC GACUCGCCCG A                                       71
```

( 2 ) INFORMATION FOR SEQ ID NO:79:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: RNA ( i x ) FEATURE:

( D ) OTHER INFORMATION: All C's are 2'-NH2 cytosine ( i x ) FEATURE:
( D ) OTHER INFORMATION: All U's are 2'-NH2 uracil ( x i ) SEQUENCE DESCRIPTION: SEQ ID NO:79:

| GGGAGGACGA | UGCGGUAACA | ACAAUCAAGG | CGGGUUYACC | GCUCCAGUAU | 50 |
| GAGUACAGAC | GACUCGCCCG | A | | | 71 |

( 2 ) INFORMATION FOR SEQ ID NO:80:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All C's are 2'-NH2 cytosine ( i x ) FEATURE:
( D ) OTHER INFORMATION: All U's are 2'-NH2 uracil ( x i ) SEQUENCE DESCRIPTION: SEQ ID NO:80:

| GGGAGGACGA | UGCGGUAACA | ACAAUCAAGG | CGGGUUCACC | GCCCCAGUAU | 50 |
| GAGUGCAGAC | GACUCGCCCG | A | | | 71 |

( 2 ) INFORMATION FOR SEQ ID NO:81:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All C's are 2'-NH2 cytosine ( i x ) FEATURE:
( D ) OTHER INFORMATION: All U's are 2'-NH2 uracil ( x i ) SEQUENCE DESCRIPTION: SEQ ID NO:81:

| GGGAGGACGA | UGCGGACCAA | GCAAUCUAUG | GUCGAACGCU | ACACAUGAAU | 50 |
| GACGUCAGAC | GACUCGCCCG | A | | | 71 |

( 2 ) INFORMATION FOR SEQ ID NO:82:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All C's are 2'-NH2 cytosine ( i x ) FEATURE:
( D ) OTHER INFORMATION: All U's are 2'-NH2 uracil ( x i ) SEQUENCE DESCRIPTION: SEQ ID NO:82:

| GGGAGGACGA | UGCGGGAACA | UGAAGUAAUC | AAAGUCGUAC | CAAUAUACAG | 50 |
| GAAGCCAGAC | GACUCGCCCG | A | | | 71 |

( 2 ) INFORMATION FOR SEQ ID NO:83:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:83:

```
GGGAGGACGA UGCGGGACAU GAAGUAAGAC CGUCACAAUU CGAAUGAUUG      50
AAUACAGACG ACUCGCCCGA                                       70
```

( 2 ) INFORMATION FOR SEQ ID NO:84:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:84:

```
GGGAGGACGA UGCGGGAACA UGAAGUAAAA AGUCGACGAA UUAGCUGUAA      50
CCAAAACAGA CGACUCGCCC GA                                    72
```

( 2 ) INFORMATION FOR SEQ ID NO:85:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:85:

```
GGGAGGACGA UGCGGGAACA UGAAGUAAAA GUCUGAGUUA GUAAAUUACA      50
GUGAUCAGAC GACUCGCCCG A                                     71
```

( 2 ) INFORMATION FOR SEQ ID NO:86:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:86:

GGGAGGACGA UGCGGGAACU UGAAGUUGAA NUCGCUAAGG UUAUGGAUUC           50

AAGAUUCAGA CGACUCGCCC GA                                        72

( 2 ) INFORMATION FOR SEQ ID NO:87:

( i ) SEQUENCE CHARACTERISTICS:
                ( A ) LENGTH: 71 base pairs
                ( B ) TYPE: nucleic acid
                ( C ) STRANDEDNESS: single
                ( D ) TOPOLOGY: linear ( i i ) MOLECULE TYPE: RNA ( i x ) FEATURE:
                ( D ) OTHER INFORMATION: All C's are 2'-NH2 cytosine ( i x ) FEATURE:
                ( D ) OTHER INFORMATION: All U's are 2'-NH2 uracil ( x i ) SEQUENCE DESCRIPTION: SEQ ID NO:87:

GGGAGGACGA UGCGGAACAU GAAGUAAUAA GUCGACGUAA UUAGCUGUAA           50

CUAAACAGAC GACUCGCCCG A                                         71

( 2 ) INFORMATION FOR SEQ ID NO:88:

( i ) SEQUENCE CHARACTERISTICS:
                ( A ) LENGTH: 70 base pairs
                ( B ) TYPE: nucleic acid
                ( C ) STRANDEDNESS: single
                ( D ) TOPOLOGY: linear ( i i ) MOLECULE TYPE: RNA ( i x ) FEATURE:
                ( D ) OTHER INFORMATION: All C's are 2'-NH2 cytosine ( i x ) FEATURE:
                ( D ) OTHER INFORMATION: All U's are 2'-NH2 uracil ( x i ) SEQUENCE DESCRIPTION: SEQ ID NO:88:

GGGAGGACGA UGCGGAACAU GAAGUAAAAG UCUGAGUUAG AAAUUACAAG           50

UGAUCAGACG ACUCGCCCGA                                           70

( 2 ) INFORMATION FOR SEQ ID NO:89:

( i ) SEQUENCE CHARACTERISTICS:
                ( A ) LENGTH: 71 base pairs
                ( B ) TYPE: nucleic acid
                ( C ) STRANDEDNESS: single
                ( D ) TOPOLOGY: linear ( i i ) MOLECULE TYPE: RNA ( i x ) FEATURE:
                ( D ) OTHER INFORMATION: All C's are 2'-NH2 cytosine ( i x ) FEATURE:
                ( D ) OTHER INFORMATION: All U's are 2'-NH2 uracil ( x i ) SEQUENCE DESCRIPTION: SEQ ID NO:89:

GGGAGGACGA UGCGGUAACA UAAAGUAGCG CGUCUGUGAG AGGAAGUGCC           50

UGGAUCAGAC GACUCGCCCG A                                         71

( 2 ) INFORMATION FOR SEQ ID NO:90:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:90:

| GGGAGGACGA | UGCGGAUAGA | ACCGCAAGGA | UAACCUCGAC | CGUGGUCAAC | 50 |
|---|---|---|---|---|---|
| UGAGACAGAC | GACUCGCCCG | A | | | 71 |

( 2 ) INFORMATION FOR SEQ ID NO:91:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:91:

| GGGAGGACGA | UGCGGUAAGA | ACCGCUAGCG | CACGAUCAAA | CAAAGAGAAA | 50 |
|---|---|---|---|---|---|
| CAAACAGACG | ACUCGCCCGA | | | | 70 |

( 2 ) INFORMATION FOR SEQ ID NO:92:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:92:

| GGGAGGACGA | UGCGGUUCUC | UCCAAGAACY | GAGCGAAUAA | ACSACCGGAS | 50 |
|---|---|---|---|---|---|
| UCACACAGAC | GACUCGCCCG | A | | | 71 |

( 2 ) INFORMATION FOR SEQ ID NO:93:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
    ( D ) OTHER INFORMATION: All C's are 2'-NH2 cytosine ( i x ) FEATURE:
    ( D ) OTHER INFORMATION: All U's are 2'-NH2 uracil ( x i ) SEQUENCE DESCRIPTION: SEQ ID NO:93:

GGGAGGACGA UGCGGUGUCU CUCCUGACUU UUAUUCUUAG UUCGAGCUGU       50

CCUGGCAGAC GACUCGCCCG A       71

( 2 ) INFORMATION FOR SEQ ID NO:94:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:94:

GGGAGGACGA UGCGGCCGUA CAUGGUAARC CUCGAAGGAU UCCCGGGAUG       50

AUCCCCAGAC GACUCGCCCG A       71

( 2 ) INFORMATION FOR SEQ ID NO:95:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:95:

GGGAGGACGA UGCGGUCCCA GAGUCCCGUG AUGCGAAGAA UCCAUUAGUA       50

CCAGACAGAC GACUCGCCCG A       71

( 2 ) INFORMATION FOR SEQ ID NO:96:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:96:

GGGAGGACGA UGCGGGAUGU AAAUGACAAA UGAACCUCGA AAGAUUGCAC       50

ACUCCAGACG ACUCGCCCGA 70

(2) INFORMATION FOR SEQ ID NO:97:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:97:

GGGAGGACGA UGCGGAUGUA AAUCUAGGCA GAAACGUAGG GCAUCCACCG 50

CAACGACAGA CGACUCGCCC GA 72

(2) INFORMATION FOR SEQ ID NO:98:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:98:

GGGAGGACGA UGCGGAUAAC CCAAGCAGCN UCGAGAAAGA GCUCCAUAGA 50

UGAUCAGACG ACUCGCCCGA 70

(2) INFORMATION FOR SEQ ID NO:99:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:99:

GGGAGGACGA UGCGGCAAAG CACGCGUAUG GCAUGAAACU GGCANCCCAA 50

GUAAGCAGAC GACUCGCCCG A 71

(2) INFORMATION FOR SEQ ID NO:100:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:100:

GGGAGGACGA UGCGGCAAAA GGUUGACGUA GCGAAGCUCU CAAAAUGGUC      50

AUGACCAGAC GACUCGCCCG A                                    71

(2) INFORMATION FOR SEQ ID NO:101:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:101:

GGGAGGACGA UGCGGAAGUG AAGCUAAAGC GGAGGGCCAU UCAGUUUCNC      50

ACCACAGACG ACUCGCCCGA                                      70

(2) INFORMATION FOR SEQ ID NO:102:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:102:

GGGAGGACGA UGCGGAAGUG AAGCUAAAGS GGAGGGCCAC UCAGAAACGC      50

ACCACAGACG ACUCGCCCGA                                      70

(2) INFORMATION FOR SEQ ID NO:103:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All C's are 2'-NH2 cytosine (ix) FEATURE:
(D) OTHER INFORMATION: All U's are 2'-NH2 uracil (xi) SEQUENCE DESCRIPTION: SEQ ID NO:103:

GGGAGGACGA UGCGGCACCG CUAAGCAGUG GCAUAGCCCA GUAACCUGUA      50

```
AGAGACAGAC GACUCGCCCG A                                              71
```

(2) INFORMATION FOR SEQ ID NO:104:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:104:

```
GGGAGGACGA UGCGGCACGC UAAGCAGUGG CAUAGCGWAA CCUGUAAGAG              50
ACAGACGACU CGCCCGA                                                  67
```

(2) INFORMATION FOR SEQ ID NO:105:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:105:

```
GGGAGGACGA UGCGGAGAUU ACCAUAACCG CGUAGUCGAA GACAUAUAGU              50
AGCGACAGAC GACUCGCCCG A                                             71
```

(2) INFORMATION FOR SEQ ID NO:106:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:106:

```
GGGAGGACGA UGCGGACUCG GGUAGAACGC GACUUGCCAC CACUCCCAUA              50
AAGACCAGAC GACUCGCCCG A                                             71
```

(2) INFORMATION FOR SEQ ID NO:107:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
 (D) OTHER INFORMATION: All C's are 2'-NH2 cytosine (ix) FEATURE:
 (D) OTHER INFORMATION: All U's are 2'-NH2 uracil (xi) SEQUENCE DESCRIPTION: SEQ ID NO:107:

| GGGAGGACGA | UGCGGUCAGA | ACUCUGCCGC | UGUAGACAAA | GAGGAGCUUA | 50 |
| GCGAACAGAC | GACUCGCCCG | A | | | 71 |

(2) INFORMATION FOR SEQ ID NO:108:

(i) SEQUENCE CHARACTERISTICS:
  (A) LENGTH: 71 base pairs
  (B) TYPE: nucleic acid
  (C) STRANDEDNESS: single
  (D) TOPOLOGY: linear (ii) MOLECULE TYPE: RNA (ix) FEATURE:
  (D) OTHER INFORMATION: All C's are 2'-NH2 cytosine (ix) FEATURE:
  (D) OTHER INFORMATION: All U's are 2'-NH2 uracil (xi) SEQUENCE DESCRIPTION: SEQ ID NO:108:

| GGGAGGACGA | UGCGGAAUGA | GCAUCGAGAG | AGCGCGAACU | CAUCGAGCGU | 50 |
| ACUAACAGAC | GACUCGCCCG | A | | | 71 |

(2) INFORMATION FOR SEQ ID NO:109:

(i) SEQUENCE CHARACTERISTICS:
  (A) LENGTH: 71 base pairs
  (B) TYPE: nucleic acid
  (C) STRANDEDNESS: single
  (D) TOPOLOGY: linear (ii) MOLECULE TYPE: RNA (ix) FEATURE:
  (D) OTHER INFORMATION: All C's are 2'-NH2 cytosine (ix) FEATURE:
  (D) OTHER INFORMATION: All U's are 2'-NH2 uracil (xi) SEQUENCE DESCRIPTION: SEQ ID NO:109:

| GGGAGGACGA | UGCGGCAAAG | CACGCGUAUG | GCAUGAAACU | GGCANCCCAA | 50 |
| GUAAGCAGAC | GACUCGCCCG | A | | | 71 |

(2) INFORMATION FOR SEQ ID NO:110:

(i) SEQUENCE CHARACTERISTICS:
  (A) LENGTH: 71 base pairs
  (B) TYPE: nucleic acid
  (C) STRANDEDNESS: single
  (D) TOPOLOGY: linear (ii) MOLECULE TYPE: RNA (ix) FEATURE:
  (D) OTHER INFORMATION: All C's are 2'-NH2 cytosine (ix) FEATURE:
  (D) OTHER INFORMATION: All U's are 2'-NH2 uracil (xi) SEQUENCE DESCRIPTION: SEQ ID NO:110:

```
GGGAGGACGA  UGCGGGAUGC  AGCAACCUGA  AAACGGCGUC  CACAGGUAAU    50

AACAGCAGAC  GACUCGCCCG  A                                     71
```

( 2 ) INFORMATION FOR SEQ ID NO:111:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:111:

```
GGGAGGACGA  UGCGGAAACU  CGCUACAAAC  ACCCAAUCCU  AGAACGUUAU    50

GGAGACAGAC  GACUCGCCCG  A                                     71
```

( 2 ) INFORMATION FOR SEQ ID NO:112:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:112:

```
GGGAGGACGA  UGCGGCUAGC  AUAGCCACCG  GAACAGACAG  AUACGAGCAC    50

GAUCACAGAC  GACUCGCCCG  A                                     71
```

( 2 ) INFORMATION FOR SEQ ID NO:113:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:113:

```
GGGAGGACGA  UGCGGGAUUC  GGAGUACUGA  AAAACAACCC  UCAAAAGUGC    50

AUAGGCAGAC  GACUCGCCCG  A                                     71
```

( 2 ) INFORMATION FOR SEQ ID NO:114:

( i ) SEQUENCE CHARACTERISTICS:
        ( A ) LENGTH: 71 base pairs
        ( B ) TYPE: nucleic acid
        ( C ) STRANDEDNESS: single (D) TOPOLOGY: linear (ii) MOLECULE TYPE: RNA (ix) FEATURE:
 (D) OTHER INFORMATION: All C's are 2'-NH2 cytosine (ix) FEATURE:
 (D) OTHER INFORMATION: All U's are 2'-NH2 uracil (xi) SEQUENCE DESCRIPTION: SEQ ID NO:114:

| GGGAGGACGA | UGCGGGUCCA | GGACGGACCG | CAGCUGUGAU | ACAAUCGACU | 50 |
|---|---|---|---|---|---|
| UACACCAGAC | GACUCGCCCG | A | | | 71 |

(2) INFORMATION FOR SEQ ID NO:115:

(i) SEQUENCE CHARACTERISTICS:
  (A) LENGTH: 71 base pairs
  (B) TYPE: nucleic acid
  (C) STRANDEDNESS: single
  (D) TOPOLOGY: linear (ii) MOLECULE TYPE: RNA (ix) FEATURE:
  (D) OTHER INFORMATION: All C's are 2'-NH2 cytosine (ix) FEATURE:
  (D) OTHER INFORMATION: All U's are 2'-NH2 uracil (xi) SEQUENCE DESCRIPTION: SEQ ID NO:115:

| GGGAGGACGA | UGCGGAAACU | CGCUACAAAC | ACCCAAUCCU | AGAACGUUAU | 50 |
|---|---|---|---|---|---|
| GGAGACAGAC | GACUCGCCCG | A | | | 71 |

(2) INFORMATION FOR SEQ ID NO:116:

(i) SEQUENCE CHARACTERISTICS:
  (A) LENGTH: 70 base pairs
  (B) TYPE: nucleic acid
  (C) STRANDEDNESS: single
  (D) TOPOLOGY: linear (ii) MOLECULE TYPE: RNA (ix) FEATURE:
  (D) OTHER INFORMATION: All C's are 2'-NH2 cytosine (ix) FEATURE:
  (D) OTHER INFORMATION: All U's are 2'-NH2 uracil (xi) SEQUENCE DESCRIPTION: SEQ ID NO:116:

| GGGAGGACGA | UGCGGCGGCC | CUUAUCGGAG | GUCUGCGCCA | CUAAUUACAU | 50 |
|---|---|---|---|---|---|
| CCACCAGACG | ACUCGCCCGA | | | | 70 |

(2) INFORMATION FOR SEQ ID NO:117:

(i) SEQUENCE CHARACTERISTICS:
  (A) LENGTH: 67 base pairs
  (B) TYPE: nucleic acid
  (C) STRANDEDNESS: single
  (D) TOPOLOGY: linear (ii) MOLECULE TYPE: RNA (ix) FEATURE:
  (D) OTHER INFORMATION: All C's are 2'-NH2 cytosine (ix) FEATURE:
  (D) OTHER INFORMATION: All U's are 2'-NH2 uracil (xi) SEQUENCE DESCRIPTION: SEQ ID NO:117:

```
GGGAGGACGA UGCGGUCCAG AGCGUGAAGA UCAACGUCCC GGNGUCGAAG          50

ACAGACGACU CGCCCGA                                              67
```

( 2 ) INFORMATION FOR SEQ ID NO:118:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:118:

```
AUGUGUGA                                                         8
```

( 2 ) INFORMATION FOR SEQ ID NO:119:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:119:

```
CAACAAUCAU GAGUR                                                15
```

( 2 ) INFORMATION FOR SEQ ID NO:120:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-NH2 cytosine ( i x ) FEATURE:
        ( D ) OTHER INFORMATION: All U's are 2'-NH2 uracil ( x i ) SEQUENCE DESCRIPTION: SEQ ID NO:120:

```
AACAUGAAGU AAGUCARUUA G                                         21
```

( 2 ) INFORMATION FOR SEQ ID NO:121:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:

(D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:121:

AGAACCGCWA G                                                                11

(2) INFORMATION FOR SEQ ID NO:122:

(i) SEQUENCE CHARACTERISTICS:
            (A) LENGTH: 7 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:122:

UCUCUCC                                                                      7

(2) INFORMATION FOR SEQ ID NO:123:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:123:

CGAAGAAUYC                                                                  10

(2) INFORMATION FOR SEQ ID NO:124:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:124:

AUGUAAAU                                                                     8

(2) INFORMATION FOR SEQ ID NO:125:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (i i) MOLECULE TYPE: RNA (i x) FEATURE:
(D) OTHER INFORMATION: All C's are 2'-NH2 cytosine (i x) FEATURE:
(D) OTHER INFORMATION: All U's are 2'-NH2 uracil (x i) SEQUENCE DESCRIPTION: SEQ ID NO:125:

AACCCAAG  8

(2) INFORMATION FOR SEQ ID NO:126:

(i) SEQUENCE CHARACTERISTICS:
(A) LENGTH: 80 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:126:

CTACCTACGA TCTGACTAGC NNNNNNNNNN NNNNNNNNNN NNNNNNNNNN  50

NNNNNNNNNN GCTTACTCTC ATGTAGTTCC  80

(2) INFORMATION FOR SEQ ID NO:127:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:127:

CTACCTACGA TCTGACTAGC  20

(2) INFORMATION FOR SEQ ID NO:128:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:128:

AGGAACTACA TGAGAGTAAG C  21

(2) INFORMATION FOR SEQ ID NO:129:

(i) SEQUENCE CHARACTERISTICS:
(A) LENGTH: 80 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:129:

CTACCTACGA TCTGACTAGC GGAACACGTG AGGTTTACAA GGCACTCGAC  50

GTAAACACTT GCTTACTCTC ATGTAGTTCC  80

(2) INFORMATION FOR SEQ ID NO:130:

( i ) SEQUENCE CHARACTERISTICS:
  ( A ) LENGTH: 80 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:130:

CTACCTACGA TCTGACTAGC CCCCGAAGAA CATTTTACAA GGTGCTAAAC    50

GTAAAATCAG GCTTACTCTC ATGTAGTTCC    80

( 2 ) INFORMATION FOR SEQ ID NO:131:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:131:

CTACCTACGA TCTGACTAGC GGCATCCTG AGTCATTACA AGGTTCTTAA    50

CGTAATGTAC GCTTACTCTC ATGTAGTTCC    80

( 2 ) INFORMATION FOR SEQ ID NO:132:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:132:

CTACCTACGA TCTGACTAGC TGCACACCTG AGGGTTACAA GGCGCTAGAC    50

GTAACCTCTC GCTTACTCTC ATGTAGTTCC    80

( 2 ) INFORMATION FOR SEQ ID NO:133:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:133:

CTACCTACGA TCTGACTAGC CACGTTTCAA GGGGTTACAC GAAACGATTC    50

ACTCCTTGGC GCTTACTCTC ATGTAGTTCC    80

( 2 ) INFORMATION FOR SEQ ID NO:134:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:134:

CTACCTACGA TCTGACTAGC CGGACATGAG CGTTACAAGG TGCTAAACGT    50

```
AACGTACTTG CTTACTCTCA TGTAGTTCC                                              79
```

( 2 ) INFORMATION FOR SEQ ID NO:135:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:135:

```
CTACCTACGA TCTGACTAGC CGCATCCACA TAGTTCAAGG GGCTACACGA                        50

AATATTGCAG CTTACTCTCA TGTAGTTCC                                              79
```

( 2 ) INFORMATION FOR SEQ ID NO:136:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:136:

```
CTACCTACGA TCTGACTAGC TACCCCTTGG GCCTCATAGA CAAGGTCTTA                        50

AACGTTAGCG CTTACTCTCA TGTAGTTCC                                              79
```

( 2 ) INFORMATION FOR SEQ ID NO:137:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:137:

```
CTACCTACGA TCTGACTAGC CACATGCCTG ACGCGGTACA AGGCCTGGAC                        50

GTAACGTTGG CTTACTCTCA TGTAGTTCC                                              79
```

( 2 ) INFORMATION FOR SEQ ID NO:138:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:138:

```
CTACCTACGA TCTGACTAGC TAGTGCTCCA CGTATTCAAG GTGCTAAACG                        50

AAGACGGCCT GCTTACTCTC ATGTAGTTCC                                             80
```

( 2 ) INFORMATION FOR SEQ ID NO:139:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:139:

CTACCTACGA TCTGACTAGC AGCGATGCAA GGGGCTACAC GCAACGATTT 50

AGATGCTCTG CTTACTCTCA TGTAGTTCC 79

( 2 ) INFORMATION FOR SEQ ID NO:140:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:140:

CTACCTACGA TCTGACTAGC CCAGGAGCAC AGTACAAGGT GTTAAACGTA 50

ATGTCTGGTG CTTACTCTCA TGTAGTTCC 79

( 2 ) INFORMATION FOR SEQ ID NO:141:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:141:

CTACCTACGA TCTGACTAGC ACCACACCTG GGCGGTACAA GGAGTTATCC 50

GTAACGTGTG CTTACTCTCA TGTAGTTCC 79

( 2 ) INFORMATION FOR SEQ ID NO:142:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:142:

CTACCTACGA TCTGACTAGC CAAGGTAACC AGTACAAGGT GCTAAACGTA 50

ATGGCTTCGG CTTACTCTCA TGTAGTTCC 79

( 2 ) INFORMATION FOR SEQ ID NO:143:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:143:

CTACCTACGA TCTGACTAGC ACCCCCGACC CGAGTACAAG GCATTCGACG 50

TAATCTGGTG CTTACTCTCA TGTAGTTCC 79

( 2 ) INFORMATION FOR SEQ ID NO:144:

( i ) SEQUENCE CHARACTERISTICS:
        ( A ) LENGTH: 79 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:144:

```
CTACCTACGA TCTGACTAGC CAGTACAAGG TGTTAAACGT AATGCCGATC        50

GAGTTGTATG CTTACTCTCA TGTAGTTCC                               79
```

( 2 ) INFORMATION FOR SEQ ID NO:145:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:145:

```
CTACCTACGA TCTGACTAGC ACAACGAGTA CAAGGAGATA GACGTAATCG        50

GCGCAGGTAT CGCTTACTCT CATGTAGTTC C                            81
```

( 2 ) INFORMATION FOR SEQ ID NO:146:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:146:

```
CTACCTACGA TCTGACTAGC CACGACAGAG AACAAGGCGT TAGACGTTAT        50

CCGACCACGG CTTACTCTCA TGTAGTTCC                               79
```

( 2 ) INFORMATION FOR SEQ ID NO:147:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:147:

```
CTACCTACGA TCTGACTAGC AGGGAGAACA AGGTGCTAAA CGTTTATCTA        50

CACTTCACCT GCTTACTCTC ATGTAGTTCC                              80
```

( 2 ) INFORMATION FOR SEQ ID NO:148:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:148:

```
CTACCTACGA TCTGACTAGC AGGACCAAGG TGTTAAACGG CTCCCTGGC         50

TATGCCTCTT GCTTACTCTC ATGTAGTTCC                              80
```

(2) INFORMATION FOR SEQ ID NO:149:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:149:

| CTACCTACGA | TCTGACTAGC | TACACAAGGT | GCTAAACGTA | GAGCCAGATC | 50 |
| GGATCTGAGC | GCTTACTCTC | ATGTAGTTCC | | | 80 |

(2) INFORMATION FOR SEQ ID NO:150:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:150:

| CTACCTACGA | TCTGACTAGC | GGACAAGGCA | CTCGACGTAG | TTTATAACTC | 50 |
| CCTCCGGGCC | GCTTACTCTC | ATGTAGTTCC | | | 80 |

(2) INFORMATION FOR SEQ ID NO:151:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:151:

| CTACCTACGA | TCTGACTAGC | TACACAAGGG | GCCAAACGGA | GAGCCAGACG | 50 |
| CGGATCTGAC | AGCTTACTCT | CATGTAGTTC | C | | 81 |

(2) INFORMATION FOR SEQ ID NO:152:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:152:

| CTACCTACGA | TCTGACTAGC | CGGCTATACN | NGGTGCTAAA | CGCAGAGACT | 50 |
| CGATCAACAG | CTTACTCTCA | TGTAGTTCC | | | 79 |

(2) INFORMATION FOR SEQ ID NO:153:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:153:

```
CTACCTACGA  TCTGACTAGC  GAGTAGCCAA  GGCGTTAGAC  GGAGGGGGAA          50

TGGAAGCTTG  GCTTACTCTC  ATGTAGTTCC                                  80
```

( 2 ) INFORMATION FOR SEQ ID NO:154:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:154:

```
CTACCTACGA  TCTGACTAGC  GAGTAGCCAA  GGCGTTAGAC  GGAGGGGGAA          50

TGGGCTTACT  CTCATGTAGT  TCC                                         73
```

( 2 ) INFORMATION FOR SEQ ID NO:155:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:155:

```
CTACCTACGA  TCTGACTAGC  GAGTAGCCAA  GGCGTTAGAC  GGAGGGGGAA          50

TGTGAGCACA  GCTTACTCTC  ATGTAGTTCC                                  80
```

( 2 ) INFORMATION FOR SEQ ID NO:156:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:156:

```
CTACCTACGA  TCTGACTAGC  TAGCTCCACA  CACAASSCGC  RGCACATAGG          50

GGATATCTGG  GCTTACTCTC  ATGTAGTTCC                                  80
```

( 2 ) INFORMATION FOR SEQ ID NO:157:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:157:

```
CTACCTACGA  TCTGACTAGC  CATCAAGGAC  TTTGCCCGAA  ACCCTAGGTT          50

CACGTGTGGG  GCTTACTCTC  ATGTAGTTCC                                  80
```

( 2 ) INFORMATION FOR SEQ ID NO:158:

( i ) SEQUENCE CHARACTERISTICS:
        ( A ) LENGTH: 79 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:158:

| CTACCTACGA | TCTGACTAGC | CATTCACCAT | GGCCCCTTCC | TACGTATGTT | 50 |
| CTGCGGGTGG | CTTACTCTCA | TGTAGTTCC | | | 79 |

( 2 ) INFORMATION FOR SEQ ID NO:159:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:159:

| CTACCTACGA | TCTGACTAGC | GCAACGTGGC | CCCGTTTAGC | TCATTTGACC | 50 |
| GTTCCATCCG | GCTTACTCTC | ATGTAGTTCC | | | 80 |

( 2 ) INFORMATION FOR SEQ ID NO:160:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:160:

| CTACCTACGA | TCTGACTAGC | CCACAGACAA | TCGCAGTCCC | CGTGTAGCTC | 50 |
| TGGGTGTCTG | CTTACTCTCA | TGTAGTTCC | | | 79 |

( 2 ) INFORMATION FOR SEQ ID NO:161:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:161:

| CTACCTACGA | TCTGACTAGC | CCACCGTGAT | GCACGATACA | TGAGGGTGTG | 50 |
| TCAGCGCATG | CTTACTCTCA | TGTAGTTCC | | | 79 |

( 2 ) INFORMATION FOR SEQ ID NO:162:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:162:

| CTACCTACGA | TCTGACTAGC | CGAGGTAGTC | GTTATAGGGT | RCRCACGACA | 50 |
| CAAARCRGTR | GCTTACTCTC | ATGTAGTTCC | | | 80 |

( 2 ) INFORMATION FOR SEQ ID NO:163:

(i) SEQUENCE CHARACTERISTICS:
  (A) LENGTH: 79 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:163:

```
CTACCTACGA TCTGACTAGC TGGCGGTACG GGCCGTGCAC CCACTTACCT        50
GGGAAGTGAG CTTACTCTCA TGTAGTTCC                              79
```

(2) INFORMATION FOR SEQ ID NO:164:

(i) SEQUENCE CHARACTERISTICS:
  (A) LENGTH: 81 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:164:

```
CTACCTACGA TCTGACTAGC CTCTGCTTAC CTCATGTAGT TCCAAGCTTG        50
GCGTAATCAT GGCTTACTCT CATGTAGTTC C                           81
```

(2) INFORMATION FOR SEQ ID NO:165:

(i) SEQUENCE CHARACTERISTICS:
  (A) LENGTH: 79 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:165:

```
CTACCTACGA TCTGACTAGC AGCGTTGTAC GGGGTTACAC ACAACGATTT        50
AGATGCTCTG CTTACTCTCA TGTAGTTCC                              79
```

(2) INFORMATION FOR SEQ ID NO:166:

(i) SEQUENCE CHARACTERISTICS:
  (A) LENGTH: 81 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:166:

```
CTACCTACGA TCTGACTAGC TGATGCGACT TTAGTCGAAC GTTACTGGGG        50
CTCAGAGGAC AGCTTACTCT CATGTAGTTC C                           81
```

(2) INFORMATION FOR SEQ ID NO:167:

(i) SEQUENCE CHARACTERISTICS:
  (A) LENGTH: 81 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:167:

```
CTACCTACGA TCTGACTAGC CGAGGATCTG ATACTTATTG AACATAMCCG        50
```

CACNCAGGCT TGCTTACTCT CATGTAGTTC C  81

(2) INFORMATION FOR SEQ ID NO:168:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:168:

TACAAGGYGY TAVACGTA  18

(2) INFORMATION FOR SEQ ID NO:169:

(i) SEQUENCE CHARACTERISTICS:
      (A) LENGTH: 8 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:169:

GGCCCCGT  8

(2) INFORMATION FOR SEQ ID NO:170:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:170:

RCACGAYACA  10

(2) INFORMATION FOR SEQ ID NO:171:

(i) SEQUENCE CHARACTERISTICS:
      (A) LENGTH: 7 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:171:

CTTACCT  7

(2) INFORMATION FOR SEQ ID NO:172:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:172:

CAAGGTAACC AGTACAAGGT GCTAAACGTA ATGGCTTCG  39

(2) INFORMATION FOR SEQ ID NO:173:

( i ) SEQUENCE CHARACTERISTICS:
   ( A ) LENGTH: 35 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:173:

GTAACCAGTA CAAGGTGCTA AACGTAATGG CTTCG    35

METHOD FOR IDENTIFICATION OF HIGH AFFINITY NUCLEIC ACID LIGANDS TO SELECTINS

RELATED APPLICATIONS

This application is a Continuation-in-Part of U.S. patent application Ser. No. 07/714,131, filed Jun. 10, 1991, entitled Nucleic Acid Ligands now U.S. Pat. No. 5,475,096, which is a Continuation-in Part of U.S. patent application Ser. No. 07/536,428, filed Jun. 11, 1990, entitled Systematic Evolution of Ligands by Exponential Enrichment, now abandoned, and U.S. patent application Ser. No. 07/964,624, filed Oct. 21, 1992, entitled Methods of Producing Nucleic Acid Ligands, now U.S. Pat. No. 5,496,938.

FIELD OF THE INVENTION

Described herein are methods for identifying and preparing high-affinity nucleic acid ligands to lectins. Lectins are carbohydrate binding proteins. The method utilized herein for identifying such nucleic acid ligands is called SELEX, an acronym for Systematic Evolution of Ligands by EXponential enrichment. Specifically disclosed herein are high-affinity nucleic acid ligands to wheat germ agglutinin (WGA), L-selectin, E-selectin, and P-selectin.

BACKGROUND OF THE INVENTION

The biological role of lectins (non-enzymatic carbohydrate-binding proteins of non-immune origin; I. J. Goldstein et al., 1980, Nature 285:66) is inextricably linked to that of carbohydrates. One function of carbohydrates is the modification of physical characteristics of glyco-conjugates (ie., solubility, stability, activity, susceptibility to enzyme or antibody recognition), however, a more interesting and relevant aspect of carbohydrate biology has emerged in recent years; the carbohydrate portions of glyco-conjugates are information rich molecules (N. Sharon and H. Lis, 1989, Science 246:227–234; K. Drickamer and M. Taylor, 1993, Annu. Rev. Cell Biol. 9:237–264; A. Varki, 1993, Glycobiol. 3:97–130). Within limits, the binding of carbohydrates by lectins is specific (ie., there are lectins that bind only galactose or N-acetylgalactose; other lectins bind mannose; still others bind sialic acid and so on; K. Drickamer and M. Taylor, supra). Specificity of binding enables lectins to decode information contained in the carbohydrate portion of glyco-conjugates and thereby mediate many important biological functions.

Numerous mammalian, plant, microbial and viral lectins have been described (I. Ofek and N. Sharon, 1990, Current Topics in Microbiol. and Immunol. 151:91–113; K. Drickamer and M. Taylor,supra; I. J. Goldstein and R. D. Poretz, 1986, in The Lectins, pp 33–247; A. Varki, supra). These proteins mediate a diverse array of biological processes which include: trafficking of lysosomal enzymes, clearance of serum proteins, endocytosis, phagocytosis, opsonization, microbial and viral infections, toxin binding, fertilization, immune and inflammatory responses, cell adhesion and migration in development and in pathological conditions such as metastasis. Roles in symbiosis and host defense have been proposed for plant lectins but remain controversial. While the functional role of some lectins is well understood, that of many others is understood poorly or not at all.

The diversity and importance of processes mediated by lectins is illustrated by two well documented mammalian lectins, the asialoglycoprotein receptor and the serum mannose binding protein, and by the viral lectin, influenza virus hemagglutinin. The hepatic asialoglycoprotein receptor specifically binds galactose and N-acetylgalactose and thereby mediates the clearance of serum glycoproteins that present terminal N-acetylgalactose or galactose residues, exposed by the prior removal of a terminal sialic acid. The human mannose-binding protein (MBP) is a serum protein that binds terminal mannose, fucose and N-acetylglucosamine residues. These terminal residues are common on microbes but not mammalian glyco-conjugates. The binding specificity of MBP constitutes a non-immune mechanism for distinguishing self from non-self and mediates host defense through opsonization and complement fixation. Influenza virus hemagglutinin mediates the initial step of infection, attachment to nasal epithelial cells, by binding sialic acid residues of cell-surface receptors.

The diversity of lectin mediated functions provides a vast array of potential therapeutic targets for lectin antagonists. Both lectins that bind endogenous carbohydrates and those that bind exogenous carbohydrates are target candidates. For example, antagonists to the mammalian selecting, a family of endogenous carbohydrate binding lectins, may have therapeutic applications in a variety of leukocyte-mediated disease states. Inhibition of selectin binding to its receptor blocks cellular adhesion and consequently may be useful in treating inflammation, coagulation, transplant rejection, tumor metastasis, rheumatoid arthritis, reperfusion injury, stroke, myocardial infarction, burns, psoriasis, multiple sclerosis, bacterial sepsis, hypovolaemic and traumatic shock, acute lung injury, and ARDS.

The selecting, E-, P- and L-, are three homologous C-type lectins that recognise the tetrasaccharide, sialyl-Lewis$^x$ (C. Foxall et al, 1992, J. Cell Biol 117,895–902). Selectins mediate the initial adhesion of neutrophils and monocytes to activated vascular endothelium at sites of inflammation (R. S. Cotran et al., 1986, J. Exp. Med 164, 661-; M. A. Jutila et al., 1989, J. Immunol. 143,3318-:J. G. Geng et al, 1990, Nature, 757; U. H. Von Adrian et al., 1994, Am. J. Physiol. Heart Circ. Physiol 263, H1034–H1044). In addition, L-selectin is responsible for the homing of lymphocytes to peripheral and mesenteric lymph nodes (W. M. Gallatin et al, 1983, Nature 304,30; T. K. Kishimoto et al, 1990, Proc. Natl. Acad. Sci. 87,2244-) and P-selectin mediates the adherence of platelets to neutrophils and monocytes (S-C. Hsu-Lin et al., 1984, J. Biol. Chem. 259.9121).

Selectin antagonists (antibodies and carbohydrates) have been shown to block the extravasation of neutrophils at sites of inflammation (P. Piscueta and F. W. Luscinskas, 1994, Am. J. Pathol. 145, 461–469), to be effacacious in animal models of ischemia/reperfusion (A. S. Weyrich et al., 1993, J. Clin. Invest. 91,2620–2629; R. K. Winn et al., 1993, J. Clin. Invest. 92, 2042–2047), acute lung injury (M. S. Mulligan et al., 1993, J. Immunol. 151, 6410–6417; A. Seekamp it al., 1994, Am. J. Pathol. 144, 592–598), insulitis/diabetes (X. D. Yang et al., 1993, Proc. Natl. Acad. Sci. 90,10494–10498), meningitis (C. Granet et al., 1994, J. Clin. Invest. 93, 929–936), hemorrhagic shock (R. K. Winn et al., 1994, Am J. Physiol. Heart Circ. Physiol. 267, H2391–H2397) and transplantation. In addition, selectin expression has been documented in models of arthritis (F. Jamar et al., 1995, Radiology 194. 843–850), experimental allergic encephalomyelitis (J. M. Dopp et al., 1994, J. Neuroimmunol. 54, 129–144), cutaneous inflammation (A. Siber et al., 1994, Lab. Invest. 70, 163–170) glomerulonephritis (P. G. Tipping et al., 1994, Kidney Int. 46,79–88), on leukaemic cells and colon carcinomas (R. M. Lafrenie et al., 1994, Eur. J. Cancer [A] 30A, 2151–2158) and L-selectin receptors have been observed in myelinated regions of the central nervous system (K. Huang et al., 1991, J. Clin. Invest. 88, 1778–1783). The animal model data strongly support the expectation of a therapeutic role for selectin antagonists in a wide variety of disease states in which host tissue damage is neutrophil-mediated.

Other examples of lectins that recognize endogenous carbohydrates are CD22β, CD23, CD44 and sperm lectins (A. Varki, 1993, Glycobiol.3, 97–130; P. M. Wassarman, 1988, Ann. Rev. Biochem. 57, 415–442). CD22β is involved in early stages of B lymphocyte activation; antagonists may modulate the immune response. CD23 is the low affinity IgE receptor; antagonists may modulate the IgE response in allergies and asthma. CD44 binds hyaluronic acid and thereby mediates cell/cell and cell/matrix adhesion; antagonists may modulate the inflammatory response. Sperm lectins are thought to be involved in sperm/egg adhesion and in the acrosomal response; antagonists may be effective contraceptives, either by blocking adhesion or by inducing a premature, spermicidal acrosomal response.

Antagonists to lectins that recognise exogenous carbohydrates may have wide application for the prevention of infectious diseases. Many viruses (influenza A, B and C; Sendhi, Newcastle disease, coronavirus, rotavirus, encephalomyelitis virus, enchephalomyocarditis virus, reovirus, paramyxovirus) use lectins on the surface of the viral particle for attachment to cells, a prerequiste for infection; antagonists to these lectins are expected to prevent infection (A. Varki, 1993, Glycobiol.3,97–130). Similarly colonization/infection strategies of many bacteria utilize cell surface lectins to adhere to mammalian cell surface glycoconjugates. Antagonists to bacterial cell surface lectins are expected to have therapeutic potential for a wide spectrum of bacterial infections, including: gastric (*Helicobacter pylori*), urinary tract (*E. coli*), pulmonary (*Klebsiella pneumoniae, Stretococcus pneumoniae, Mycoplasma pneumoniae*) and oral (*Actinomyces naeslundi* and *Actinomyces viscosus*) colonization/infection (S. N. Abraham, 1994, Bacterial Adhesins, in The Handbook of Immunopharmacology: Adhesion Molecules, C. D. Wegner, ed; B. J. Mann et al., 1991, Proc. Natl. Acad. Sci. 88, 3248–3252). A specific bacterial mediated disease state is *Pseudomonas aeruginosa* infection, the leading cause of morbidity and mortality in cystic fibrosis patients. The expectation that high affinity antagonists will have efficacy in treating *P. aeruginosa* infection is based on three observations. First, a bacterial cell surface, GalNAcβ1-4Gal binding lectin mediates infection by adherence to asialogangliosides (αGM1 and αGM2) of pulmonary epithelium (L. Imundo et al., 1995, Proc. Natl. Acad. Sci 92, 3019–3023). Second, in vitro, the binding of *P. aeruginosa* is competed by the gangliosides' tetrasaccharide moiety, Galβ1-3GalNAcβ1-4Galβ1-4Glc. Third, in vivo, instillation of antibodies to Pseudomonas surface antigens can prevent lung and pleural damage (J. F. Pittet et al., 1993, J. Clin. Invest. 92, 1221–1228).

Non-bacterial microbes that utilize lectins to initiate infection include *Entamoeba histalytica* (a Gal specific lectin that mediates adhesion to intestinal muscosa; W. A. Petri, Jr., 1991, AMS News 57:299–306) and *Plasmodium faciparum* (a lectin specific for the terminal Neu5Ac(a2-3) Gal of glycophorin A of erthrocytes; P. A. Orlandi et al., 1992. J. Cell Biol. 116:901–909). Antagonists to these lectins are potential theraputics for dysentary and malaria.

Toxins are another class of proteins that recognize exogenous carbohydrates (K-A Karlsson, 1989, Ann. Rev. Biochem. 58:309–350). Toxins are complex, two domain molecules, composed of a functional and a cell recognition/ adhesion domain. The adhesion domain is often a lectin (ie., bacterial toxins: pertussis toxin, cholera toxin, heat labile toxin, verotoxin and tetanus toxin; plant toxins: ricin and abrin). Lectin antagonists are expected to prevent these toxins from binding their target cells and consequently to be useful as antitoxins.

There are still other conditions for which the role of lectins is currently speculative. For example, genetic mutations result in reduced levels of the serum mannose-binding protein (MBP). Infants who have insufficient levels of this lectin suffer from severe infections, but adults do not. The high frequency of mutations in both oriental and caucasian populations suggests a condition may exist in which low levels of serum mannose-binding protein are advantageous. Rheumatoid arthritus (RA) may be such a condition. The severity of RA is correlated with an increase in IgG antibodies lacking terminal galactose residues on Fc region carbohydrates (A. Young et al., 1991, Arth. Rheum. 34, 1425–1429; I. M. Roitt et al., 1988, J. Autoimm. 1, 499–506). Unlike their normal counterpart, these gal-deficient carbohydrates are substrates for MBP. MBP/IgG immunocomplexes may contribute to host tissue damage through complement activation. Similarly, the eosinophil basic protein is cytotoxic. If the cytotoxicity is mediated by the lectin activity of this protein, then a lectin antagonist may have therapeutic applications in treating eosinophil mediated lung damage.

Lectin antagonists may also be useful as imaging agents or diagnostics. For example, E-selectin antagonists may be used to image inflamed endothelium. Similarly antagonists to specific serum lectins, ie. mannose-binding protein, may also be useful in quantitating protein levels.

Lectins are often complex, multi-domain, multimeric proteins. However, the carbohydrate-binding activity of mammalian lectins is normally the property of a carbohydrate recognition domain or CRD. The CRDs of mammalian lectins fall into three phylogenetically conserved classes: C-type, S-type and P-type (K. Drickamer and M. E. Taylor, 1993, Annu. Rev. Cell Biol. 9, 237–264). C-type lectins require $Ca^{++}$ for ligand binding, are extracellular membrane and soluble proteins and, as a class, bind a variety of carbohydrates. S-type lectins are most active under reducing conditions, occur both intra- and extracellularly, bind β-galactosides and do not require $Ca^{++}$. P-type lectins bind mannose 6-phosphate as their primary ligand.

Although lectin specificity is usually expressed in terms of monosaccharides and/or oligosacchrides (ie., MBP binds mannose, fucose and N-acetylglucosamine), the affinity for monosaccharides is weak. The dissociation constants for monomeric saccharides are typically in the millimolar range (Y. C. Lee, 1992, FASEB J. 6:3193–3200; G. D. Glick et al., 1991, J Biol. Chem. 266:23660–23669; Y. Nagata and M. M. Burger, 1974, J. Biol. Chem. 249:116–3122).

Co-crystals of MBP complexed with mannose oligomers offer insight into the molecular limitations on affinity and specificity of C-type lectins (W. I. Weis et al., 1992, Nature 360:127–134; K. Drickamer, 1993, Biochem. Soc. Trans. 21:456–459). The 3- and 4-hydroxyl groups of mannose form coordination bonds with bound $Ca^{++}$ ion #2 and hydrogen bonds with glutamic acid (185 and 193) and asparagine (187 and 206). The limited contacts between the CRD and bound sugar are consistent with its spectrum of monosaccharide binding; N-acetylglucosamine has equatorial 3- and 4-hydroxyls while fucose has similarly configured hydroxyls at the 2 and 3 positions.

The affinity of the mannose-binding protein and other lectins for their natural ligands is greater than that for monosaccharides. Increased specificity and affinity can be accomplished by establishing additional contacts between a protein and its ligand (K. Drickamer, 1993, supra) either by 1) additional contacts with the terminal sugar (ie., chicken hepatic lectin binds N-acetylglucose amine with greater affinity than mannose or fucose suggesting interaction with the 2-substituent); 2) clustering of CRDs for binding complex oligosaccharides (ie., the mammalian asialylglycoprotein receptor); 3) interactions with additional saccharide residues (ie., the lectin domain of selectins appears to interact with two residues of the tetrasaccharide sialyl-Lewis$^x$: with the charged terminal residue, sialic acid, and with the fucose residue; wheat germ agglutinin appears to interact with all three residues of trimers of N-acetylglcosamine); or by 4) contacts with a non-carbohydrate portion of a glyco-protein.

The low affinity of lectins for mono- and oligo-saccharides presents major difficulties in developing high affinity antagonists that may be useful theraputics. Approaches that have been used to develop antagonists are similar to those that occur in nature: 1) addition or modification of substituents to increase the number of interactions; and 2) multimerization of simple ligands.

The first approach has had limited success. For example, homologues of sialic acid have been analysed for affinity to influenza virus hemagglutinin (S. J. Watowich et al. 1994, Structure 2:719–731). The dissociation constants of the best analogues are 30 to 300 μM which is only 10 to 100-fold better than the standard monosaccharide.

Modifications of carbohydrate ligands to the selectins have also had limited success. In static ELISA competition assays, sialyl-Lewis$^a$ and sialyl-Lewis$^x$ have $IC_{50}$s of 220 μM and 750 μM, respectively, for the the inhibition of the binding of an E-selectin/IgG chimera to immobilized sialyl-Lewis$^x$ (R. M. Nelson et al., 1993, J. Clin. Invest. 91, 1157–1166). The $IC_{50}$ of a sialyl-Lewis$^a$ derivative (addition of an aliphatic aglycone to the GlcNAc and replacement of the N-acetyl with an $NH_2$ group) improved 10-fold to 21 μM. Similarly, removal of the N-acetyl from sialyl-Lewis$_x$ improves inhibition in an assay dependent manner (C. Foxall et al., 1992, J. Cell Biol. 117, 895–902; S. A. DeFrees et al, 1993, J. Am. Chem. Soc. 115, 7549–75500.

The second approach, multimerization of simple ligands, can lead to dramatic improvements in affinity for lectins that bind complex carbohydrates (Y. C. Lee, supra). On the other hand, the approach does not show great enhancement for lectins that bind simple oligosaccharides; dimerizing sialyl-Lewis$^x$, a minimal carbohydrate ligand for E-selectin, improves inhibition approximately 5-fold (S. A. DeFrees et al., supra).

An alternative approach is to design compounds that are chemically unrelated to the natural ligand. In the static ELISA competition assays inositol polyanions inhibit L- and P-selectin binding with $IC_{50}$S that range from 1.4 μM to 2.8 mM (O. Cecconi et al., 1994, J. Biol. Chem. 269, 15060–15066). Synthetic oligopeptides, based on selectin amino acid sequences, inhibit neutrophil binding to immobilized P-selectin with $IC_{50}$s ranging from 50 μM to 1 mM (J-G Geng et al., 1992, J. of Biol. Chem. 267, 19846–19853).

Lectins are nearly ideal targets for isolation of antagonists by SELEX technology described below. The reason is that oligonucleotide ligands that are bound to the carbohydrate binding site can be specifically eluted with the relevant sugar(s). Oligonucleotide ligands with affinities that are several orders of magnitude greater than that of the competing sugar can be obtained by the appropriate manipulation of the RNA to competitor ratio. Since the carbohydrate binding site is the active site of a lectin, essentially all ligands isolated by this procedure will be antagonists. In addition, these SELEX ligands will exhibit much greater specifity than monomeric and oligomeric saccharides.

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Nucleic Acid Ligands", now U.S. Pat. No. 5,270,163 (see also PCT/US91/04078), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", describes the use of SELEX in conjunction with gel electrophoresis to select nucleic acid molecules with specific structural characteristics, such as bent DNA. U.S. patent application Ser. No. 07/964,624, filed Oct. 21, 1992, entitled "Methods of Producing Nucleic Acid Ligands", now U.S. Pat. No. 5,496,938, describes methods for obtaining improved nucleic acid ligands after SELEX has been performed. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", describes a SELEX-based method which achieves highly efficient partitioning between oligonucleotides having high and low affinity for a target molecule. U.S. patent application Ser. No. 08/400, 440, filed Mar. 8, 1995, entitled "Systematic Evolution of Ligands by EXponential Enrichment: Chemi-SELEX", describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement", describes novel methods for making 2'-modified nucleosides.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX", respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

The present invention applies the SELEX methodology to obtain nucleic acid ligands to lectin targets. Lectin targets, or lectins, include all the non-enzymatic carbohydrate-binding proteins of non-immune origin, which include, but are not limited to, those described above.

Specifically, high affinity nucleic acid ligands to the GlcNAc binding lectin, wheat germ agglutinin of Triticum vulgare have been isolated. For the purposes of the invention the terms wheat germ agglutinin, wheat germ lectin and WGA are used interchangeably. Wheat germ agglutinin (WGA) is widely used for isolation, purification and structural studies of glyco-conjugates.

As outlined above, the selectins are important anti-inflammatory targets. Antagonists to the selectins modulate extravasion of leukocytes at sites of inflammation and thereby reduce neutrophil caused host tissue damage. Using SELEX technology, isolated high affinity antagonists of L-selectin, E-selectin and P-selectin mediated adhesion are isolated.

BRIEF SUMMARY OF THE INVENTION

The present invention includes methods of identifying and producing nucleic acid ligands to lectins and the nucleic acid ligands so identified and produced. More particularly, nucleic acid ligands are provided that are capable of binding specifically to Wheat Germ Agglutinin (WGA), L-Selectin, E-selectin and P-selectin.

Further included in this invention is a method of identifying nucleic acid ligands and nucleic acid ligand sequences to lectins comprising the steps of (a) preparing a candidate mixture of nucleic acids, (b) partitioning between members of said candidate mixture on the basis of affinity to said lectin, and (c) amplifying the selected molecules to yield a mixture of nucleic acids enriched for nucleic acid sequences with a relatively higher affinity for binding to said lectin.

More specifically, the present invention includes the nucleic acid ligands to lectins identified according to the above-described method, including those ligands to Wheat Germ Agglutinin listed in Table II, and those ligands to L-selectin listed in Tables VIII and XII. Additionally, nucleic acid ligands to E-selectin, P-selectin and serum mannose binding protein are provided. Also included are nucleic acid ligands to lectins that are substantially homologous to any of the given ligands and that have substantially the same ability to bind lectins and antagonize the ability of the lectin to bind carbohydrates. Further included in this invention are nucleic acid ligands to lectins that have substantially the same structural form as the ligands presented herein and that have substantially the same ability to bind lectins and antagonize the ability of the lectin to bind carbohydrates.

The present invention also includes modified nucleotide sequences based on the nucleic acid ligands identified herein and mixtures of the same.

The present invention also includes the use of the nucleic acid ligands in therapeutic, prophylactic and diagnostic applications.

BRIEF DESCRIPTION OF THE FIGURES

FIG. 7 shows hairpin secondary structures for representative L-selectin 2'NH$_2$ RNA ligands: (a) F13.32 (SEQ. ID NO: 67), family I (b) 6.16 (SEQ. ID NO: 84), family III and (c) F14. 12 (SEQ. ID NO: 78), family II. Nucleotide sequence is in standard one letter code. Invariant nucleotides are in bold type. Nucleotides derived from fixed sequence are in lower case.

FIG. 10 shows the consensus hairpin secondary structures for family 1 ssDNA ligands to L-selectin. Nucleotide sequence is in standard one letter code. Invariant nucleotides are in bold type. The base pairs at highly variable positions are designated N-N'. To the right of the stem is a matrix showing the number of occurances of particular base pairs for the position in the stem that is on the same line.

DETAILED DESCRIPTION OF THE INVENTION

Figure 1A:
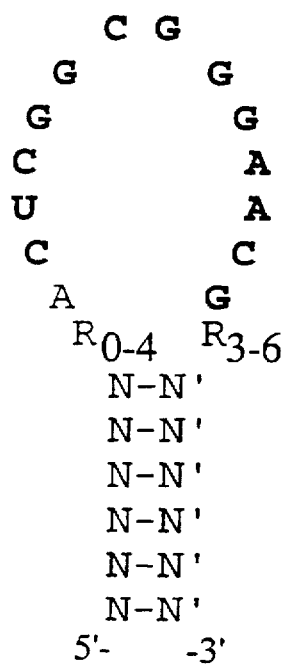
FIG. 1 shows consensus hairpin secondary structures for WGA 2'NH$_2$RNA ligands: (a) family 1, (b) family 2, and (c) family 3. Nucleotide sequence is in standard one letter code. Invariant nucleotides are in bold type. Nucleotides derived from fixed sequence are in lower case.

This application describes high-affinity nucleic acid ligands to lectins identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Nucleic Acid Ligands, now U.S. Patent No. 5,270, 163, (see also PCT/US91/04078). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 0.05–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of lectins. Specifically, the present invention describes the identification of nucleic acid ligands to Wheat Germ Agglutinin, and the Selectins, specifically, L-selectin, E-selectin and P-selectin. In the Example section below, the experimental parameters used to isolate and identify the nucleic acid ligands to Wheat Germ Agglutinin, L-selectin, E-selectin and P-selectin are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In the present invention, a SELEX experiment was performed in search of nucleic acid ligands with specific high affinity for Wheat Germ Agglutinin from a degenerate library containing 50 random positions (50N). This invention includes the specific nucleic acid ligands to Wheat Germ Agglutinin shown in Table II (SEQ ID NOS: 4–55), identified by the methods described in Examples 1 and 2. The scope of the ligands covered by this invention extends to all nucleic acid ligands of Wheat Germ Agglutinin, modified and unmodified, identified according to the SELEX procedure. More specifically, this invention includes nucleic acid sequences that are substantially homologous to the ligands shown in Table II. By substantially homologous it is meant a degree of primary sequence homology in excess of 70%, most preferably in excess of 80%. A review of the sequence homologies of the ligands of Wheat Germ Agglutinin shown in Table II shows that sequences with little or no primary homology may have substantially the same ability to bind Wheat Germ Agglutinin. For these reasons, this invention also includes nucleic acid ligands that have substantially the same ability to bind Wheat Germ Agglutinin as the nucleic acid ligands shown in Table II. Substantially the same ability to bind Wheat Germ Agglutinin means that the affinity is within a few orders of magnitude of the affinity of the ligands described herein. It is well within the skill of those of ordinary skill in the art to determine whether a given sequence—substantially homologous to those specifically described herein—has substantially the same ability to bind Wheat Germ Agglutinin.

In the present invention, a SELEX experiment was performed in search of nucleic acid ligands with specific high affinity for L-selectin from a degenerate library containing 40 random positions (40N). This invention includes the specific nucleic acid ligands to L-selectin shown in Tables VIII and XII (SEQ ID NOS: 67–117 and 129–167), identified by the methods described in Examples 7, 8, 13 and 14. The scope of the ligands covered by this invention extends to all nucleic acid ligands of L-selectin, modified and unmodified, identified according to the SELEX procedure. More specifically, this invention includes nucleic acid sequences that are substantially homologous to the ligands shown in Tables VIII and XII. By substantially homologous it is meant a degree of primary sequence homology in excess of 70%, most preferably in excess of 80%. A review of the sequence homologies of the ligands of L-selectin shown in Tables VIII and XII shows that sequences with little or no primary homology may have substantially the same ability to bind L-selectin. For these reasons, this invention also includes nucleic acid ligands that have substantially the same ability to bind L-selectin as the nucleic acid ligands shown in Tables VIII and XII. Substantially the same ability to bind L-selectin means that the affinity is within a few orders of magnitude of the affinity of the ligands described herein. It is well within the skill of those of ordinary skill in the art to determine whether a given sequence— substantially homologous to those specifically described herein—has substantially the same ability to bind L-selectin.

In the present invention, a SELEX experiment was performed in search of nucleic acid ligands with specific high affinity for E-selectin and P-selectin from a degenerate library containing 40 random positions (40N). This invention includes specific nucleic acid ligands to E-selectin and P-selectin identified by the methods described in Examples 19 and 20. The scope of the ligands covered by this invention extends to all nucleic acid ligands of E-selectin and P-selectin, modified and unmodified, identified according to the SELEX procedure.

This invention also includes the ligands as described above, wherein certain chemical modifications are made in order to increase the in vivo stability of the ligand or to enhance or mediate the delivery of the ligand. Examples of such modifications include chemical substitutions at the sugar and/ or phosphate and/or base positions of a given nucleic acid sequence. See, e.g., U.S. patent application Ser. No. 08/117,991, filed Sep. 9, 1993, entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process. Additionally, the nucleic acid ligands of the invention can be complexed with various other compounds, including but not limited to, lipophilic compounds or non-immunogenic, high molecular weight compounds. Lipophilic compounds include, but are not limited to, cholesterol, dialkyl glycerol, and diacyl glycerol. Non-immunogenic, high molecular weight compounds include, but are not limited to, polyethylene glycol, dextran, albumin and magnetite. This type of nucleic acid ligand complex is described in copending U.S. patent application Ser. Number 08/434,465, filed May 4, 1995, entitled "Nucleic Acid Ligand Complexes", which is herein incorporated by reference.

Well established animal models exist for many of the disease states which are candidates for selectin antagonist therapy. Models available for testing the efficacy of oligonucleotide selectin antagonists include:

1) mouse models for peritoneal inflammation (P. Pizcueta and F. W. Luscinskas, 1994, Am. J. Pathol. 145, 461–469), diabetes (A. C. Hanninen et al., 1992, J. Clin. Invest. 92, 2509–2515), lymphocyte trafficking (L. M. Bradley et al, 1994, J. Exp. Med. 2401–2406), glomerulonephritis (P. G. Tipping et al., 1994k Kidney Int. 46, 79–88), experimental allergic encephalomyelitis (J. M. Dopp et al., 1994, J. Neuroimmunol. 54:129–144), acute inflammation in human/ SCID mouse chimera (H.-C. Yan et al., 1994, J. Immunol. 152, 3053–3063), endotoxin-mediated inflammation (W. E. Sanders et al., 1992, Blood 80, 795 800);

2) rat models for acute lung injury (M. S. Milligan et al., 1994, J. Immunol. 152, 832–840), hind limb ischemia/ reperfusion injury (A. Seekamp et al., 1994, Am. J. Pathol 144, 592–598), remote lung injury (A. Seekamp et al., 1994, supra; D. L. Carden et al., 1993, J. Appl. Physiol 75, 2529–2543), neutrophil rolling on mesenteric venules (K. Ley et al., 1993, Blood 82, 132–1638), myocardial infarction ischemia reperfusion injury (D. Altavilla et al., 1994, Eur. J. Pharmacol. Environ. Toxicol. Pharmacol. 270, 45–51);

3) rabbit models for hemorrhagic shock (R. K. Winn et al., 1994, Am. J. Physiol. Heart Circ. Physiol. 267, H2391–H2397), ear ischemia reperfusion injury (D. Mihelcic et al., 1994, Bollod 84, 2333–2328 neutrophil rolling on mesenteric venules (A. M. Olofsson et al., Blood 84, 2749–2758), experimental meningitis (C. Granert et al., 1994, J. Clin. Invest. 93, 929–936); lung, peritoneal and subcutaneous bacterial infection (S. R. Sharer et al., 1993, J. Immunol. 151, 4982 4988), myocardial ischemia/repefusion (G. Montrucchio et al., 1989, Am. J. Physiol. 256, H1236–H1246), central nervous system ischemic injury (W. M. Clark et al., 1991, Stroke 22, 877–883);

4) cat models for myocardial infraction ischemia reperfusion injury (M. Buerke et al., 1994, J. Pharmacol. Exp. Ther. 271, 134–142);

5) dog models for myocardial infarction ischemia reperfusion injury (D. J. Lefer et al., 1994, Circulation 90, 2390–24011;

6) pig models for arthritis (F. Jamar et al., 1995, Radiology 194, 843–850);

7) rhesus monkey models for cutaneous inflammation (A. Silber et al., Lab. Invest. 70, 163–175);

8) cynomolgus monkey models for renal transplants (S.-L. Wee, 1991, Transplant. Prod. 23, 279–280); and 9) baboon models for dacron grafts (T. Palabrica et al., 1992, Nature 359, 848–851), septic, traumatic and hypovoemic shock (H. Redl et al., 1991, Am. J. Pathol. 139, 461–466).

The nucleic acid ligands to lectins described herein are useful as pharmaceuticals and as diagnostic reagents.

EXAMPLES

The following examples are illustrative of certain embodiments of the invention and are not to be construed as limiting the present invention in any way. Examples 1–6 describe identification and characterization of 2'NH$_2$RNA ligands to Wheat Germ Agglutinin. Examples 7–12 described identification and characterization of 2'NH$_2$RNA ligands to L-selectin. Examples 13–17 describe identification and characterization of ssDNA ligands to L-selectin. Example 18 describes identification of nucleic acid ligands to E-selectin. Example 19 describes identification of nucleic acid ligands to P-selectin.

Example 1

Nucleic Acid Ligands to Wheat Germ Agglutinin

Experimental Procedures

A) Materials

Wheat Germ Lectin (Triticum vulgare) Sepharose 6MB beads were purchased from Pharmacia Biotech. Free Wheat Germ Lectin (Triticum vulgare) and all other lectins were obtained from E Y Laboratories; methyl-α-D-mannopyranoside was from Calbiochem and N-acetyl-D-glucosamine, GlcNAc, and the trisaccharide N N' N'-triacetylchitotriose, (GlcNAc)$_3$, were purchased from Sigma Chemical Co. The 2'NH$_2$ modified CTP and UTP were prepared according to Pieken et. al. (1991, Science 253:314–317). DNA oligonucleotides were synthesized by Operon. All other reagents and chemicals were purchased from commercial sources. Unless otherwise indicated, experiments utilized Hanks' Balanced Salt Solutions (HBSS; 1.3 mM CaCl$_2$, 5.0 mM KCl, 0.3 mM KH$_2$PO$_4$, 0.5 mM MgCl$_2$.6H$_2$O, 0.4 mM MgSO$_4$.7H$_2$O, 138 mM NaCl, 4.0 mM NaHCO$_3$, 0.3 mM Na$_2$HPO4, 5.6 mM D-Glucose; GibcoBRL).

B) SELEX

The SELEX procedure is described in detail in U.S. Pat. No. 5,270,163 and elsewhere. In the wheat germ agglutinin SELEX experiment, the DNA template for the initial RNA pool contained 50 random nucleotides, flanked by N9 5' and 3' fixed regions (50N9) 5' gggaaaagcgaaucauacacaaga-50N-gcuccgccagagaccaaccgagaa 3' (SEQ ID NO: 1). All C and U have 2'NH$_2$ substituted for 2'OH for ribose. The primers for the PCR were the following: 5' Primer 5' taatacgactcactat-agggaaaagcgaatcatacacaaga 3' (SEQ ID NO: 2) and 3' Primer 5' ttctcggttggtctctggcggagc 3' (SEQ ID NO: 3). The fixed regions of the starting random pool include DNA primer annealing sites for PCR and cDNA synthesis as well as the consensus T7 promoter region to allow in vitro transcription. These single-stranded DNA molecules were converted into double-stranded transcribable templates by PCR amplification. PCR conditions were 50 mM KCl, 10 mM Tris-Cl, pH 8.3, 0.1% Triton X-100, 7.5 mM MgCl$_2$, 1 mM of each dATP, dCTP, dGTP, and dTTP, and 25 U/ml of Taq DNA polymerase. Transcription reactions contained 5 MM DNA template, 5 units/µl T7 RNA polymerase, 40 mM Tris-Cl (pH 8.0), 12 mM MgCl$_2$, 5 mM DTT, 1 mM spermidine, 0.002% Triton X-100, 4% PEG 8000, 2' mM each of 2'OH ATP, 2'OH GTP, 2'NH$_2$ CTP, 2'NH$_2$ UTP, and 0.31 mM α-$^{32}$P 2'OH ATP.

The strategy for partitioning WGA/RNA complexes from unbound RNA was 1) to incubate the RNA pool with WGA immobilized on sepharose beads; 2) to remove unbound RNA by extensive washing; and 3) to specifically elute RNA molecules bound at the carbohydrate binding site by incubating the washed beads in buffer containing high concentrations of (GlcNAc)$_3$. The SELEX protocol is outlined in Table 1.

The WGA density on Wheat Germ Lectin Sepharose 6MB beads is approximately 5 mg/ml of gel or 116 µM (manufacturer's specifications). After extensive washing in HBSS, the immobilized WGA was incubated with RNA at room temperature for 1 to 2 hours in a 2 ml siliconized column with constant rolling (Table I). Unbound RNA was removed by extensive washing with HBSS. Bound RNA was eluted as two fractions; first, nonspecifically eluted RNA was removed by incubating and washing with 10 mM methyl-α-D-mannopyranoside in HBSS (Table I; rounds 1–4) or with HBSS (Table I; rounds 5–11); second, specifically eluted RNA was removed by incubating and washing with 0.5 to 10 mM (GlcNAc)$_3$ in HBSS (Table I). The percentage of input RNA that was pecifically eluted is recorded in Table I.

The specifically eluted fraction was processed for use in the following round. Fractions eluted from immobilized WGA were heated at 90° C. for 5 minutes in 1% SDS, 2% β-mercaptoethanol and extracted with phenol/chloroform. RNA was reverse transcribed into cDNA by AMV reverse transcriptase at 48° C. for 60 min in 50 mM Tris-Cl pH (8.3), 60 mM NaCl, 6 mM Mg(OAc)$_2$, 10 mM DTT, 100 pmol DNA primer, 0.4 mM each of dNTPs, and 0.4 unit/µl AMV RT. PCR amplification of this cDNA resulted in approximately 500 pmol double-stranded DNA, transcripts of which were used to initiate the next round of SELEX.

D) Nitrocellulose Filter Partitioning

As described in SELEX Patent Applications, the nitrocellulose filter partitioning method was used to determine the affinity of RNA ligands for WGA and for other proteins. Filter discs (nitrocellulose/cellulose acetate mixed matrix, 0.45 µm pore size, Millipore; or pure nitrocellulose, 0.45 µm pore size, Bio-Rad) were placed on a vacuum manifold and washed with 4 ml of HBSS buffer under vacuum. Reaction mixtures, containing $^{32}$p labeled RNA pools and unlabeled WGA, were incubated in HBSS for 10 min at room temperature, filtered, and then immediately washed with 4 ml HBSS. The filters were air-dried and counted in a Beckman LS6500 liquid scintillation counter without fluor. WGA is a homodimer, molecular weight 43.2 kD, with 4 GlcNAc binding sites per dimer. For affinity calculations, we assume one RNA ligand binding site per monomer (two per dimer). The monomer concentration is defined as 2 times the dimer concentration. The equilibrium dissociation constant, $K_d$, for an RNA pool or specific ligand that binds monophasically is given by the equation $$K_d = [P_f][R_f]/[RP]$$

where, [Rf]=free RNA concentration

[Pf]=free WGA monomer concentration

[RP]=concentration of RNA/WGA monomer complexes $K_D$=dissociation constant

A rearrangement of this equation, in which the fraction of RNA bound at equilibrium is expressed as a function of the total concentration of the reactants, was used to calculate Kds of monophasic binding curves:

$$q=(P_T+R_T+K_D-((P_T+R_T+K_D)^2-4P_TR_T)^{1/2})$$

q=fraction of RNA bound

[$P_T$]=total WGA monomer concentration

[$R_T$]=total RNA concentration $K_D$S were determined by least square fitting of the data points using the graphics program Kaleidagraph (Synergy Software, Reading, Pa.).

E) Cloning and Sequencing

The sixth and eleventh round PCR products were re-amplified with primers which contain a BamHl or a EcoRl restriction endonuclease recognition site. Using these restriction sites the DNA sequences were inserted directionally into the pUC 18 vector. These recombinant plasmids were transformed into E. coli strain JM109 (Stratagene, La Jolla, Calif.). Plasmid DNA was prepared according to the alkaline hydrolysis method (Zhou et al., 1990 Biotechniques 8:172–173) and about 72 clones were sequenced using the Sequenase protocol (United States Biochemical Corporation, Cleveland, Ohio). The sequences are provided in Table II.

F) Competitive Binding Studies

Competitive binding experiments were performed to determine if RNA ligands and (GlcNAc)$_3$ bind the same site on WGA. A set of reaction mixtures containing $\alpha^{32}p$ labeled RNA ligand and unlabeled WGA, each at a fixed concentration (Table V), was incubated in HBSS for 15 min at room temperature with (GlcNAc)$_3$. Individual reaction mixtures were then incubated with a (GlcNAc)$_3$ dilution from a 2-fold dilution series for 15 minutes. The final (GlcNAc)$_3$ concentrations ranged from 7.8 µM to 8.0 mM (Table V). The reaction mixtures were filtered, processed and counted as described in "Nitrocellulose Filter Partitioning", paragraph D above.

Competition titration experiments were analyzed by the following equation to determine the concentration of free protein [P] as a function of the total concentration of competitor added, [$C_T$]:

$$0=[P](1+K_L[L_T]/(1+K_L[P])+K_C[C_T]/(1+K_C[P]))-P_T$$

where $L_T$ is the concentration of initial ligand, $K_L$ is the binding constant of species L to the protein (assuming 1:1 stiochiometry) and Kc is the binding constant of species C to the protein (assuming 1:1 stiochiometry). Since it is difficult to obtain a direct solution for equation 1, iteration to determine values of [P] to a precision of $1\times10^{-15}$ was used. Using these values of [P], the concentration of protein-ligand complex [PL] as a function of [$C_T$] was determined by the following equation:

$$[PL]=K_L[L_T][P]/(1+K_L[P])$$

Since the experimental data is expressed in terms of % [PL], the calculated concentration of [PL] was normalized by the initial concentration of [PLo] before addition of the competitor. ([PLo] was calculated using the quadratic solution for the standard binding equation for the conditions used (ref)). The maximum (M) and minimum (B) % [PL] was allowed to float during the analysis as shown in the following equation.

$$\% \, [PL]=[PL]/[PLo]*(M-B)+B$$

A non-linear least-squares fitting procedure was used as described by P. R. Bevington (1969) Data Reduction and Error Analysis for the Physical Sciences, McGraw-Hill publishers. The program used was originally written by Stanley J. Gill in MatLab and modified for competition analysis by Stanley C. Gill. The data were fit to equations 1–3 to obtain best fit parameters for $K_c$, M and B as a function of [$C_T$] while leaving $K_L$ and $P_T$ fixed.

G) Inhibition of WGA Agglutinating Activity

Agglutination is a readily observed consequence of the interaction of a lectin with cells and requires that individual lectin molecules crosslink two or more cells. Lectin mediated agglutination can be inhibited by sugars with appropriate specificity. Visual assay of the hemagglutinating activity of WGA and the inhibitory activity of RNA ligands, GlcNAc and (GlcNAc)$_3$ was made in Falcon round bottom 96 well microtiter plates, using sheep erythrocytes. Each well contained 54 µl of erythrocytes ($2.5\times10^8$ cells/ml) and 54 µl of test solution.

To titrate WGA agglutinating activity, each test solution contained a WGA dilution from a 4-fold dilution series. The final WGA concentrations ranged from 0.1 pM to 0.5 µM. For inhibition assays, the test solutions contained 80 nM WGA (monomer) and a dilution from a 4-fold dilution series of the designated inhibitor. Reaction mixtures were incubated at room temperature for 2 hours, after which time no changes were observed in the precipitation patterns of erythrocytes. These experiments were carried out in Gelatin Veronal Buffer (0.15 mM CaCl$_2$, 141 mM NaCl, 0.5 mM Mg Cl$_2$, 0.1% gelatin, 1.8 mM sodium barbial, and 3.1 mM barbituric acid, pH 7.3–7.4; Sigma #G-6514).

In the absence of agglutination, erythrocytes settle as a compact pellet. Agglutinated cells form a more diffuse pellet. Consequently, in visual tests, the diameter of the pellet is diagnostic for agglutination. The inhibition experiments included positive and negative controls for agglutination and appropriate controls to show that the inhibitors alone did not alter the normal precipitation pattern.

Example 2

RNA Ligands to WGA

A. SELEX

The starting RNA library for SELEX, randomized 50N9 (SEQ ID NO: 1), contained approximately $2\times10^{15}$ molecules (2 nmol RNA). The SELEX protocol is outlined in Table I. Binding of randomized RNA to WGA is undetectable at 36 µm WGA monomer. The dissociation constant of this interaction is estimated to be >4 mM.

The percentage of input RNA eluted by (GlcNAc)$_3$ increased from 0.05% in the first round, to 28.5% in round 5 (Table I). The bulk $K_d$ of round 5 RNA was 600 nM (Table I). Since an additional increase in specifically eluted RNA was not observed in round 6a (Table I), round 6 was repeated (Table I, round 6b) with two modifications to increase the stringency of selection: the volume of gel, and hence the mass of WGA, was reduced ten fold; and RNA was specifically eluted with increasing concentrations of (GlcNAc)$_3$, in stepwise fashion, with only the last eluted RNA processed for the following round. The percentage of specifically eluted RNA increased from 5.7% in round 6b to 21.4% in round 8, with continued improvement in the bulk $K_d$ (260 nM, round 8 RNA, Table I).

For rounds 9 through 11, the WGA mass was again reduced ten fold to further increase stringency. The $K_d$ of round 11 RNA was 68 nM. Sequencing of the bulk starting RNA pool and sixth and eleventh round RNA revealed some nonrandomness in the variable region at the sixth round and increased nonrandomess at round eleven. To monitor the progess of SELEX. ligands were cloned and sequenced from round 6b and round 11. From each of the two rounds, 36 randomly picked clones were sequenced. Sequences were aligned manually and are shown in Table II.

B. RNA Sequences

From the sixth and eleventh rounds, respectively, 27 of 29 and 21 of 35 sequenced ligands were unique. The number before the "." in the ligand name indicates whether it was cloned from the round 6 or round 11 pool. Only a portion of the entire clone is shown in Table II (SEQ ID NOS: 4–55). The entire evolved random region is shown in upper case letters. Any portion of the fixed region is shown in lower case letters. By definition, each clone includes both the evolved sequence and the associated fixed region, unless specifically stated otherwise. A unique sequence is operationally defined as one that differs from all others by three or more nucleotides. In Table II. ligands sequences are shown in standard single letter code (Cornish-Bowden, 1985 NAR 13:3021-3030). Sequences that were isolated more than once are indicated by the parenthetical number. (n), forllowing the ligand isolate number. These clones fall into nine sequence families (1–9) and a group of unrelated sequences (Orphans).

The distribution of families from round six to eleven provides a clear illustration of the appearance and disappearnce of ligand families in response to increased selective pressure (Table II). Family 3, predominant (11/29 ligands) in round 6, has nearly disappeared (2/35 ) by round 11. Similarly, minor familes 6 through 9 virtually disappear. In constrast, only one (family 1) of round eleven's predominant families (1, 2, 4 and 5) was detected in round six. The appearance and disappearance of families roughly correlates with their binding affinities.

Alignment (Table II) defines consensus sequences for families 1–4 and 6–9 (SEQ ID NOS: 56–63). The consensus sequences of families 1–3 are long (20, 16 and 16, respectively) and very highly conserved. The consensus sequences of families 1 and 2 contain two sequences in common: the trinucleotide TCG and the pentanucleotide ACGAA. A related tetranucleotide, AACG, occurs in family 3. The variation in position of the consensus sequences within the variable regions indicates that the ligands do not require a specific sequence from either the 5' or 3' fixed region.

The consensus sequences of family 1 and 2 are flanked by complementary sequences 5 or more nucleotides in length. These complementary sequences are not conserved and the majority include minor discontinuities. Family 3 also exhibits flanking complementary sequences. but these are more variable in length and structure and utilize two nucleotide pairs of conserved sequence.

Confidence in the family 4 consensus sequence (Table II) is limited by the small number of ligands, the variability of spacing and the high G content. The pentanucleotide, RCTGG, also occurs in families 5 and 8. Ligands of family 5 show other sequence similarities to those of family 4, especially to ligand 11.28.

C. Affinities

The dissociation constants for representative members of families 1–9 and orphan ligands were determined by nitrocellulose filter binding experiments and are listed in Table III. These calculations assume one RNA ligand binding site per WGA monomer. At the highest WGA concentration tested (36 µM WGA monomer), binding of random RNA is not observed. indicating a $K_d$ at least 100-fold higher than the protein concentration or >4 mM.

The data in Table III define several characteristics of ligand binding. First, RNA ligands to WGA bind monophasically. Second, the range of measured dissociation constants is 1.4 nM to 840 nM. Third, the binding for a number of ligands, most of which were sixth round isolates, was less than 5% at the highest WGA concentration tested. The dissociation constants of these ligands are estimated to be greater than 20 µM. Fourth, on average eleventh round isolates have higher affinity than those from the sixth round. Fifth, the SELEX probably was not taken to completion; the best ligand (11.20)(SEQ ID NO: 40) is not the dominant species. Since the SELEX was arbitrarily stopped at the 11th round, it is not clear that 11.20 would be the ultimate winner. Sixth, even though the SELEX was not taken to completion, as expected, RNA ligands were isolated that bind WGA with much greater affinity than do mono- or oligosaccharides (ie.. the affinty of 11.20 is $5 \times 10^5$ greater than that of GlcNAc, Kd=760 µM, and 850 better than that of $(GlcNAc)_3$, Kd=12 µM; Y. Nagata and M. Burger, 1974. supra). This observation validates our contention that competitive elution allows the isolation of oligonucleotide ligands with affinities that are serveral orders of magnitude greater than that of the competing sugar.

In addition these data show that even under conditions of high target density, 116 pmole WGA dimer/µl of beads, it is possible to overcome avidity problems and recover ligands with nanomolar affinities. From the sixth to the eleventh round (Table II), in response to increased selective pressure as indicated by the improvent in bulk $K_d$ (Table I), sequence families with lower than average affinity (Table III) are eliminated from the pool.

Example 3

Specificitv of RNA Ligands

The affinity of WGA ligands 6.8, 11.20 and 11.24 (SEQ ID NOS: 13, 40, and 19) for GlcNAc binding lectins from *Ulex europaeus, Datura stramonium* and *Canavalia ensiformis* were determined by nitrocellulose partitioning. The results of this determination are shown in Table IV. The ligands are highly specific for WGA. For example, the affinity of ligand 11.20 for WGA is 1,500, 8,000 and >15,000 fold greater than it is for the *U. europaeus, D. stramonium* and *C. ensiformis* lectins, respectively. The 8,000 fold difference in affinity for ligand 11.20 exhibited by *T. vulgare* and *D. stramonium* compares to a 3 to 10 fold difference in their affinity for oligomers of GlcNAc and validates our contention that competitive elution allows selection of oligonucleotide ligands with much greater specificty than monomeric and oligomeric saccharides (J. F. Crowley et al., 1984, Arch. Biochem. and Biophys. 231:524–533; Y. Nagata and M. Burger, 1974, supra; J-P. Privat et al., FEBS Letters 46:229–232).

Example 4

Competitive Binding Studies

If an RNA ligand and a carbohydrate bind a common site, then binding of the RNA ligand is expected to be competitively inhibited by the carbohydrate. Furthermore. if the oligonucleotide ligands bind exclusively to carbohydrate binding sites, inhibition is expected to be complete at high carbohydrate concentrations. In the experiments reported in Table V, dilutions of unlabeled $(GlcNAc)_3$, from a 2-fold dilution series, were added to three sets of binding reactions that contained WGA and an $\alpha$-$^{32}$p labeled RNA ligand (6.8, 11.20 or 11.24 (SEQ ID NOS: 13, 40 and 19); [RNA]$_{final}$= [WGA]$_{final}$=15 nM). After a 15 minute incubation at room temperature, the reactions were filtered and processed as in standard binding experiments.

Qualitatively, it is clear that RNA ligands bind only to sites at which (GlcNAc)$_3$ binds, since inhibition is complete at high (GlcNAc)$_3$ concentrations (Table V). These data do not rule out the possiblity that (GlcNAc)$_3$ binds one or more sites that are not bound by these RNA ligands.

Quantitatively, these data fit a simple model of competitive inhibition (Table V) and give estimates of 8.4, 10.9 and 19.4 μM for the Kd of (GlcNAc)$_3$. These estimates are in good agreement with literature values (12 μM @4° C., Nagata and Burger, 1974, supra; 11 μM @10.8° C., Van Landschoot et al., 1977, Eur. J. Biochem. 79:275-283; 50 μM, M. Monsigny et al., 1979, Eur J. Biochem. 98:39-45). These data confirm the assertion that competitive elution with a specific carbohydrate targets the lectin's carbohydrate binding site.

Example 5

Inhibition of WGA Agglutinating Activity

At 0.5 μM, RNA ligands 6.8 and 11.20 (SEQ ID NO: 13 and 40) completely inhibit WGA mediated agglutination of sheep erythrocytes (Table VI). Ligand 11.24 (SEQ ID NO: 19) is not as effective, showing only partial inhibition at 2 μM, the highest concentration tested (Table VI). (GlcNAc)$_3$ and GlcNAc completely inhibit agglutination at higher concentrations, 8 μM and 800 μM, respectively, (Table VI; Monsigny et al., supra). The inhibition of agglutination varifies the contention that ligands isolated by this procedure will be antagonists of lectin function. Inhibition also suggests that more than one RNA ligand is bound per WGA dimer, since agglutination is a function of multiple carbohydrate binding sites.

An alternative interpretation for the inhibition of agglutination is that charge repulsion prevents negatively charged WGA/RNA complexes from binding carbohydrates (a necessary condition for agglutination) on negatively charged cell surfaces. This explanation seems unlikely for two reasons. First, negatively charged oligonucleotide ligands selected against an immobilized purified protein are known to bind to the protein when it is presented in the context of a cell surface (see Example #10, L-selectin cell binding). Second, negatively charged (pI=4) succinylated WGA is as effective as native WGA (pI=8.5) in agglutinating erthrocytes (M. Monsigny et al., supra).

Example 6

Secondary Structure of High Affinity WGA Ligands

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequence are likely to be directly involved.

Figure 1B:
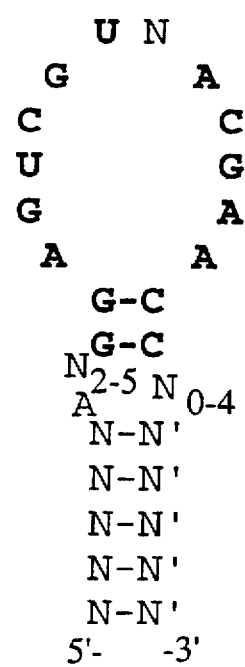
Figure 1C:
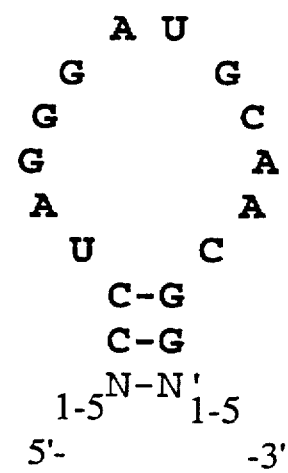

Comparative analyses of both family 1 and 2 sequences each yield a hairpin structure with a large, highly conserved loop (FIG. 1a and 1b). Interactions between loop nucleotides are likely but they are not defmed by these data. The stems of individual ligands vary in sequence, length and structure (ie., a variety of bulges and internal loops are allowed; Table II). Qualitatively it is clear that the stems are validated by Watson/Crick covariation and that by the rules of comparative analysis the stems are not directly involved in binding WGA. Family 3 can form a similar hairpin in which 2 pairs of conserved nucleotides are utilized in the stem (FIG. 1c).

If it is not possible to fold the ligands of a sequence family into homologous structures, their assignment to a single family is questionable. Both ligand 11.7, the dominant member of family 4, and ligand 11.28 can be folded into two plane G-quartets. However, this assignment is speculative: 1) 11.28 contains five GG dinucleotides and one GGGG tetranucleotide allowing other G-quartets; and 2) ligands 11.2 and 11.33 cannot form G-quartets. On the other hand, all ligands can form a hairpin with the conserved sequence GAGRFTNCRT in the loop. However, the conserved sequence RCTGGC (Table II) does not have a consistent role in these hairpins.

Multiple G-quartet structures are possible for Family 5. One of these resembles the ligand 11.7 G-quartet. No convincing hairpin structures are possible for ligand 11.20.

Example 7

2'NH$_2$RNA Ligands to Human L-Selectin

Experimental Procedures

A) Materials

LS-Rg is a chimeric protein in which the extracellular domain of human L-selectin is joined to the Fc domain of a human G2 immunoglobulin (Norgard et al., 1993, PNAS 90:1068-1072). ES-Rg, PS-Rg and CD22β-Rg are analogous constructs of E-selectin, P-selectin and CD22β joined to a human G1 immunoglobulin Fc domain (R. M. Nelson et al., 1993, supra; I. Stamenkovic et al., 1991, Cell 66, 1133-1144). Purified chimera were provided by A. Varki. Soluble P-selectin was purchased from R&D Systems. Protein A Sepharose 4 Fast Flow beads were purchased from Pharmacia Biotech. Anti-L-selectin monoclonal anitbodies: SK11 was obtained from Becton-Dickinson, San Jose, Calif.; DREG-56, an L-selectin specific monoclonal antibody, was purchased from Endogen, Cambridge, Mass. The 2' NH$_2$ modified CTP and UTP were prepared according to Pieken et. al. (1991, Science 253:314-317). DNA oligonucleotides were synthesized by Operon. All other reagents and chemicals were purchased from commercial sources. Unless otherwise indicated, experiments utilized HSMC buffer (1 mM CaCl$_2$, 1 mM MgCl$_2$, 150 mM NaCl, 20.0 mM HEPES, pH 7.4).

B) SELEX

The SELEX procedure is described in detail in U.S. Pat. No. 5,270,163 and elsewhere. The nucleotide sequence of the synthetic DNA template for the LS-Rg SELEX was randomized at 40 positions. This variable region was flanked by N7 5' and 3' fixed regions (40N7). 40N7 has the sequence 5' gggaggacgaugcgg-40N-cagacgacucgcccga 3' (SEQ ID NO: 64). All C and U have 2'NH$_2$ substituted for 2'OH on the ribose. The primers for the PCR were the following:

N7 5' Primer 5' taatacgactcactatagggaggacgatgcgg 3' (SEQ ID NO: 65)

N7 3' Primer 5' tcgggcgagtcgtcctg 3' (SEQ ID NO: 66)

The fixed regions include primer annealing sites for PCR and cDNA synthesis as well as a consensus T7 promoter to allow in vitro transcription. The initial RNA pool was made by first Klenow extending 1 nmole of synthetic single stranded DNA and then transcribing the resulting double stranded molecules with T7 RNA polymerase. Klenow extension conditions: 3.5 nmoles primer 5N7, 1.4 nmoles 40N7, 1X Klenow Buffer, 0.4 mM each of dATP, dCTP, dGTP and dTTP in a reaction volume of 1 ml.

For subsequent rounds, eluted RNA was the template for AMV reverse transcriptase mediated synthesis of single-stranded cDNA. These single-stranded DNA molecules were converted into double-stranded transcription templates by PCR amplification. PCR conditions were 50 mM KCl, 10 mM Tris-Cl, pH 8.3, 7.5 mM MgCl$_2$, 1 mM of each dATP, dCTP, dGTP, and dTTP, and 25 U/ml of Taq DNA polymerase. Transcription reactions contained 0.5 mM DNA template, 200 nM T7 RNA polymerase, 80 mM HEPES (pH 8.0), 12 mM MgCl$_2$, 5 mM DTT, 2 mM spermidine, 2 mM each of 2'OH ATP, 2'OH GTP, 2'NH$_2$ CTP, 2'NH$_2$UTP, and 250 nM α-$^{32}$P 2'OH ATP.

The strategy for partitioning LS-Rg/RNA complexes from unbound RNA is outlined in Tables VIIa and VIIb. First, the RNA pool was incubated with LS-Rg immobilized on protein A sepharose beads in HSMC buffer. Second, the unbound RNA was removed by extensive washing. Third, the RNA molecules bound at the carbohydrate binding site were specifically eluted by incubating the washed beads in HMSC buffer containing 5 mM EDTA in place of divalent cations. The 5 mM elution was followed by a non-specific 50 mM EDTA elution. LS-Rg was coupled to protein A sepharose beads according to the manufacturer's instructions (Pharmacia Biotech).

The 5 mM EDTA elution is a variation of a specific site elution strategy. Although it is not a priori as specific as elution by carbohydrate competition, it is a general strategy for C-type (calcium dependent binding) lectins and is a practical alternative when the cost and/or concentration of the required carbohydrate competitor is unreasonable (as is the case with sialyl-Lewis$_x$). This scheme is expected to be fairly specific for ligands that form bonds with the lectin's bound Ca$^{++}$ because the low EDTA concentration does not appreciably increase the buffer's ionic strength and the conformation of C-type lectins is only subtly altered in the absence of bound calcium (unpublished obervations cited by K. Drickamer, 1993, Biochem. Soc. Trans. 21:456–459).

In the initial SELEX rounds, which were performed at 4° C., the density of immobilized LS-Rg was 16.7 pmoles/μl of Protein A Sepharose 4 Fast Flow beads. In later rounds, the density of LS-Rg was reduced (Tables VIIa and VIIb), as needed, to increase the stringency of selection. At the seventh round, the SELEX was branched and continued in parallel at 4° C. (Table VIIa) and at room temperature (Table VIIb). Wash and elution buffers were equilibrated to the relevant incubation temperature. Beginning with the fifth round, SELEX was often done at more than one LS-Rg density. In each branch, the eluted material from only one LS-Rg density was carried forward.

Before each round, RNA was batch adsorbed to 100 μl of protein A sepharose beads for 1 hour in a 2 ml siliconized column. Unbound RNA and RNA eluted with minimal washing (two volumes) were combined and used for SELEX input material. For SELEX, extensively washed, immobilized LS-Rg was batch incubated with pre-adsorbed RNA for 1 to 2 hours in a 2 ml siliconized column with constant rocking. Unbound RNA was removed by extensive batch washing (200 to 500 μl HSMC/wash). Bound RNA was eluted as two fractions; first, bound RNA was eluted by incubating and washing columns with 5 mM EDTA in HSMC without divalent cations; second, the remaining elutable RNA was removed by incubating and/or washing with 50 mM EDTA in HSMC without divalents. The percentage of input RNA that was eluted is recorded in Tables VIIa and VIIb. In every round, an equal volume of protein A sepharose beads without LS-Rg was treated identically to the SELEX beads to determine background binding. All unadsorbed, wash and eluted fractions were counted in a Beckman LS6500 scintillation counter in order to monitor each round of SELEX.

The eluted fractions were processed for use in the following round (Tables VIIa and VIIb). After extracting with phenol/chloroform and precipitating with isopropanol/ethanol (1:1, v/v), the RNA was reverse transcribed into cDNA by AMV reverse transcriptase either 1) at 48° C. for 15 minutes and then 65° C. for 15 minutes or 2) at 37° C. and 48° C. for 15 minutes each, in 50 mM Tris-Cl pH (8.3), 60 mM NaCl, 6 mM Mg(OAc)$_2$, 10 mM DTT, 100 pmol DNA primer, 0.4 mM each of dNTPs, and 0.4 unit/μl AMV RT. Transcripts of the PCR product were used to initiate the next round of SELEX.

C) Nitrocellulose Filter Partitioning

As described in SELEX Patent Applications, the nitrocellulose filter partitioning method was used to determine the affinity of RNA ligands for LS-Rg and for other proteins. Filter discs (nitrocellulose/cellulose acetate mixed matrix, 0.45 um pore size, Millipore) were placed on a vacuum manifold and washed with 2 ml of HSMC buffer under vacuum. Reaction mixtures, containing $^{32}$p labeled RNA pools and unlabeled LS-Rg, were incubated in HSMC for 10–20 min at 4° C., room temperature or 37° C., filtered, and then immediately washed with 4 ml HSMC at the same temperature. The filters were air-dried and counted in a Beckman LS6500 liquid scintillation counter without fluor.

LS-Rg is a dimeric protein that is the expression product of a recombinant gene constructed by fusing the DNA sequence that encodes the extracellular domains of human L-selectin to the DNA that encodes a human IgG$_2$Fc region. For affinity calculations, we assume one RNA ligand binding site per LS-Rg monomer (two per dimer). The monomer concentration is defined as 2 times the LS-Rg dimer concentration. The equilibrium dissociation constant, K$_d$, for an RNA pool or specific ligand that binds monophasically is given by the equation $$Kd=[Pf][Rf]/[RP]$$

where, [Rf]=free RNA concentration

[Pf]=free LS-Rg monomer concentration

[RP]=concentration of RNA/LS-Rg complexes

KD=dissociation constant

A rearrangement of this equation, in which the fraction of RNA bound at equilibrium is expressed as a function of the total concentration of the reactants, was used to calculate Kds of monophasic binding curves:

$$q=(P_T+R_T+K_D-((P_T+R_T+K_D)^2-4\ P_TR_T)^{1/2})$$

q=fraction of RNA bound

[P$_T$]=2 x (total LS-Rg concentration)

[R$_T$]=total RNA concentration

Many ligands and evolved RNA pools yield biphasic binding curves. Biphasic binding can be described as the binding of two affinity species that are not in equilibrium. Biphasic binding data were evaluated with the equation $$q=2P_T+R_T+Kd_1+Kd_2-[(P_T+X_1R_1+K_{d1})^2-4P_TX_1R_T]^{1/2}-[(P_T+X_2R_T+K_{d2})^2-4P_TX_2R_T]^{1/2},$$

where X$_1$ and X$_2$ are the mole fractions of affinity species R$_1$ and R$_2$ and K$_{d1}$ and K$_{d2}$ are the corresponding dissociation constants. K$_D$S were determined by least square fitting K$_D$S were determined by least square fitting of the data points using the graphics program Kaleidagraph (Synergy Software, Reading, Pa.).

D) Cloning and Sequencing

Sixth, thirteenth (RT) and fourteenth (4° C.) round PCR products were re-amplified with primers which contain either a BamHI or a HinDII restriction endonuclease recognition site. Using these restriction sites, the DNA sequences were inserted directionally into the pUC9 vector. These recombinant plasmids were transformed into *E. coli* strain DH5α (Life Technologies, Gaithersburg, Md.). Plasmid DNA was prepared according to the alkaline hydrolysis method (PERFECTprep, 5'-3', Boulder, Colo.). Approximately 150 clones were sequenced using the Sequenase protocol (Amersham, Arlington Heights, Ill.). The resulting ligand sequences are shown in Table VIII.

E) Cell Binding Studies

The ability of evolved ligand pools and cloned ligands to bind to L-selectin presented in the context of a cell surface was tested in experiments with isolated human peripheral blood mononuclear cells (PBMCs). Whole blood, collected from normal volunteers, was anticoagulated with 5 mM EDTA. Six milliliters of blood were layered on a 6 ml Histopaque gradient in 15 ml polyproylene tube and centrifuged (700 g) at room temperature for 30 minutes. The mononuclear cell layer was collected, diluted in 10 ml of $Ca^{++}/Mg^{++}$-free DPBS (DPBS(−); Gibco 14190–029) and centrifuged (225 g) for 10 minutes at room temperature. Cell pellets from two gradients were combined, resuspended in 10 ml of DPBS(−) and recentrifuged as described above. These pellets were resuspended in 100 µl of SMHCK buffer supplemented with 1% BSA. Cells were counted in a hemocytometer, diluted to $2\times10^7$ cells/ml in SMHCK/1% BSA and immediately added to binding assays. Cell viability was monitored by trypan blue exclusion.

For cell binding assays, a constant number of cells were titrated with increasing concentrations of radiolabeled ligand. The test ligands were serially diluted in DPBS(−)/1% BSA to 2-times the desired final concentration approximately 10 minutes before use. Equal volumes (25 µl) of each ligand dilution and the cell suspension ($2\times10^7$ cells/ml) were added to 0.65 ml eppendorf tubes, gently vortexed and incubated on ice for 30 minutes. At 15 minutes the tubes were revortexed. The ligand/PBMC suspension was layered over 50 µl of ice cold phthalate oil (1:1=dinonyl:dibutyl phthalate) and microfuged (14,000 g) for 5 minutes at 4° C. Tubes were frozen in dry ice/ethanol, visible pellets amputated into scintillation vials and counted in Beckman LS6500 scintillation counter as described in Example 7, paragraph C.

The specificity of binding to PBMCs was tested by competition with the L-selectin specific blocking monoclonal antibody, DREG-56, while saturability of binding was tested by competition with unlabeled RNA. Experimental procedure and conditions were like those for PBMC binding experiments, except that the radiolabeled RNA ligand (final concentration 5 riM) was added to serial dilutions of the competitor before mixing with PBMCs.

G) Inhibition of Selectin Binding to sialyl-Lewis$^x$

The ability of evolved RNA pools or cloned ligands to inhibit the binding of LS-Rg to sialyl-Lewis$^x$ was tested in competive ELISA assays (C. Foxall et al., 1992, supra). For these assays, the wells of Corning (25801) 96 well microtiter plates were coated with 100 ng of a sialyl-Lewis$^x$/BSA conjugate, air dried overnight, washed with 300 µl of PBS(−) and then blocked with 1% BSA in SHMCK for 60 min at room temperature. RNA ligands were incubated with LS-Rg in SHMCK/1% BSA at room temperature for 15 min. After removal of the blocking solution, 50 µl of LS-Rg (10 nM) or a LS-Rg (10 nM)/RNA ligand mix was added to the coated, blocked wells and incubated at room temperature for 60 minutes. The binding solution was removed, wells were washed with 300 µl of PBS(−) and then probed with HRP conjugated anti-human IgG, at room temperature to quantitate LS-Rg binding. After a 30 minute incubation at room temperature in the dark with OPD peroxidase substrate (Sigma P9187), the extent of LS-Rg binding and percent inhibition was determined from the $OD_{450}$.

Example 8

RNA Ligands to LS-Rg

A. SELEX

The starting RNA pool for SELEX, randomized 40N7 (SEQ ID NO: 63), contained approximately $10^{15}$ molecules (1 nmol RNA). The SELEX protocol is outlined in Tables VIIa and VIIb. The dissociation constant of randomized RNA to LS-Rg is estimated to be approximately 10 µM. No difference was observed in the RNA elution profiles with 5 mM EDTA from SELEX and background beads for rounds 1 and 2, while the 50 mM elution produced a 2–3 fold excess over background (Table VIIa). The 50 mM eluted RNA from rounds 1 and 2 were amplified for the input material for rounds 2 and 3, respectively. Beginning in round 3, the 5 mM elution from SELEX beads was significantly higher than background and was processed for the next round's input RNA. The percentage of input RNA eluted by 5 mM EDTA increased from 0.5% in the first round to 8.4% in round 5 (Table VIIa). An additional increase in specifically eluted RNA from the 10 µM LS-Rg beads was not observed in round 6 (Table VIIa). To increase the stringency of selection, the density of immobilized LS-Rg was reduced ten fold in round 5 with further reductions in protein density at later rounds. The affinity of the selected pools rapidly increased and the pools gradually evolved biphasic binding characteristics.

Binding experiments with 6th round RNA revealed that the affinity of the evolving pool for L-selectin was temperature sensitive. Beginning with round 7, the SELEX was branched; one branch was continued at 4° C. (Table VIIa) while the other was conducted at room temperature (Table VIIb). Bulk sequencing of 6th, 13th (rm temp) and 14th (4° C.) RNA pools revealed noticeable non-randomness at round six and dramatic non-randomess at the later rounds. The 6th round RNA bound monophasically at 4° C. with a dissociation constant of approximately 40 nM, while the 13th and 14th round RNAs bound biphasically with high affinity Kds of approximately 700 pM. The molar fraction of the two pools that bound with high affinity were 24% and 65%, repectively. The binding of all tested pools required divalent cations. In the absence of divalent cations, the Kds of the 13th and 14th round pools increased to 45 nM and 480 nM, respectively (HSMC, minus $Ca^{++}/Mg^{++}$, plus 2 mM EDTA).

To monitor the progress of SELEX, ligands were cloned and sequenced from rounds 6, 13 (rm temp) and 14 (4° C.). Sequences were aligned manually and with the aid of a computer program that determines consensus sequences from frequently occuring local alignments.

B. RNA Sequences

In Table VIII, ligand sequences are shown in standard single letter code (Cornish-Bowden, 1985 NAR 13:3021–3030). The letter/number combination before the "." in the ligand name indicates whether it was cloned from the round 6, 13 or 14 pools. Only the evolved random region is shown in Table VIII. Any portion of the fixed region is shown in lower case letters. By definition, each clone includes both the evolved sequence and the associated fixed region, unless specifically stated otherwise. From the sixth, thirteenth and fourteenth rounds, respectively, 26 of 48, 8 of 24 and 9 of 70 sequenced ligands were unique. A unique sequence is operationally defined as one that differs from all others by three or more nucleotides. Sequences that were isolated more than once, are indicated by the parenthetical number, (n), following the ligand isolate number. These clones fall into thirteen sequence families (I–XIII) and a group of unrelated sequences (Orphans)(SEQ ID NOs: 67–117).

Two families, I and III, are defined by ligands from multiple lineages. Both families occur frequently in round 6, but only one family III ligand was identified in the final rounds. Six families (IV, V, VI, VII, VIII, and possibly II) are each defined by just two lineages which limits confidence in their consensus sequences. Five families (IX through XIII) are defined by a single lineage which precludes determination of consensus sequences.

Ligands from family II dominate the final rounds: 60/70 ligands in round 14 and 9/24 in round 13. Family II is represented by three mutational variations of a single sequence. One explanation for the recovery of a single lineage is that the ligand's information content is extremely high and was therefore represented by a unique species in the starting pool. Family II ligands were not detected in the sixth round which is consistent with a low frequency in the initial population. An alternative explanation is sampling error. Note that a sequence of questionable relationship was detected in the sixth round.

The best defined consensus sequences are those of family I, AUGUGUA (SEQ ID NO: 118), and of family III, AACAUGAAGUA (SEQ ID NO: 120), as shown in Table VIII. Family III has two additional, variably spaced sequences, AGUC and ARUUAG, that may be conserved. The tetranucleotide AUGW is found in the consensus sequence of families I, III, and VII and in families II, VIII and IX. If this sequence is significant, it suggests that the conserved sequences of ligands of family VIII are circularly permuted. The sequence AGAA is found in the consensus sequence of families IV and VI and in families X and XIII.

D. Affinities

The dissociation constants for representative ligands from rounds 13 and 14, including all orphans, were determined by nitrocellulose filter binding experiments and are listed in Table IX. These calculations assume two RNA ligand binding sites per chimera. The affinity of random RNA cannot be reliably determined but is estimated to be approximately 10 µM.

In general, ligands bind monophasically with dissociation constants ranging from 50 pM to 15 nM at 4° C. Some of the highest affinity ligands bind biphasically. Although ligands of families I, VII, X and orphan F14.70 bind about equally well at 4° C. and room temperature, in general the affinities decrease with increasing temperature. The observed affinities substantiate the contention that it is possible to isolate oligonucleotide ligands with affinities that are serveral orders of magnitude greater than that of carbohydrate ligands.

Example 9

Specificity of RNA Ligands

The affinity of L-selectin ligands to ES-Rg, PS-Rg and CD22β-Rg were determined by nitrocellulose partitioning. As indicated in Table X, the ligands are highly specific for L-selectin. In general, a ligand's affinity for ES-Rg is $10^3$-fold lower and that for PS-Rg is about $10^4$-fold less than for LS-Rg. Binding above background is not observed for CD22β-Rg at the highest protein concentration tested (660 nM), indicating that ligands do not bind the Fc domain of the chimeric constructs nor do they have affinity for the sialic acid binding site of an unrelated lectin. The specificity of oligonucleotide ligand binding contrasts sharply with the binding of cognate carbohydrates by the selectins and confirms the assertion that SELEX ligands will have greater specificity than carbohydrate ligands.

Example 10

Binding of RNA Ligands to PBMCs

Figure 2:
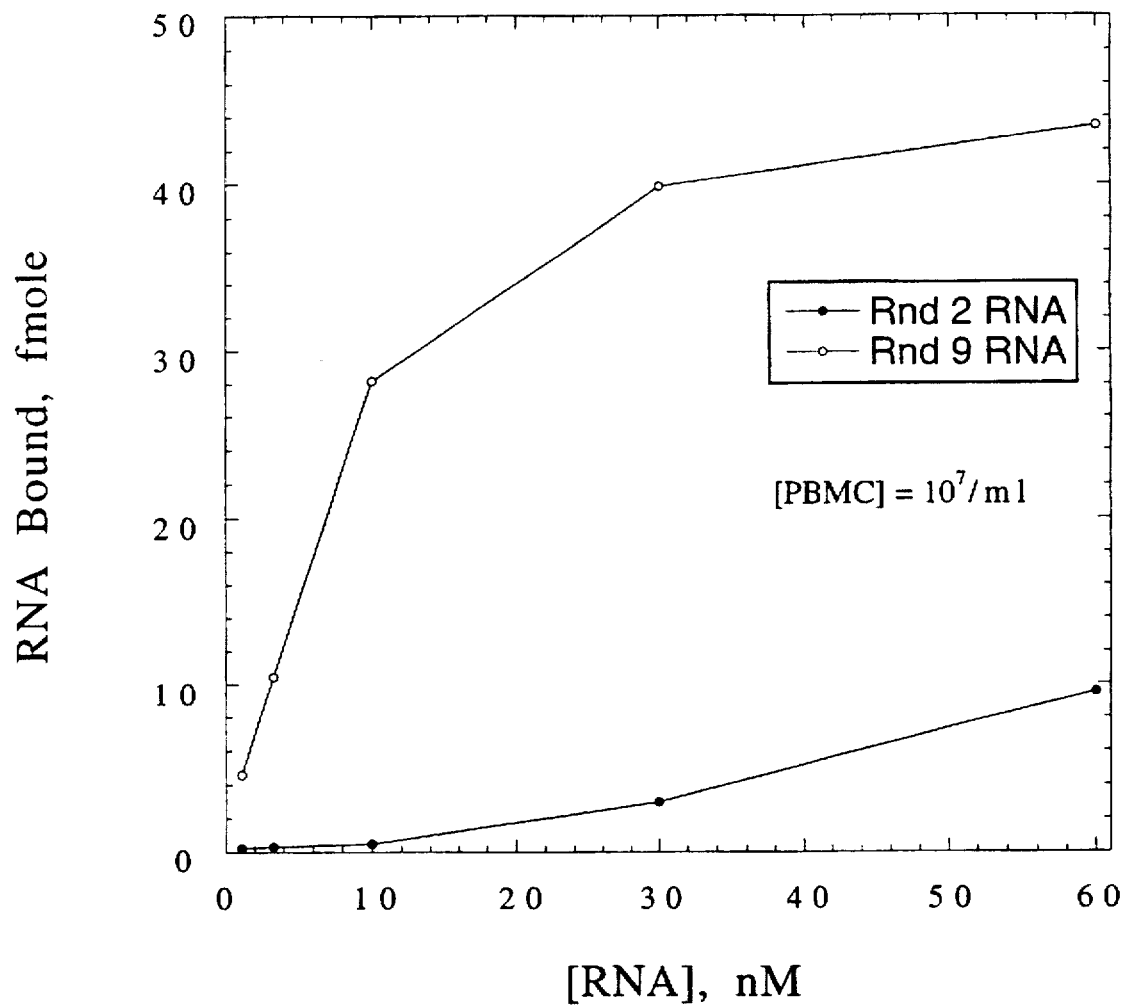
FIG. 2 shows binding curves for the L-selectin SELEX second and ninth round 2'NH$_2$RNA pools to peripheral blood lymphocytes (PBMCs).
Figure 3:
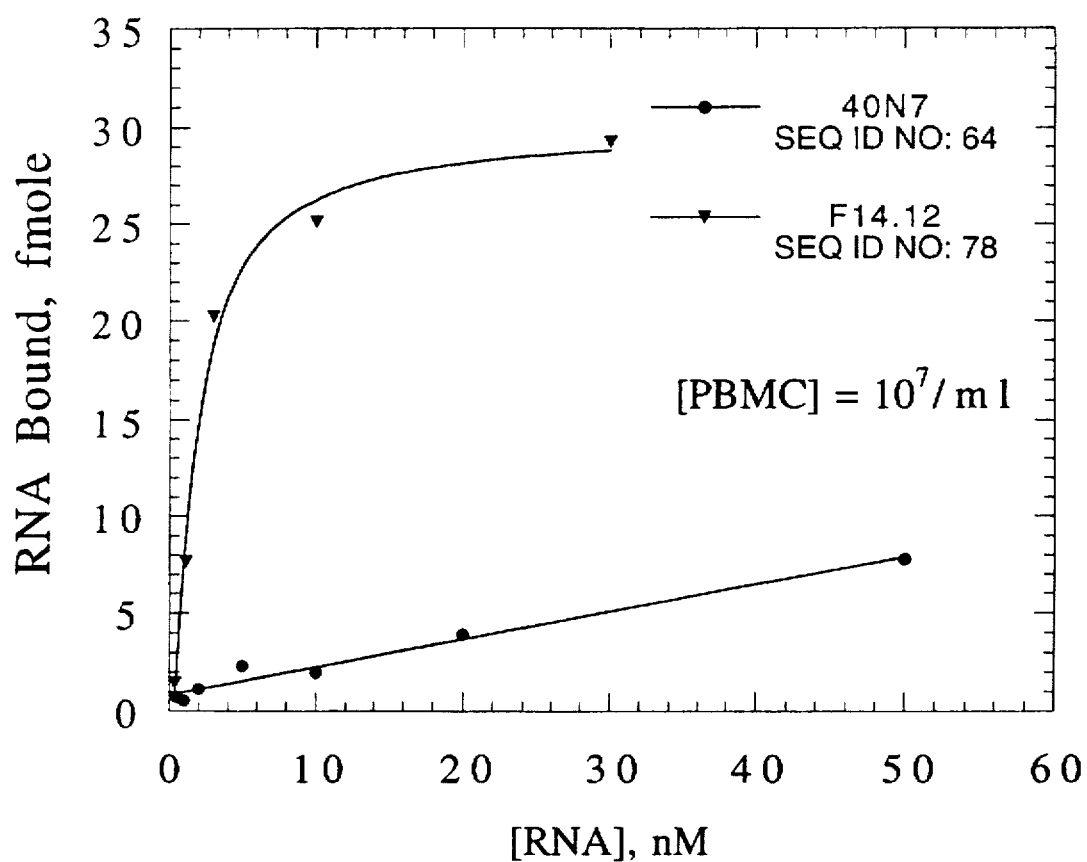
FIG. 3 shows binding curves for random 40N7 2'NH$_2$RNA (SEQ. ID NO: 64) and the cloned L-selectin ligand, F14.12 (SEQ. ID NO: 78), to peripheral blood lymphocytes (PBMC).
Figure 4:
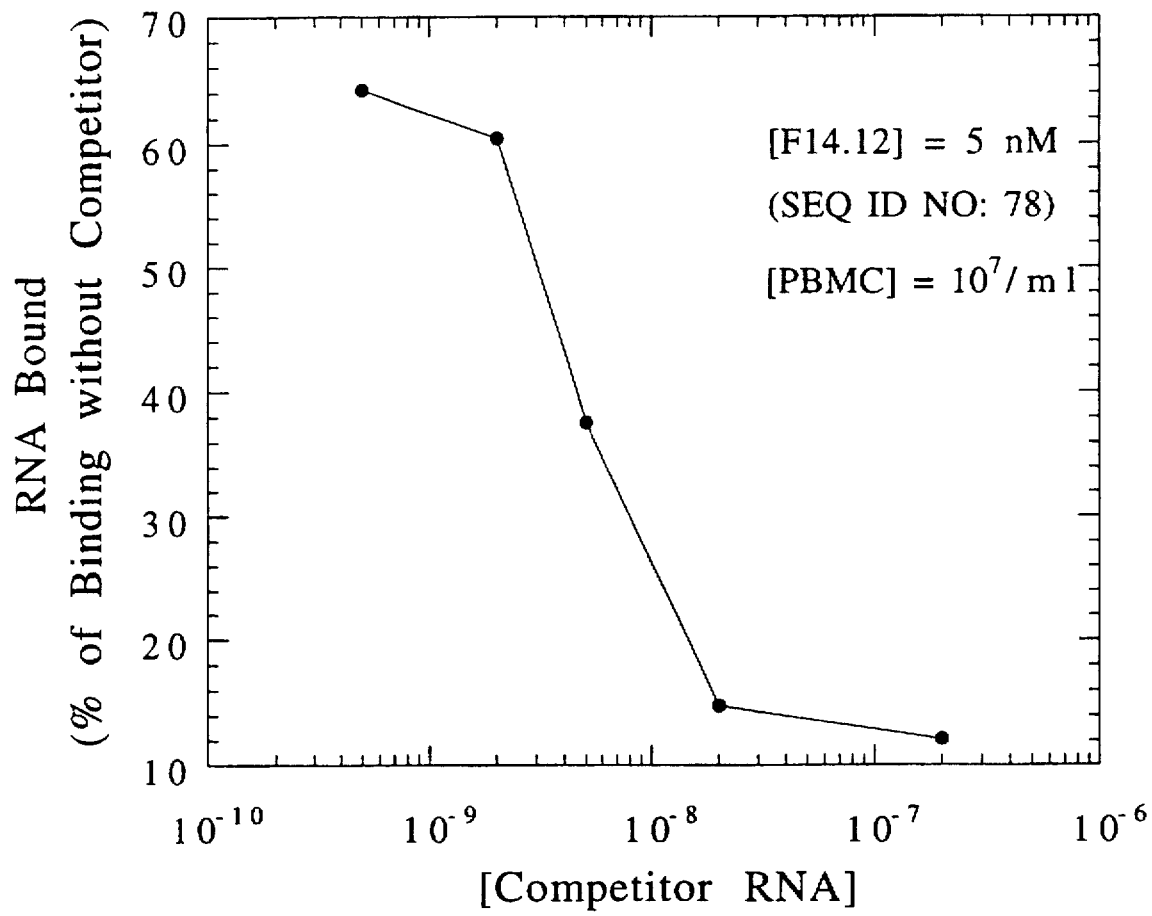
FIG. 4 shows the results of a competition experiment in which the binding of 5 nM $^{32}$P-labeled F14.12 (SEQ. ID NO: 78) to PBMCs (10$^7$/ml) is competed with increasing concentrations of unlabeled F14.12 (SEQ. ID NO: 78). RNA Bound equals 100 x (net counts bound in the presence of competitor/net counts bound in the absence of competitor).
Figure 5:
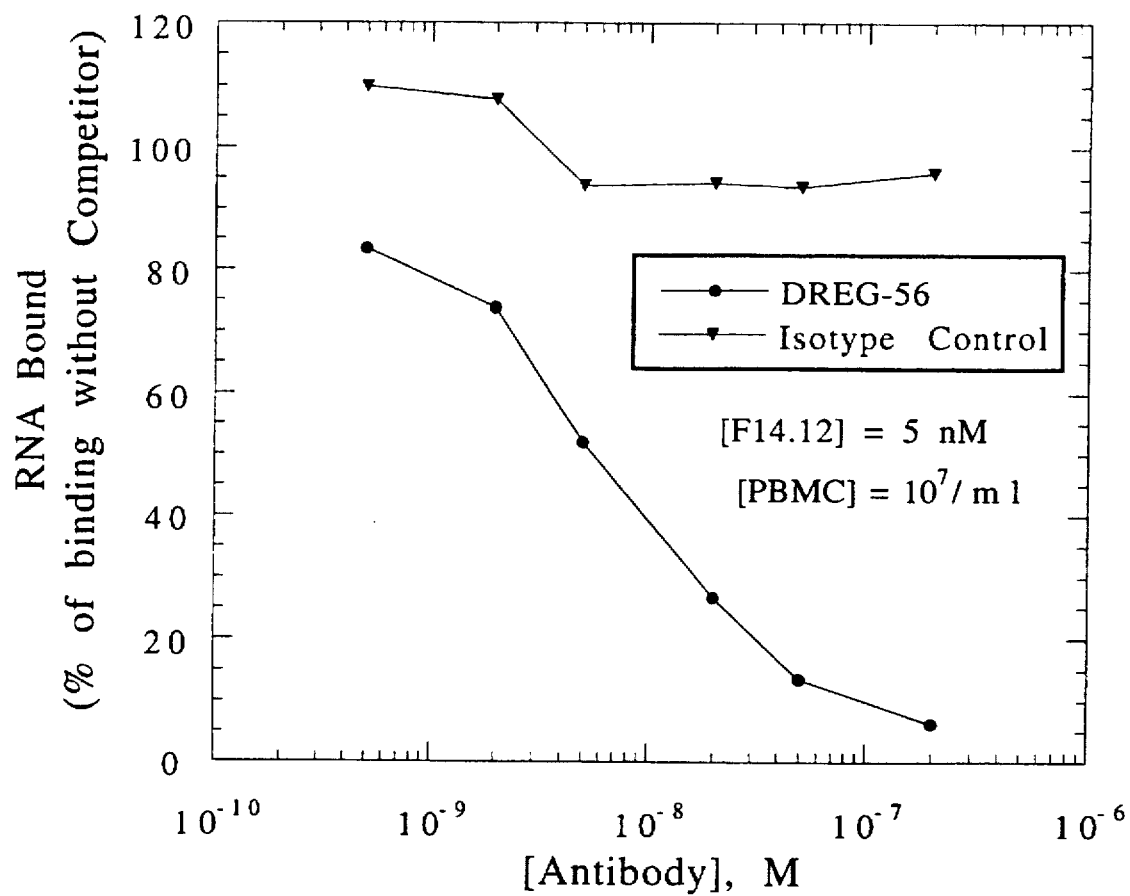
FIG. 5 shows the results of a competition experiment in which the binding of 5 nM $^{32}$P-labeled F14.12 (SEQ. ID NO: 78) to PBMCs (10$^7$/ml) is competed with increasing concentrations of the blocking monoclonal anti-L-selectin antibody, DREG-56, or an isotype matched, negative control antibody. RNA Bound equals 100 x (net counts bound in the presence of competitor/net counts bound in the absence of competitor).

Since the L-selectin ligands were isolated against purified, immobilized protein, it is essential to demonstrate that they bind L-selectin presented in the context of a cell surface. Comparison of 2nd and 9th round RNAs (FIG. 2) shows that the evolved (9th round) ligand pool binds isolated PBMCs with high affinity and, as expected for specific binding, in a saturable fashion. The binding of round 2 RNA appears to be non-saturable as is characteristic of non-specific binding. The cloned ligand, F14.12 (SEQ ID NO: 78), also binds in a saturable fashion with a dissociation constant of 1.3 nM, while random 40N7 (SEQ ID NO: 64) resembles round 2 RNA (FIG. 3). The saturability of binding is confirmed by the data in FIG. 4; >90% of 5 nM $^{32}$P-labeled F14. 12 RNA binding is competed by excess cold RNA. Specificity is demonstrated by the results in FIG. 5; binding of 5 nM $^{32}$P-labeled F14. 12 RNA is completely competed by the anti-L-selectin blocking monoclonal antibody, DREG-56, but is unaffected by an isotype-matched irrelevant antibody. These data validate the feasibilty of using immobilized, purified protein to isolate ligands against a cell surface protein and the binding specificity of F14.12 to L-selectin in the context of a cell surface.

Example 11

Inhibition of Binding to Sialy-Lewis$^x$

Oligonucleotide ligands, eluted by 2–5 mM EDTA, are expected to derive part of their binding energy from contacts with the lectin domain's bound $Ca^{++}$ and consequently, are expected to compete with sialyl-Lewis$^x$ for binding. The ability of ligand F14.12 (SEQ ID NO: 78) to inhibit LS-Rg binding to immobilized sialy-Lewis$_x$ was determined by competition ELISA assays. As expected, 4 mM EDTA reduced LS-Rg binding 7.4-fold, while 20 mM round 2 RNA did not inhibit LS-Rg binding. Carbohydrate binding is known to be $Ca^{++}$ dependent; the affinity of round 2 RNA is too low to bind 10 nM LS-Rg (Table VII).

Figure 6:
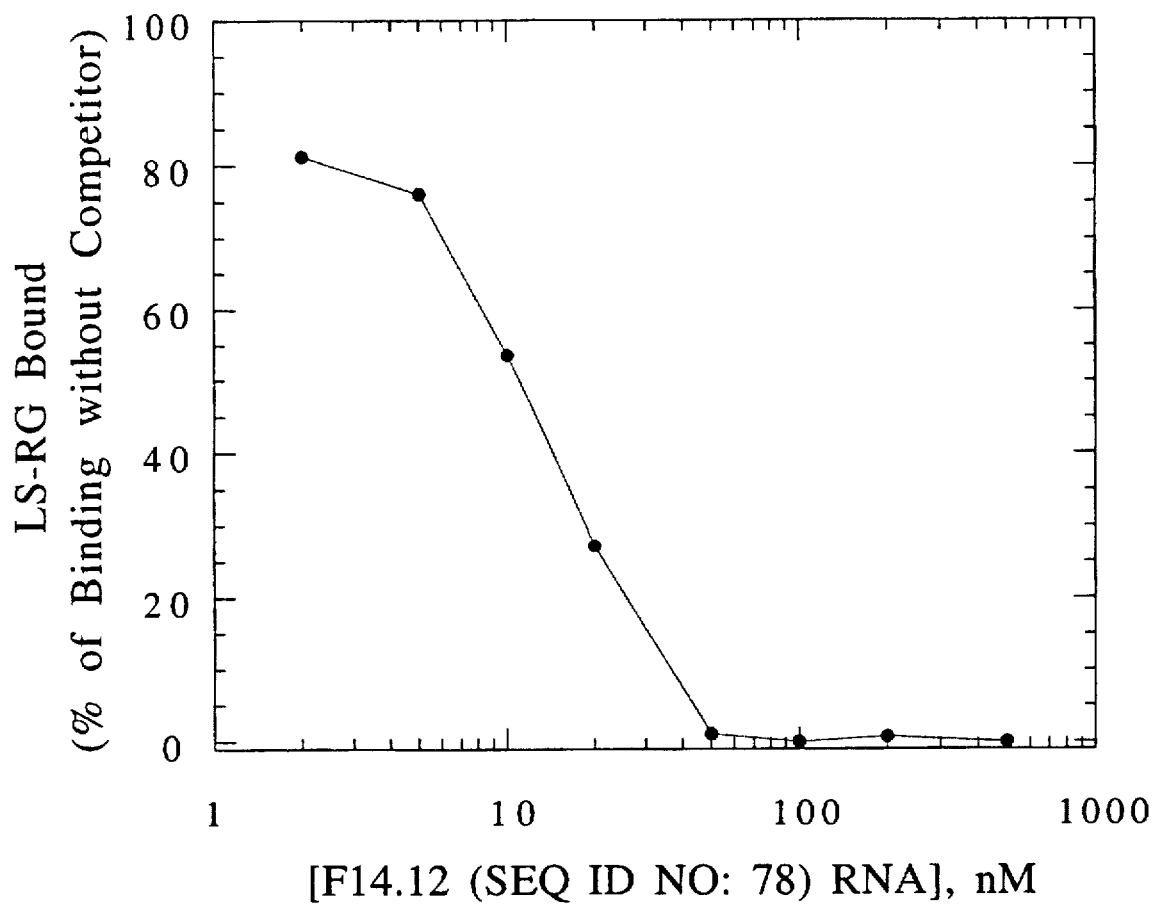
FIG. 6 shows the results of a competitive ELISA assay in which the binding of soluble LS-Rg to immobilized sialyl-Lewis$^x$/BSA conjugates is competed with increasing concentrations of unlabeled F14. 12 (SEQ. ID NO: 78). Binding of LS-Rg was monitored with an HRP conjugated anti-human IgG antibody. LS-Rg Bound equals 100 x (OD$_{450}$ in the presence of competitor)/(OD$_{450}$ in the absence of competitor). The observed OD$_{450}$ was corrected for nonspecific binding by subtracting the OD$_{450}$ in the absence of LS-Rg from the experimental values. In the absence of competitor the OD$_{450}$ was 0.324 and in the absence of LS-Rg 0.052. Binding of LS-Rg requires divalent cations; in the absence of competitor, replacement of Ca$^{++}$/Mg$^{++}$ with 4 mM EDTA reduced the OD$_{450}$ to 0.045.

In this assay F14.12 RNA inhibits LS-Rg binding in a concentration dependent manner with an $IC_{50}$ of about 10 nM (FIG. 6). Complete inhibition is observed at 50 nM F14.12. The observed inhibition is reasonable under the experimental conditions; the Kd of F14.12 at room temperature is about 1 nM (Table IX) and 10 nM LS-Rg is 20 nM binding sites. These data verify that RNA ligands compete with sialyl-Lewis$^x$ for LS-Rg binding and support the contention that low concentrations of EDTA specifically elute ligands that bind the lectin domain's carbohydrate binding site.

Example 12

Secondary Structure of High Affinity Ligands

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequence are likely to be directly involved.

Comparative analysis of the family I alignment suggests a hairpin structure in which the consensus sequence, AUGUGUGA, is contained within a variable size loop (FIG. 7a). The stem sequences are not conserved and may be either 5' or 3'-fixed or variable sequence. The one ligand that does not form a stem, F14.25 (SEQ ID NO: 73), has a significantly lower affinity than the other characterized ligands (Table IX).

The proposed structure for family III is also a hairpin with the conserved sequence, AACAUGAAGUA, contained within a variable length loop (FIG. 7b). The 5'-half of the stem is 5'-fixed sequence which may account in part for the less highly conserved sequence, AGUC.

Although there is no alignment data for family II, the sequence folds into a pseudoknot (FIG. 7c). Three attractive features of this model are 1) the helices stack on one another, 2) the structure utilizes only variable sequence and 3) the structure is compatible with the major variant sequences.

Example 13 ssDNA Ligands to Human L-Selectin

Experimental Procedures

A) Materials

Unless otherwise indicated, all materials used in the ssDNA SELEX against the L-selectin/IgG2 chimera, LS-Rg, were identical to those of Example 7. The buffer for SELEX experiments was 1 mM $CaCl_2$, 1 mM $MgC_{i2}$, 100 mM NaCl, 10.0 mM HEPES, pH 7.4. The buffer for all binding affinity experiments differed from the above in containing 125 mM NaCl, 5 mM KCl, and 20 mM HEPES, pH 7.4.

B) SELEX

The SELEX procedure is described in detail in U.S. Pat. No. 5,270,163 and elsewhere. The nucleotide sequence of the synthetic DNA template for the LS-Rg SELEX was randomized at 40 positions. This variable region was flanked by BH 5' and 3' fixed regions. The random DNA template was termed 4OBH (SEQ ID NO: 126) and had the following sequence:
5'-ctacctacgatctgactagc<40N>gcttactctcatgtagttcc-3'. The primers for the PCR were the following: 5' Primer: 5'-ctacctacgatctgactagc-3' (SEQ ID NO: 127) and 3' Primer: 5'-ajajaggaactacatgagagtaagc-3'; j=biotin (SEQ ID NO: 128). The fixed regions include primer annealing sites for PCR amplification. The initial DNA pool contained 500 pmoles of each of two types of single-stranded DNA: 1) synthetic ssDNA and 2) PCR amplified, ssDNA from 1 nmole of synthetic ssDNA template.

For subsequent rounds, eluted DNA was the template for PCR amplification. PCR conditions were 50 mM KCl, 10 mM Tris-Cl, pH 8.3, 7.5 mM $MgCl_2$, 1 mM of each dATP, dCTP, dGTP, and dTTP and 25 U/ml of the Stoffel fragment of Taq DNA polymerase. After PCR amplification, double stranded DNAs were end-labeled using $\gamma^{32}P$-ATP. Complementary strands were separated by electrophoresis through an 8% polyacrylamide/7M urea gel. Strand separation results from the molecular weight difference of the strands due to biotintylation of the 3' PCR primer. In the final rounds, DNA strands were separated prior to end labelling in order to achieve high specific activity. Eluted fractions were processed by ethanol precipitation.

The strategy for partitioning LS-Rg/RNA complexes from unbound RNA was as described in Example 7, paragraph B, except that 2 mM EDTA was utilized for specific elution. The SELEX strategy is outlined in Table XI.

C) Nitrocellulose Filter Partitioning

As described in SELEX Patent Applications and in Example 7, paragraph C, the nitrocellulose filter partitioning method was used to determine the affinity of RNA ligands for LS-Rg and for other proteins. For these experiments a Gibco BRL 96 well manifold was substituted for the 12 well Millipore manifold used in Example 7 and radioactivity was determined with a Fujix BAS 100 phosphorimager. Binding data were analysed as described in Example 7, paragraph C.

D) Cloning and Sequencing

Thirteenth and fifteenth round PCR products were re-amplified with primers which contain either a BamHI or a HinDIII restriction endonuclease recognition site. Approximately 140 ligands were cloned and sequenced using the procedures described in Example 7, paragraph D. The resulting sequences are shown in Table XII.

E) Cell Binding Studies

The ability of evolved ligand pools to bind to L-selectin presented in the context of a cell surface was tested in experiments with isolated human peripheral blood mononuclear cells (PBMCs) as described in Example 7, paragraph E.

Example 14 ssDNA Ligands to L-Selectin

A. SELEX

The starting ssDNA pool for SELEX, randomized 40BH (SEQ ID NO: 126), contained approximately $10^{15}$ molecules (1 nmol ssDNA). The dissociation constant of randomized ssDNA to LS-Rg is estimated to be approximately 10 µM. The SELEX protocol is outlined in Table XI.

The initial round of SELEX was performed at 4° C. with an LS-Rg density of 16.7 pmole/µl of protein A sepharose beads. Subsequent rounds were at room temperature except as noted in Table XI. The 2 mM EDTA elution was omitted from rounds 1–3. The signal to noise ratio of the 50 mM EDTA elution in these three rounds was 50, 12 and 25, respectively (Table XI). These DNAs were amplified for the input materials of rounds 2–4. Beginning with round 4, a 2 mM EDTA elution was added to the protocol. In this and all subsequent rounds, the 2 mM EDTA eluted DNA was amplified for the next round's input material.

To increase the stringency of selection, the density of immobilized LS-Rg was reduced ten fold in round 4 with further reductions in protein density at rounds 9, 11, 14 and 15 (Table XI). Under these conditions a rapid increase in the affinity of the selected pools was observed (Tables XI); at 4° C., the dissociation constant of round 7 ssDNA was 60 nM.

Binding experiments with 7th round DNA revealed that the affinity of the evolving pool for L-selectin was weakly temperature sensitive (Kds: 60 nM, 94 nM and 230 nM at 4° C., room temperature and 37° C., respectively). To enhance the selection of ligands that bind at physiological temperature, rounds 8 and 13 were performed at 37° C. Although still temperature sensitive, the affinity of round 15 ssDNA was optimal at room temperature (160 pM), with 3-fold higher Kds at 4° C. and 37° C.

Bulk sequencing of DNA pools indicates some non-randomness at round 5 and dramatic non-randomness at round 13. Ligands were cloned and sequenced from rounds 13 and 15. Sequences were aligned mannually and with the aid of a Nexstar computer program that determines consensus sequences from frequently occuring local alignments.

B. ssDNA Sequences

In Table XII, ligand sequences are shown in standard single letter code (Cornish-Bowden, 1985 NAR 13:3021–3030). Only the evolved random region is shown in Table XII. Any portion of the fixed region is shown in lower case letters. By definition, each clone includes both the evolved sequence and the associated fixed region, unless specifically stated otherwise. Thirty-nine of sixty seven sequenced ligands were unique. A unique sequence is operationally defined as one that differs from all others by three or more nucleotides. Sequences that were isolated more than once are indicated by the parenthetical number, (n), following the ligand isolate number. These clones fall into six families and a group of unrelated sequences or orphans (Table XII)(SEQ ID NOs: 129–167).

Family 1 is defined by 52 ligands from 28 lineages and has a well defined consensus sequence, TACAAG-GYGYTAVACGTA (SEQ ID NO: 168). The conservation of the CAAGG and ACG and their 6 nucleotide spacing is nearly absolute (Table XII). The consensus sequence is flanked by variable but complementary sequences that are 3 to 5 nucleotides in length. The statistical dominance of family 1 suggests that the properties of the bulk population are a reflection of those of family 1 ligands. We note that 2' ssDNA family I and 2' $NH_2$ family I share a common sequence, CAAGGCG and CAAGGYG, respectively.

Family 2 is respresented by a single sequence and is related to family 1. The ligand contains the absolutely conserved CAAGG and highly conserved ACG of family 1 although the spacing between the two elements is strikingly different (23 compared to 6 nucleotides).

Families 4–6 are each defined by a small number of ligands which limits confidence in their consensus sequence, while family 7 is defined by a single sequence which precludes determination of a consensus. Family 5 appears to contain two conserved sequences, AGGGT and RCACGAYACA, the positions of which are circularly permuted.

D. Affinities

The dissociation constants of representative ligands from Table XII are shown in Table XIII. These calculations assume two ssDNA ligand binding sites per chimera. The affinity of random ssDNA cannot be reliably determined but is estimated to be approximately 10 µM.

At room temperature, the dissociation constants range from 43 pM to 1.8 nM which is at least a $5\times10^3$ to $2\times10^5$ fold improvement over randomized ssDNA (Table XIII). At 37° C., the Kds range from 130 pM to 23 nM. The extent of temperature sensitivity varies from insensitive (ligands 122 and 127 (SEQ ID NO: 159 and 162)) to 80-fold (ligand 112 (SEQ ID NO: 135)). In general, among family 1 ligands the affinity of those from round 15 is greater than that of those from round 13. For the best ligands (208, 227, 230 and 233 (SEQ ID NOS: 133, 134, 132, and 146)), the difference in affinity at room temperature and 37° C. is about 4-fold.

The observed affinities of the evolved ssDNA ligand pools reaffirm our contention that it is possible to isolate oligonucleotide ligands with affinities that are several orders of magnitude greater than that of carbohydrate ligands.

Example 15

Specificity of ssDNA Ligands

The affinity of representative cloned ligands for LS-Rg, ES-Rg, PS-Rg, CD22β-Rg and WGA was determined by nitrocellulose partitioning and the results shown in Table XIV. The ligands are highly specific for L-selectin. The affinity for ES-Rg is about $10^3$-fold lower and that for PS-Rg is about $5\times10^3$-fold less than for LS-Rg. Binding above background is not observed for CD22β-Rg or for WGA at 0.7 and 1.4 µM protein, respectively, indicating that ligands neither bind the Fc domain of the chimeric constructs nor have affinity for unrelated sialic acid binding sites.

The specificity of oligonucleotide ligand binding contrasts sharply with the binding of cognate carbohydrates by the selectins and reconfirms the assertion that SELEX ligands will have greater specificity than carbohydrate ligands.

Example 16

Cell Binding Studies

Figure 8:
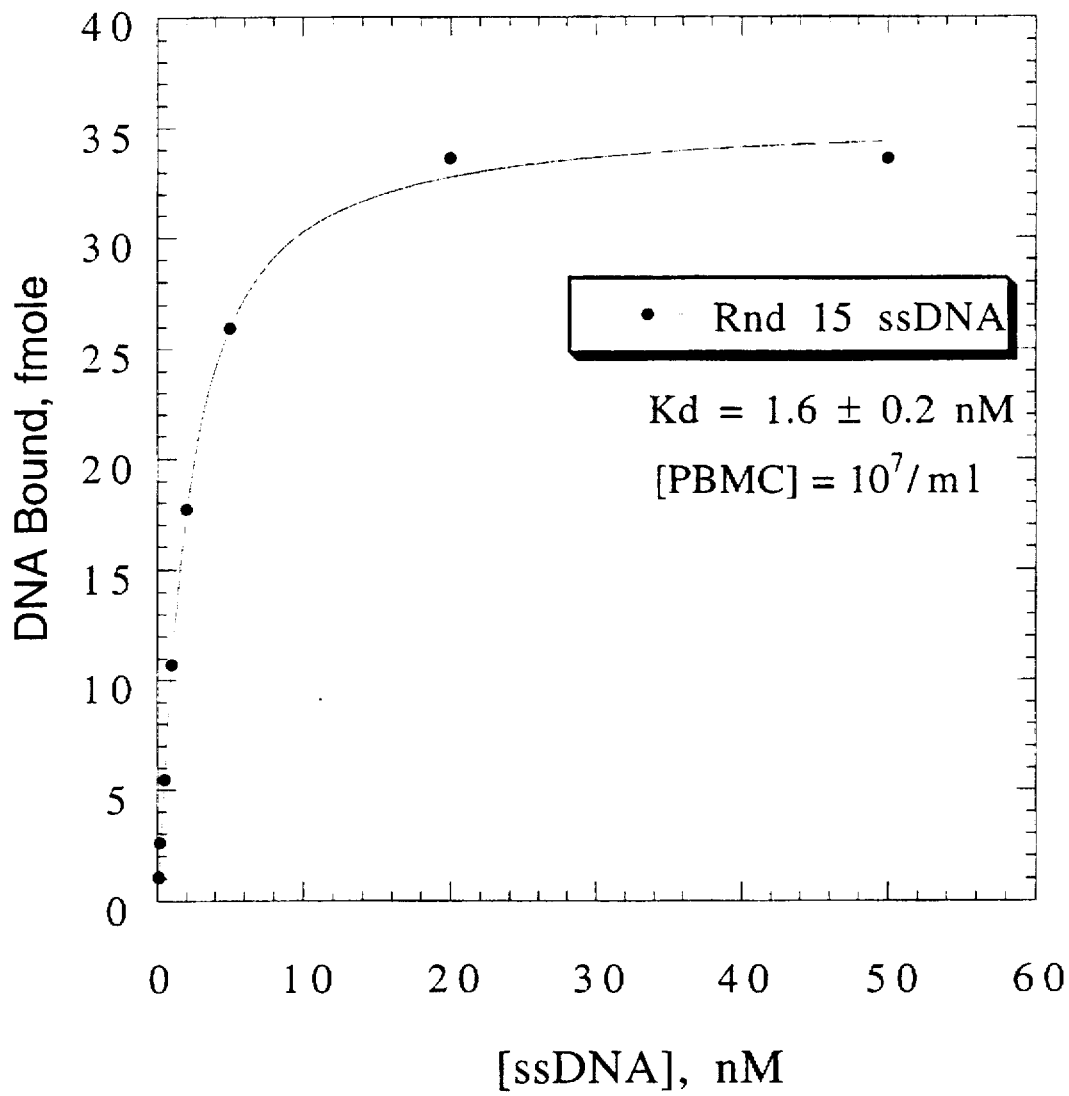
FIG. 8 shows binding curves for the L-selectin SELEX fifteenth round ssDNA pool to PBMCs (10$^7$/ml).
Figure 9:
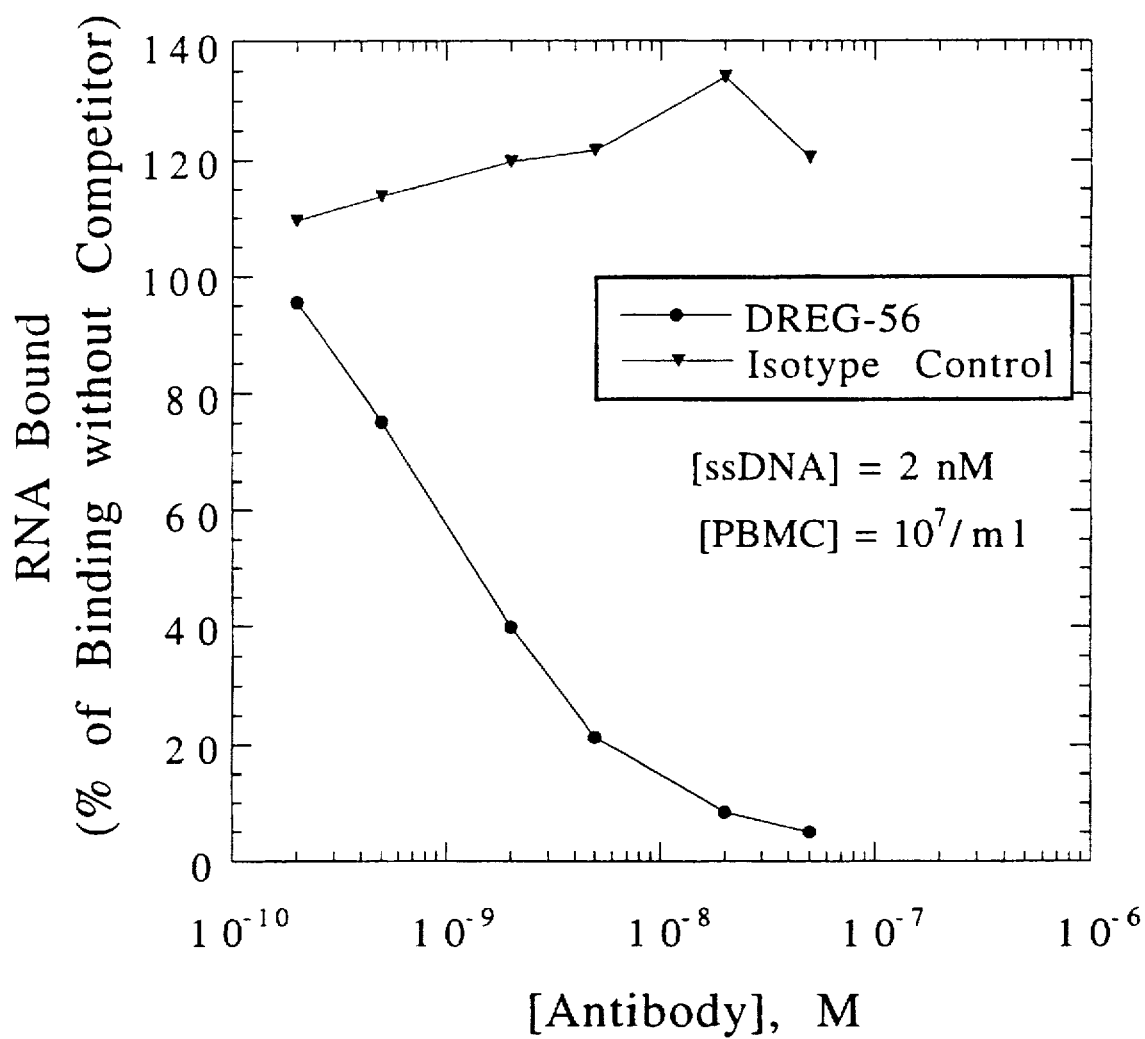
FIG. 9 shows the results of a competition experiment in which the binding of 2 nM $^{32}$P-labeled round 15 ssDNA to PBMCs (10$^7$/ml) is competed with increasing concentrations of the blocking monoclonal anti-L-selectin antibody, DREG-56, or an isotype matched, negative control antibody. RNA Bound equals 100 x (net counts bound in the presence of competitor/net counts bound in the absence of competitor).

Round 15 ssDNA pool was tested for its ability to bind to L-selectin presented in the context of a peripheral blood mononuclear cell surface as described in Example 7, paragraph E. The evolved pool was tested both for affinity and for specificity by competition with an anti-L-selectin monoclonal antibody. FIG. 8 shows that the round 15 ssDNA pool binds isolated PBMCs with a dissociation constant of approximately 1.6 nM and, as is expected for specific binding, in a saturable fashion. FIG. 9 directly demonstrates specificity of binding; in this experiment, binding of 2 nM $^{32}$P-labeled round 15 ssDNA is completely competed by the anti-L-selectin blocking monoclonal antibody, DREG-56, but is unaffected by an isotype-matched irrelevant antibody.

These data validate the feasibilty of using immobilized, purified protein to isolate ligands against a cell surface protein and the binding specificity of round 15 ssDNA ligands to L-selectin in the context of a cell surface.

Example 17

Secondary Structure of High Affinity Ligands

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequence are likely to be directly involved.

Comparative analysis of the family 1 alignment suggests a hairpin secondary structure which is shown in FIG. 10. In the figure, concensus nucleotides are specified, with invariant nucleotides in bold type. To the right of the stem is a matrix showing the number of occurances of particular base pairs for the position in the stem that is on the same line. The matrix illustrates that stem is validated by Watson-Crick covariation. For example, the nucleotide pair on the second line of the matrix is always a Watson-Crick pair (22/22) and is usually an AT (17/22). The stems are 6 or 7 base pairs in length (FIG. 10); the stem position corresponding to line seven is base paired in 12/22 ligands while that corresponding to line eight of the matrix is paired in only one ligand indicating the end of the stem.

There are two major stem variants. In one group of twenty ligands (204 through 227 (SEQ ID NOS: 129–134), Table XII), from 6 lineages, the fourth position from the loop is a TA base pair. The stem of a second group of 19 ligands (112 through 233 (SEQ ID NOS: 135–146), Table XII), from 12 lineages, has a GA mismatch at the fourth position. In both groups, the base pair at the second and third positions from the loop are AT and TA, respectively (FIG. 10).

Twelve nucleotides of the consensus sequence, AAG-GYGYTAVAC (SEQ ID NO: 168), are contained in the loop which is closed by the invariant C and G (FIG. 10). Although interactions of the loop nucleotides are not defined by the data, the invariant T and adjacent Y may interact with the invariant AG.

Initial experiments to deduce the minimal sequence of family 1 ligands that is necessary for high affinity binding indicate that more than the hairpin is required. The affinity of a 41 nucleotide truncate of ligand 201 (SEQ ID NO: 173) is reduced about 15-fold compared to the full length ligand, but the affinity of a 49-mer (SEQ ID NO: 172) is not significantly altered (Table XII and XIII).

Example 18

2'NH$_2$RNA Ligands to Human E-Selectin

Experimental Procedures

A) Materials

ES-Rg is a chimeric protein in which the extracellular domain of human E-selectin is joined to the Fc domain of a human G1 immunoglobulin (R. M. Nelson et al., 1993, supra). Purified chimera were provided by A. Varki. Unless otherwise indicated, all materials used in this SELEX are similar to those of Examples 7 and 13.

B) SELEX

The SELEX procedure is described in detail in U.S. Pat. No. 5,270,163 and elsewhere. The rationale and experimental procedures are the same as those described in Examples 7 and 13.

Example 19 ssDNA Ligands to Human P-Selectin

Experimental Procedures

A) Materials

PS-Rg is a chimeric protein in which the lectin, EGF, and the first two CRD domains of human P-selectin are joined to the Fc domain of a human G1 immunoglobulin (R. M. Nelson et al., 1993, supra). Purified chimera is provided by A. Varki. Soluble P-selectin is purchased from R&D Systems. Unless otherwise indicated, all materials used in the ssDNA SELEX against the P-selectin/IgG$_1$ chimera, PS-Rg, are identical to those of Examples 7 and 13.

B) SELEX

The SELEX procedure is described in detail in U.S. Pat. No. 5,270,163. The specific strategies and procedures for evolving high affinity ssDNA antagonists to P-selectin are described in Examples 7 and 13. The similarity of L- and P-selectin's binding properties assures the success of the experimental procedures in isolating high affinity antagonists to P-selectin.

TABLE I

| Wheat Germ Agglutinin Selex | | | | | | | |
|---|---|---|---|---|---|---|---|
| Round | Total Protein (pmole) | Total RNA (pmole) | Gel Volume (ul) | Total Volume (ul) | % RNA Eluted | % RNA Amplified | Kd (nM) |
| 1 | 5,800 | 2,020 | 50 | 276 | 0.05 | 0.05 | 6,000,000 |
| 2 | 5,800 | 1,070 | 50 | 276 | 0.12 | 0.12 | |
| 3 | 5,800 | 1,770 | 50 | 280 | 0.21 | 0.21 | |
| 4 | 5,800 | 900 | 50 | 263 | 3 | 3 | |
| 5 | 5,800 | 500 | 50 | 271 | 28.5 | 28.5 | 600 |
| 6a | 5,800 | 1,000 | 50 | 282 | 28.8 | | |
| 6b | 580 | 1,000 | 5 | 237 | 5.7 | 0.18 | 400 |
| 7 | 580 | 940 | 5 | 245 | 12.8 | 0.87 | 320 |
| 8 | 580 | 192 | 5 | 265 | 21.4 | 0.64 | 260 |
| 9 | 58 | 170 | 0.5 | 215 | 3.8 | 0.06 | 130 |
| 10 | 58 | 184 | 0.5 | 210 | 5.2 | 0.12 | 94 |
| 11 | 58 | 180 | 0.5 | 210 | 2.3 | 0.07 | 68 |

Wheat Germ Lectin Sepharose 6MB, WGA density, approximately 5 mg/ml of gel or 116 uM.
RNA Loading Conditions: Rounds 1–5, 2 hrs @ room temperature on roller; incubation time reduced to 1 hr. for Rounds 6–11.
RNA Elution Conditions: Rounds 1–5, 200 ul of 2 mM (GlcNAc)3, 15 min. @ room temperature on roller; 2× 200 ul wash with same buffer.
Rounds 6: 200 ul of 0.2 mM (GlcNAc)3, incubated as above; washed sequentially with 200 ul of 0.5, 1, 1.5, 2 and 10 mM (GlcNAc)3.
Rounds 7–8: 200 ul of 0.2 mM (GlcNAc)3, incubated as in round 6; wash twice with same buffer; washed sequentially with 3× 200 ul each, of 0.5, 1.0, 1.5, 2.0 and 10 mM (GlcNAc)3.
Rounds 9–11: incubated 15 @ room temperature in 200 ul of 1 mM (GlcNAc); washed 2× with 200 ul of same buffer; incubation and washes repeated with 1.5, 2.0 and 10 mM (GlcNAc).
% RNA Eluted: percentage of input RNA eluted with (GlcNAc)3
% RNA Amplified: percentage of input RNA amplified;
Rounds 1–5: entire eluted RNA sample amplified.
Rounds 6–11: pooled 2 mM and 10 mM RNA; amplified for subsequent round.
Rounds 9–11: 1.5 mM RNA amplified separately.

TABLE II

Sequence Alignment Wheat Germ Agglutinin

FAMILY 1

| Ligand | SEQ ID NO: | Sequence |
|---|---|---|
| 11.8 | 4 | AUGGUUGGCCUGGCGCAGGCUCUGAAGACUCGCGGGAA CGGGAAUGgucccgcc |
| 11.4(3) | 5 | CAGGCACUG AAAACUCGCGGGAA CG AAAG UAGUGCCGACUCAGACGCGU |
| 11.10 | 6 | AGUCUGGCCAAAGACUCGCGGGAA CGUAAAACGCGGAA CGUAAAACGCAGAAUU |
| 11.35 | 7 | GUAGGAGGUUCCAUCACC AGGACUCGCGGGAA CG AAA GGUGAUGS |
| 11.5 | 8 | ACAAGGAUCGAUGGCGAGCCGGGAGG GCUCGCGGGAA CG AAA UCUgucccgcc |
| 11.26 | 9 | UUGGGCAGCCAGGCAGAGCCGGGCCUCGCGGGAA CG GAACAGGAAUcgcuccgcc |
| 11.19 | 10 | AAGGGAUGGAUUGGGACGAGCGGCC AAGACUCGCGGGAA CG AAG GGUcgcuccgcc |
| 11.15 | 11 | aucauacac agaCUCGCGGGAA CG AAA GUGUCAUGGUAGCAAGUCCAAUGGUGGACUCUc |
| 11.34 | 12 | aucauacac agaCUCGCGGGAA CG AAA GUGGUAGGUAGCUGAAGACGUCUGGGCGCA |
| 6.8 | 13 | AAGGGAUGGGAUUGGGACGAGCGGGCC AAGACUCGCGGGAA CG AAG GGUCCgucccgcc |
| 6.9 | 14 | aucauacaca agaCUCGCGGGAA CG AAG UGUGUGAGUAACGAUCACUUGGUACUAAAGCCC |
| 6.23 | 15 | aucauacaca agaCUCGCGGGAA CG AAA GUGUACUGAAUUAGACACGAUGGCAGYAGUAGUCGGACCC |
| 6.26 | 16 | aaucauacaca agaCUCGCGGGAAUCG AAA UGUCGAUGAUAGCACGAUGGGGYGCGGAGGUCUACCCUGAC |
| 6.14 | 17 | aaucauacacaagaCAGCGCGCG AGUC AAA GUAAAGCCUGGGGGGYGCGGAGGUCUACCCUGAC |
| CONSENSUS: | 56 | AAGACUCGCGGGAA CG AAA |

FAMILY 2

| Ligand | SEQ ID NO: | Sequence |
|---|---|---|
| 11.12 | 18 | CGGCUGUGUGUGGU AGCGUCAUAGGAGAGUCGUCACGAACCAA GGCgcuccgcc |
| 11.24(2) | 19 | CGGCUGU GUGUGUUGGAGCGUCAUAGGAGAGUCGUCACGAACCAA GGCgcuccgcc |
| 11.27(2) | 20 | CGAUGCGAGGCAAGAA AUGGAGUCGUUACGAACCGUU UCUUGCAGUGCGCGc |
| 11.32 | 21 | CGUGCGAGCAAAUAGGGUAC AUGGAGUCGU ACGAACCGUAUCGCgcuccgcc |
| 11.6 | 22 | CUGGGGGAGCAGGAUAUGAGAUGUGCGGGGCA AUGGAGUCGUGACGAACC gcuccgcc |
| | | GGAGUCGUGACGAACC |
| CONSENSUS: | 57 | AAGACUCGCGGGAA CG AAA |

FAMILY 3

| Ligand | SEQ ID NO: | Sequence |
|---|---|---|
| 11.13 | 23 | GUCCGCCCCCAGGGAUGCAACGGGAUGGCAACGGGGUGGCUCUAAAGGCUUGGCUAA |
| 11.23 | 24 | GAGAAUGAGCAUGGCCGGGAUGCAACGGGAUGGGUGGCAACGGAGGCA |
| 6.3 | 25 | GAUACAGCGCGGGUCUAAAGACCUUGCCCCUAGG AUGCAACGGGUGCGUCCGCC |
| 6.7 | 26 | UGAAGGGUUGAAAGAGAGAUCUGAGUC AUGCAACGGGAUCGAAUGGCCACGUCCGCC |
| 6.20 | 27 | CAAACCUGCAGUCGCGCGGUGAAACCUAGGAUGCAACGGGUCCUAGGAUGCAAUCCGCUGUCCGCC |
| 6.34 | 28 | GUGGACUCGGAAUCUUCGAGGACAGGAACGUCCUAGGAUGCAACGGACCGUCCGCC |
| 6.35 | 29 | GUGUACCAAUGGAUGGCAAUGCUCGGGAAUUGGAACGGCCUUAGGAUGCAAC |
| 6.5 | 30 | GUCCCUAGGGAUGCAAC GUCCCUAGGGAUGCAACGGGCAGCAUUCGCAUAGGAGUAAUCGGAGGUC |
| 6.16 | 31 | GCCUAGGAUGCAACGGCGAAUGGAUAGCGAUGGUGGACAGCCAGGU |
| 6.19 | 32 | AUCGAACCUAGGGAUGCAACGGCGUGAAGGUUGUGAGGAUUCGCCAUACGC |
| 6.21 | 33 | GCUAGGGAUGCCGCAGAAUGGUCCGGAUGUAAAAGGUAAGAUGUUGC |
| 6.25 | 34 | GGACCUAGGAUGCAACGGCACCUUGAUGCGGGUGUCCAAGCUAC |
| 6.33 | 35 | AAGGGAGGAGCUAGAGAGGGAAAGGUUACUACGCGCCAGAAUAGAUGU |
| CONSENSUS: | 58 | CCUAGGGAUGCAACGG |

TABLE II-continued

Sequence Alignment Wheat Germ Agglutinin

| Ligand | SEQ ID NO: | |
|---|---|---|
| | | FAMILY 4 |
| 11.2 | 36 | CCAACGUA CAUCGCGAGCUGGUG GAGAGUUCAUGA GGGUGUUACGGGGU |
| 11.33 | 37 | CCCAACGUUCAUCGCGAGCUGGCG GAGAGUUCAUGA GGGU UACGGGU |
| 11.28 | 38 | GUUGGUUGCAGCUGGGGCGGCGA GAAGUAGGCGGUCCGAGUGUU CGAAU |
| 11.7(4) | 39 | aCUGGCAAGRAGUGCGUGAGGGUACGUUAG GGGUGUU UGGGCCGAUCGCAU |
| CONSENSUS: | 59 | RCUGG GAGRGU GGGUGUU |
| 11.20(5) | 40 | UUGGUCGUACUGGACAGAGCCGUGGUAGAGGGAUUGGACAAAGUGUCA |
| | | FAMILY 6 |
| 6.15 | 41 | UGUGAGAAAGUGGCCAACUUUAGGACGUCGGUGGACUGYGCGGUAGGCUC |
| 6.28 | 42 | CAGGCAGAGUGUCUGAGUCGUCGGAGUA GACGUCGUGGAC GCCGAAC |
| CONSENSUS: | 60 | UGUGNNNNAGUNNNNNNNNNUA GACGUCGUUGGACNNNGCGG |
| | | FAMILY 7 |
| 6.24 | 43 | UGUGAUUAGGCAGUUGC.AGCCGCC GU GCGGAGACGU GA CUCGAG GAUUC |
| 6.27 | 44 | UGCCGGUGGAAAGGCGGUAGGU GA CCCGAG GAUUCCUACCAAGCCAU |
| 11.3 | 45 | GAGGUGRA UGGGAGAGUGGAGCCCGGUGACUCGAGAUUCCCGU |
| CONSENSUS: | 61 | GGGNNNGU GA CYCGRG GAYUC |
| | | FAMILY 8 |
| 6.2 | 46 | GUCAUGCUGUGCUGAACAUACUGGUGAAAGUUCAGUAGGGUGGAUACAGuccgc |
| 6.6(2) | 47 | CCCGGGGAUGGUGAGUCGGGC AGUGUGACCGAACUGGUGCCCGUGAGAgcucc |
| CONSENSUS: | 62 | UGANCNNACUGGUGNNNGNNAG |
| | | FAMILY 9 |
| 6.11 | 48 | ACACUAACCAGGUCUCU GAACGCGGGAC GGAGGUG UGGGCGAGGUGAA |
| 6.13 | 49 | CCGUCUCCCGAGAACCAGGCAGGAGGACGUGCGUGAAGGAGCUG CAUCUAGAA |
| 6.17 | 50 | CCGUCUCC GAGAACCAGGAGGAGGUGCUGAAGGRGCUGGCAUCUACAA |
| CONSENSUS: | 63 | GUCUCY GAACNNGGNA GGANGUGNUG GAGNUG |
| | | ORPHANS |
| 6.1 | 51 | CCCGCACAUAAUGUAGGGAACAAUGUUAUGGCGGAAUUGAUAACCGGU |
| 6.4 | 52 | CGAUGUUAGCGCCUCCGGGAGAGAGGGUUAGGGUCGGNAAAGAGUGAGGU |
| 6.18 | 53 | CGUACGGGCGAGACGAGAUGGACUUAUAGGGUGAUGAACGGUAGCAGCUC |
| 11.30 | 54 | CGGUUGCUGAACAGAACGUGAGUCUGGGUGAGUCGCACAGAUUGUCCU |
| 11.29 | 55 | ACUGAGUAAGGUCUGGCGUGGCAUUAGGUUAGGGAGGCUUGGAGUAGC |

TABLE III

Dissociation Constants of RNA Ligands to WGA

| Ligand | SEQ ID NO: | Kd |
|---|---|---|
| Family 1 | | |
| 11.8 | 4 | 9.2 nM |
| 11.4 | 5 | 32 nM |
| 11.35 | 7 | 90 nM |
| 11.5 | 8 | 44 nM |
| 11.26 | 9 | 38 nM |
| 11.19 | 10 | 22 nM |
| 11.15 | 11 | 54 nM |
| 11.34 | 12 | 92 nM |
| 6.8 | 13 | 11 nM |
| 6.9 | 14 | 396 nM |
| 6.23 | 15 | 824 nM |
| 6.14 | 17 | <5% |
| Family 2 | | |
| 11.12 | 18 | 15.2 nM |
| 11.24 | 19 | 19.4 nM |
| 11.27 | 20 | 30 nM |
| 11.32 | 21 | 274 nM |
| 11.6 | 22 | 702 nM |
| Family 3 | | |
| 11.13 | 23 | <5% |
| 11.23 | 24 | <5% |
| 6.3 | 25 | 120 nM |
| 6.2 | 27 | <5% |
| 6.34 | 28 | <5% |
| 6.35 | 29 | <5% |
| 6.5 | 30 | 678 nM |
| 6.16 | 31 | <5% |
| 6.19 | 32 | 74 nM |
| Family 4 | | |
| 11.2 | 36 | 62 nM |
| 11.33 | 37 | <5% |
| 11.28 | 38 | 9.2 nM |
| 11.7 | 39 | 16 nM |
| Family 5 | | |
| 11.2 | 40 | 1.4 nM |
| Family 7 | | |
| 6.27 | 44 | 56 nM |
| 11.3 | 45 | 410 nM |
| Family 8 | | |
| 6.6 | 47 | <5% |
| Family 9 | | |
| 6.11 | 48 | <5% |
| Orphans | | |
| 11.3 | 54 | 56 nM |
| 11.29 | 55 | 32 nM |

The Kds of ligands that show <5% binding at 1 uM WGA is estimated to be >20 uM.

TABLE IV

Specificity of RNA Ligands to WGA

Kds for N-acetyl-glucosamine Binding Lectins

| LECTIN | Ligand 6.8 (SEQ ID NO:13) | Ligand 11.20 (SEQ ID NO:40) | Ligand 11.24 (SEQ ID NO:19) |
|---|---|---|---|
| Triticum vulgare (WGA) | 11.4 nM | 1.4 nM | 19.2 nM |
| Canavalia ensiformis (Con A)** | <5%* | <5%* | <5%* |
| Datura stramonium | <5%* | 11.2 µM | <5%* |
| Ulex europaeus (UEA-II) | 4.4 µM | 2.2 µM | <5%* |

*Less than 5% binding at 1 µM protein; estimated Kd > 20 µM
**succinylated Con A

TABLE V

INHIBITION OF RNA LIGAND BINDING TO WHEAT GERM AGGULTININ

| Ligand | SEQ ID NO: | Competitor | IC$_{50}$ (µM) | Max Inhib | K$_c$ (µM) |
|---|---|---|---|---|---|
| 6.8 | 13 | (GlcNAc)$_3$ | 95 | >95% | 10.9 |
| 11.20 | 40 | (GlcNAc)$_3$ | 120 | >95% | 8.4 |
| 11.24 | 19 | (GlcNAc)$_3$ | 120 | >95% | 19.4 |

K$_c$ is the dissociation constant of (GlcNAc)$_3$ calculated from these data, assuming competitive inhibition and two RNA ligand binding sites per dimer.

TABLE VI

INHIBITION OF WGA MEDIATED AGGLUTINATION OF SHEEP ERYTHROCYTES

| Inhibitor | SEQ ID NO: | Inhibitory Concentration (µM) Complete | Partial |
|---|---|---|---|
| 6.8 | 13 | 0.5 | 0.12 |
| 11.20 | 40 | 0.5 | 0.12 |
| 11.24 | 19 | * | 2 |
| (GlcNAc)$_3$ | | 8 | 2 |
| GlcNAC | | 780 | 200 |

*Complete inhibition of agglutination by ligand 11.24 was not observed in this experiment.

TABLE VIIa

L-Selectin SELEX: 2'NH$_2$ RNA at 4° C.

| SELEX Round # | Total RNA pmoles | Total Protein pmoles | RNA:LS-Rg Ratio | Bead Volume | Total Volume | % 5 mM EDTA Eluted RNA | % 50 mM EDTA Eluted RNA | Kd (nM) |
|---|---|---|---|---|---|---|---|---|
| Rnd 0 | | | | | | | | 10,000 |
| Rnd 1 | 1060 | 167.0 | 6.3 | 10 μL | ~100 μL | 0.498 | 0.301 | |
| Rnd 2 | 962 | 167.0 | 5.8 | 10 μL | ~100 μL | 0.306 | 0.114 | |
| Rnd 3 | 509 | 167.0 | 3.0 | 10 μL | ~100 μL | 1.480 | 0.713 | |
| Rnd 4 | 407 | 167.0 | 2.4 | 10 μL | ~100 μL | 5.010 | 1.596 | 434 |
| Rnd 5 | 429 | 167.0 | 2.6 | 10 μL | ~100 μL | 8.357 | 7.047 | |
| | 439 | 16.7 | 26.3 | 10 μL | ~100 μL | 0.984 | 0.492 | 133 |
| Rnd 6 | 452 | 167.0 | 2.7 | 10 μL | ~100 μL | 7.409 | 6.579 | |
| | 46 | 16.7 | 2.8 | 10 μL | ~100 μL | 3.468 | 1.312 | 37 |
| Rnd 7 | 43 | 16.7 | 2.6 | 10 μL | ~100 μL | 8.679 | 2.430 | |
| | 44 | 16.7 | 2.6 | 10 μL | ~100 μL | 7.539 | 2.358 | |
| | 22 | 4.2 | 5.2 | 10 μL | ~100 μL | 2.748 | 1.298 | |
| Rnd 8 | 43 | 16.7 | 2.6 | 10 μL | ~100 μL | 8.139 | 1.393 | 33 |
| | 23 | 4.2 | 5.5 | 10 μL | ~100 μL | 2.754 | 0.516 | |
| Rnd 9 | 23 | 4.2 | 5.5 | 10 μL | ~100 μL | 4.352 | 0.761 | |
| Rnd 10 | 21 | 4.2 | 5.0 | 10 μL | ~100 μL | 6.820 | 1.123 | 13 |
| | 23 | 8.4 | 2.7 | 50 μL | ~150 μL | 14.756 | 1.934 | |
| Rnd 11 | 30 | 10.5 | 2.9 | 250 μL | ~500 μL | 0.707 | 0.033 | |
| Rnd 12 | 12 | 10.5 | 1.1 | 250 μL | ~500 μL | 3.283 | 0.137 | |
| Rnd 13 | 7 | 1 | 7 | 250 μL | ~500 μL | 4.188 | 0.136 | 0.3 |
| Rnd 14 | 9 | 1 | 9 | 250 μL | ~500 μL | 4.817 | 0.438 | 0.7 |

L-Selectin Rg was immobilized on Protein A Sepharose 4 Fast Flow. Protein A density is approximately 6 mg/ml drained gel (143 uM).
RNA Loading Conditions: All selections were carried out in the cold room. The RNA used in each selection was first incubated for 30 minutes with 100 uL Protein A Sepharose in the cold room on a roller. Only RNA which flowed through this column was used on the LS-Rg selection column. The RNA was incubated on the selection column for 90 minutes on a roller before being washed extensively with binding buffer (20 mM HEPES pH 7.4 150 mM NaCl, 1 mM MgCl$_2$, 1 mM CaCl$_2$.)
RNA Elution Conditions: RNA was eluted by incubating the extensively-washed columns in 100 uL of HEPES buffered EDTA (pH 7.4) for 30 minutes on a roller followed by three 100 uL HEPES buffered EDTA washes.

TABLE VIIb

L-Selectin SELEX: 2'NH$_2$ RNA at Room Temperature

| SELEX Round # | Total RNA pmoles | Total Protein pmoles | RNA:LS-Rg Ratio | Bead Volume | Total Volume | % 5 mM EDTA Eluted RNA | % 50 mM EDTA Eluted RNA | Kd (nM) |
|---|---|---|---|---|---|---|---|---|
| Rnd 7 | 43 | 10.0 | 4.3 | 10 μL | ~100 μL | 1.205 | 0.463 | |
| Rnd 8 | 35 | 10 | 3.5 | 10 μL | ~100 μL | 6.642 | 0.401 | |
| | 35 | 10 | 3.5 | 10 μL | ~100 μL | 5.540 | 0.391 | |
| Rnd 9 | 24 | 2.5 | 9.6 | 10 μL | ~100 μL | 1.473 | 0.383 | 13 |
| Rnd 10 | 30 | 6.3 | 4.9 | 250 μL | ~500 μL | 0.707 | 0.033 | |
| Rnd 11 | 12 | 6.3 | 1.9 | 250 μL | ~500 μL | 3.283 | 0.134 | |
| Rnd 12 | 6 | 0.6 | 9.4 | 250 μL | ~500 μL | 0.877 | 0.109 | 0.3 |
| Rnd 13 | 1 | 0.6 | 1.4 | 250 μL | ~500 μL | 5.496 | 0.739 | 0.7 |

L-Selectin Rg was immobilized on Protein A Sepharose 4 Fast Flow. Protein A density is approximately 6 mg/ml drained gel (143 uM).
RNA Loading Conditions: Selections were carried out at room temperature. The RNA used in each selection was first incubated for 30 minutes with 100 uL Protein A Sepharose at room temp. Only RNA which flowed through this column was used on the LS-Rg selection column. The RNA was incubated on the selection column for 90 minutes on a roller before being washed extensively with binding buffer (20 mM HEPES pH 7.4 150 mM NaCl, 1 mM MgCl$_2$, 1 mM CaCl$_2$.)
RNA Elution Conditions: RNA was eluted by incubating the extensively-washed columns in 100 uL of HEPES buffered EDTA (pH 7.4) for 30 minutes on a roller followed by three 100 uL HEPES buffered EDTA washes.

TABLE VIII

L-Selectin 2'NH$_2$ RNA SELEX:
Ligand Sequences

| Ligand | SEQ ID NO: | Sequence |
|---|---|---|
| Family I | | |
| F13.32(5) | 67 | CGCGUAUGUGUGAAAGCGUGUGCACGGAGGCGU—CUACAAU |
| 6.60(2) | 68 | GGCAUUGUGUGAAUAGCUGAUCCCACAGGUAACAACAGCA |
| 6.50(3) | 69 | UAAUGUGUGAAUCAAGCAGUCUGAAUAGAUUAGACAAAAU |
| 6.79 | 70 | AUGUGUGAGUAGCUGAGCGCCCGAGUAUGAWACCUGACUA |
| F14.9 | 71 | AAACCUUGAUGUGUGAAUAGAGCAUCCCCCAGGCGACGUAC |
| F14.21 | 72 | UUGAGAUGUGUGAGUACAAGCUCAAAAUCCCGUUGGAGG |
| F14.25 | 73 | UAGAGGUAGUAUGUGUGGGAGAUGAAAAUACUGUGGAAAG |
| F13.48(2) | 74 | AAAGUUAUGAGUCCGUAUAUCAAGGUCGACAUGUGUGAAU |
| 6.71 | 75 | CACGAAAAACCCGAAUUGGGUCGCCCAUAAGGAUGUGUGA |
| 6.28 | 76 | GUAAAGAGAUCCUAAUGGCUCGCUAGAUGUGAUGUGAAAC |
| CONSENSUS: | 118 | AUGUGUGA |
| Family II | | |
| F14.20(26) | 77 | UAACAA CAAUCAAGGCGGGUUCACCGCCCCAGUAUGAGUG |
| F14.12(22) | 78 | UAACAA CAAUCAAGGCGGGUUYACCGCCCCAGUAUGAGUA |
| F14.11(12) | 79 | UAACAA CAAUCAAGGCGGGUUYACCGCUCCAGUAUGAGUA |
| F13.45(9) | 80 | UAACAA CAAUCAAGGCGGGUUCACCGCCCCAGUAUGAGUG |
| 6.80 | 81 | ACCAAGCAAUCUAU GGUCGAACGCUACA CAUGAAUGACGUc |
| CONSENSUS: | 119 | CAA CAAUC AUGAGUR |
| Family III | | |
| 6.17 | 82 | GAACAUGAAGUAAUCAAAGUCGUACC AAUAUACAGGAAGC |
| 6.49 | 83 | GAACAUGAAGUAAGAC CGUCAC AAUUCGAAUGAUUGAAUA |
| 6.16 | 84 | GAACAUGAAGUAAAA AGUCGACG AAUUAGCUGUAACCAAAA |
| 6.37 | 85 | GAACAUGAAGUAAA AGUCUG AGUUAGUAAAUUACAGUGAU |
| 6.78 | 86 | GAACUUGAAGUUGA ANUCGCUAA GGUUAUGGAUUCAAGAUU |
| 6.26 | 87 | AACAUGAAGUAAUA AGUC GACGUAAUUAGCUGUAACUAAA |
| 6.40 | 88 | AACAUGAAGUAAA AGUCUG AGUUAGAAAUUACAAGUGAU— |
| F13.57 | 89 | UAACAUAAAGUAGCG CGUCUGUGAGAGGAAGUGCCUGGAU |
| CONSENSUS: | 120 | AACAUGAAGUA AGUC ARUUAG |
| Family IV | | |
| 6.58 | 90 | AUAGAACCGCAAGGAUAACCUCGACCGUGGUCAACUGAGA |
| 6.69 | 91 | UAAGAACCGCUAGCGCACGAUCAAACAAAGAGAAACAAA— |
| CONSENSUS: | 121 | AGAACCGCWAG |
| Family V | | |
| 6.56 | 92 | UUCUCUCCAAGAACYGAGCGAAUAAACSACCGGASUCACA |
| F13.55 | 93 | UGUCUCUCCUGACUUUUAUUCUUAGUUCGAGCUGUCCUGG |
| CONSENSUS: | 122 | UCUCUCC |
| Family VI | | |
| F14.27 | 94 | CCGUACAUGGUAARCCU CGAAGGAUUCCCGGGAUGAUCCC |
| F14.53 | 95 | UCCCAGAGUCCCGUGAUGCGAAGAAUCCAUUAGUACCAGA |
| CONSENSUS: | 123 | CGAAGAAUYC |
| Family VII | | |
| F13.42 | 96 | GAUGUAAAUGACAAAUGAACCUCGAAAGAUUGCACACUC |
| F13.51 | 97 | AUGUAAAUCUAGGCAGAAACGUAGGGCAUCCACCGCAACGA |
| CONSENSUS: | 124 | AUGUAAAU |
| Family VIII | | |
| 6.33(11) | 98 | AUAACCCAAGCAGCNUCGAGAAAGAGCUCCAUAGAUGAU— |
| 6.41 | 99 | CAAAGCACGCGUAUGGCAUGAAACUGGCANCCCAAGUAAG |
| CONSENSUS: | 125 | AACCCAAG |
| Family IX | | |
| F13.46(4) | 100 | CAAAAGGUUGACGUAGCGAAGCUCUCAAAAUGGUCAUGAC |
| Family X | | |
| F14.2 | 101 | AAGUGAAGCUAAAGCGGAGGG CCAUUCAGUUUCNCACCA |
| F14.13(2) | 102 | AAGUGAAGCUAAAGSGGAGGG CCACUCAGAAACGCACCA |
| Family XI | | |
| 6.72(2) | 103 | CACCGCUAAGCAGUGGCAUAGCCCAGUAACCUGUAAGAGA |
| 6.42 | 104 | CAC—GCUAAGCAGUGGCAUAGC——GWAACCUGUAAGAGA |
| Family XII | | |
| 6.30(5) | 105 | AGAUUACCAUAACCGCGUAGUCGAAGACAUAUAGUAGCGA |

TABLE VIII-continued

L-Selectin 2'NH₂ RNA SELEX:
Ligand Sequences

| Ligand | SEQ ID NO: | |
|---|---|---|
| | | Family XIII |
| 6.52(2) | 106 | ACUCGGGUAGAACGCGACUUGCCACCACUCCCAUAAAGAC |
| | | Orphans |
| 6.14 | 107 | UCAGAACUCUGCCGCUGUAGACAAAGAGGAGCUUAGCGAA |
| 6.36 | 108 | AAUGAGCAUCGAGAGAGCGCGAACUCAUCGAGCGUACUAA |
| 6.41 | 119 | CAAAGCACGCGUAUGGCAUGAAACUGGCANCCCAAGUAAG |
| 6.44 | 110 | GAUGCAGCAACCUGAAAACGGCGUCCACAGGUAAUAACAG |
| 6.70 | 111 | AAACUCGCUACAAACACCCAAUCCUAGAACGUUAUGGAGA |
| 6.76 | 112 | CUAGCAUAGCCACCGGAACAGACAGAUACGAGCACGAUCA |
| 6.89 | 113 | GAUUCGGAGUACUGAAAAACAACCCUCAAAAGUGCAUAGG |
| 6.81 | 114 | GUCCAGGACGGACCGCAGCUGUGAUACAAUCGACUUACAC |
| 6.70 | 115 | AAACUCGCUACAAACACCCAAUCCUAGAACGUUAUGGAGA |
| F13.59 | 116 | CGGCCCUUAUCGGAGGUCUGCGCCACUAAUUACAUCCAC |
| F14.70 | 117 | UCCAGAGCGUGAAGAUCAACGUCCCGGNGUCGAAGA |

TABLE IX

Dissociation Constants of Cloned Ligands to L-Selectin*

| Ligand | SEQ ID NO: | 4° C. | Rm Temp |
|---|---|---|---|
| | | Family I | |
| F13.32 | 67 | 15.7 nM | 14.9 nM |
| F13.48 | 74 | 15.9 nM | 9.2 nM |
| F14.9 | 71 | 8.2 nM | 15.4 nM |
| F14.21 | 72 | 2.3 nM | 15.9 nM |
| F14.25 | 73 | 1300 nM | |
| | | Family II | |
| F14.12 | 78 | 5.8 pM (0.68) 16.2 nM | 1.7 nM (0.62) 94 nM |
| F14.20 | 77 | 58 pM (0.68) 60 nM | 1.0 nM (0.28) 48 nM |
| | | Family III | |
| F13.57 | 89 | 3.0 nM | 75 nM |
| | | Family V | |
| F13.55 | 93 | 62 pM | 1.5 nM |
| | | Family VI | |
| F14.53 | 95 | 97 pM (0.65) 14.5 nM | 142 nM |
| F14.27 | 94 | 145 nM | |
| | | Family VII | |
| F13.42 | 96 | 2.0 nM | 5.5 nM |
| F13.51 | 97 | 8.8 nM | 18 nM |
| | | Family IX | |
| F13.52 | | 3.0 nM | 25 nM |
| | | Family X | |
| F14.2 | 101 | 1.8 nM | 7.2 nM |
| F14.13 | 102 | 1.3 nM (0.74) 270 nM | |
| | | Orphans | |
| F13.59 | 116 | <5% | <5% |
| F14.70 | 117 | 2.0 nM (0.75) 254 nM | 7.8 nM (0.58) 265 nM |

*Kds of monophasic binding ligands are indicated by a single number; the high affinity $K_d$ (ie., $K_{d1}$), the mole fraction binding with $K_{d1}$, and the low affinity $K_d$ (ie., $K_{d2}$) are presented for biphasic binding ligands.

TABLE X

Specificity of Cloned Ligands to L-Selectin*

| Ligand | SEQ ID NO: | LS-Rg | ES-Rg | PS-Rg | CD22-Rg |
|---|---|---|---|---|---|
| | | Family I | | | |
| F13.32 | 67 | 15.7 nM | <5% | 17 μM | <5% |
| F13.48 | 74 | 15.9 nM | <5% | 720 nM | <5% |
| F14.9 | 71 | 8.2 nM | <5% | | <5% |
| F14.21 | 72 | 2.3 nM | 2.6 μM | | <5% |
| F14.25 | 73 | 1300 nM | | | |
| | | Family II | | | |
| F14.12 | 78 | 60 pM | 47 nM | 910 nM | <5% |
| F14.20 | 77 | 58 pM (0.68) 60 nM | 70 nM | | <5% |
| | | Family III | | | |
| F13.57 | 89 | 3.0 nM | 2.7 μM | | |
| | | Family V | | | |
| F13.55 | 93 | 62 pM | 49 nM | 5.8 μM | <5% |
| | | Family VI | | | |
| F14.53 | 95 | 97 pM (0.65) 14.5 nM | 355 nM | 5.2 μM | <5% |
| | | Family VII | | | |
| F13.42 | 96 | 2.0 nM | 4.4 μM | | <5% |
| F13.51 | 97 | 8.8 nM | 2.0 μM | | |

TABLE X-continued

Specificity of Cloned Ligands to L-Selectin*

| Ligand | SEQ ID NO: | LS-Rg | ES-Rg | PS-Rg | CD22-Rg |
|--------|-----------|-------|-------|-------|---------|
| Family IX | | | | | |
| F13.52 | | 3.0 nM | 2.5 µM | | <5% |
| Family X | | | | | |
| F14.2 | 101 | 1.8 nM | 1.9 µM | 450 nM | <5% |
| Orphans | | | | | |
| F13.59 | 116 | <5% | <5% | | <5% |
| F14.70 | 117 | 2.0 nM (0.75) 254 nM | 5.9 µM | | <5% |

*Dissociation constants were determined at 4° C. in HSMC buffer. When <5% binding was observed at the highest protein concentration, the Kd is estimated to be >20 µM.

TABLE XI

LS-Rg ssDNA SELEX

| Round | Temp. | Total DNA pmol | Total Prot. pmol | DNA:Protein | Bead Vol. | Total Vol. | % Eluted 2 mM EDTA | % Eluted 50 mM EDTA | Kd, nM 4 degrees | signal:bkgd 2 mM |
|-------|-------|----------------|------------------|-------------|-----------|------------|---------------------|----------------------|-------------------|-------------------|
| Rnd 0 | | | | | | | | | 10,000 | |
| Rnd 1 | 4 | 930 | 167 | 5.6 | 10 µL | ~100 µL | n/a | 5.5 | | 50 |
| Rnd 2 | 25 | 400 | 167 | 2.4 | 10 µL | ~100 µL | n/a | 2.19 | | 12 |
| Rnd 3 | 25 | 460 | 167 | 2.8 | 10 µL | ~100 µL | n/a | 2.55 | | 25 |
| Rnd 4 | 25 | 100 | 16.7 | 6 | 10 µL | ~100 µL | 0.35 | 0.29 | | 1.3 |
| Rnd 5 | 25 | 100 | 16.7 | 6 | 10 µL | ~100 µL | 0.23 | 0.08 | 967 | 3 |
| Rnd 6 | 25 | 1000 | 16.7 | 60 | 10 µL | ~100 µL | 1.42 | 0.38 | | 4 |
| Rnd 7 | 25 | 100 | 16.7 | 6 | 10 µL | ~100 µL | 6.9 | 0.93 | 60 | 18 |
| Rnd 8 | 37 | 100 | 16.7 | 6 | 10 µL | ~100 µL | 1.9 | 0.31 | | 9 |
| Rnd 9 | 25 | 10 | 1.67 | 6 | 10 µL | ~100 µL | 0.5 | 0.16 | 2.1 | 1.6 |
| Rnd 10 | 25 | 10 | 1.67 | 6 | 10 µL | ~100 µL | 2.2 | 0.57 | | 5 |
| Rnd 11 | 25 | 2.5 | 0.42 | 6 | 10 µL | ~100 µL | 0.37 | 0.07 | 1.3 @ 25° C. | 8 |
| Rnd 12 | 25 | 2.5 | 0.42 | 6 | 10 µL | ~100 µL | 0.86 | 0.13 | | 11 |
| Rnd 13 | 37 | 2.5 | 0.42 | 6 | 10 µL | ~100 µL | 0.7 | 0.35 | 0.44 @ 25° C. | 5 |
| Rnd 14 | 25 | 5 | 0.84 | 6 | 50 µL | ~100 µL | 2.8 | 0.76 | | 4 |
| Rnd 15 | 25 | 1.25 | 0.21 | 6 | 50 µL | ~100 µL | 1.7 | 0.5 | 0.16 @ 25° C. | 7 |

Binding Buffer, Rounds 1–9
10 mM HEPES, pH at room temp w/NaOH to 7.4
100 mM NaCl
1 mM MgCl2
1 mM CaCl2
5 mM KCl
Elution Buffers: replace divalent cations with EDTA

TABLE XII

L-Selectin ssDNA SELEX: Ligand Sequences

| Ligand | ID # | | | |
|--------|------|---|---|---|
| Family 1 | | | | |
| 204(3) | 129 | GGAACACGTGAGGTTTAC | AAGGCACTCGAC | GTAAACACTT |
| 145 | 130 | CCCCGAAGAACATTTTAC | AAGGTGCTAAAC | GTAAAATCAG |
| 183(2) | 131 | GGCATCCCTGAGTCATTAC | AAGGTTCTTAAC | GTAATGTAC |
| 230(2) | 132 | TGCACACCTGAGGGTTAC | AAGGCGCTAGAC | GTAACCTCTC |
| 208(7) | 133 | CACGTTTC | AAGGGGTTACAC | GAAACGATTCACTCCTTGGC |
| 227(5) | 134 | CGGACATGAGCGTTAC | AAGGTGCTAAAC | GTAACGTACTT |
| 112 | 135 | CGCATCCACATAGTTC | AAGGGGCTACAC | GAAATATTGCA |
| 137 | 136 | TACCCCTTGgGCCTCATAGAC | AAGGTCTTAAAC | GTTAGC |
| 179(2) | 137 | CACATGCCTGACGCGGTAC | AAGGCCTGG AC | GTAACGTTG |
| 182 | 138 | TAGTGCTCCACGTATTC | AAGGTGCTAAAC | GAAGACGGCCT |
| 190 | 139 | AGCGATGC | AAGGGGCTACAC | GCAACGATTTAGATGCTCT |
| 193(2) | 140 | CCAGGAGCACAGTAC | AAGGTGTTAAAC | GTAATGTCTGGT |
| 199 | 141 | ACCACACCTGGGCGGTAC | AAGGAGTTATCC | GTAACGTGT |
| 201(2) | 142 | CAAGGTAACCAGTAC | AAGGTGCTAAAC | GTAATGGCTTCG |
| 203 | 143 | ACCCCCGACCCGAGTAC | AAGGCATTCGAC | GTAATCTGGT |

TABLE XII-continued

L-Selectin ssDNA SELEX:
Ligand Sequences

| Ligand | ID # | Sequence |
|---|---|---|
| 207 | 144 | <u>CAGTAC</u>  AAGGTGTTAAAC  <u>GTAA</u>TGCCGATCGAGTTGTAT |
| 216 | 145 | ACAA<u>CGAGTAC</u>  AAGGAGATAGAC  <u>GTAA</u>TCGGCGCAGGTATC |
| 233(5) | 146 | CACGAC<u>AGAGAAC</u>  AAGGCGTTAGAC  <u>GTTA</u>TCCGACCACG |
| 191 | 147 | A<u>GGGAGAAC</u>  AAGGTGCTAAAC  <u>GTTTATCT</u>ACACTTCACCT |
| 128(3) | 148 | <u>AGGAC</u>C  AAGGTGTTAAAC  <u>GGCTCCCC</u>TGGCTATGCCTCTT |
| 111(2) | 149 | gc<u>TACAC</u>  AAGGTGCTAAAC  <u>GTAGAGC</u>CAGATCGGATCTGAGC |
| 139 | 150 | <u>GGAC</u>  AAGGCACTCGAC  <u>GTAGTTTA</u>TAACTCCCTCCGGgCC |
| 237 | 151 | gc<u>TACAC</u>  AAGGGGCCAAAC  <u>GGAGAGC</u>CAGACGCGGATCTGACA |
| 173 | 152 | CGGCTATA<u>C</u>  NNGGTGCTAAAC  <u>GC</u>AGAGACTCGATCAACA |
| 209 | 153 | GAGTAG<u>CC</u>  AAGGCGTTAGAC  <u>GG</u>AGGGGGAATGGAAGCTTG |
| 221 | 154 | GAGTAG<u>CC</u>  AAGGCGTTAGAC  <u>GG</u>AGGGGGAATGG |
| 108 | 155 | GAGTAG<u>CC</u>  AAGGCGTTAGAC  <u>GG</u>AGGGGGAATGTGAGCACA |
| 141 | 156 | TAGCTCCACACAC  AASSCGCRGCAC  ATAGGGGATATCTGG |
| Truncates | | |
| 201T1 | 172 | tagcCAAGGTAA<u>CCAGTAC</u>  AAGGTGCTAAAC  <u>GTAA</u>TGGCTTCGgCttaC |
| 201T3 | 173 | GTAA<u>CCAGTAC</u>  AAGGTGCTAAAC  <u>GTAA</u>TGGCTTCGgcttac |
| Consensus: | 168 | TAC  AAGG<u>Y</u>GYTAVAC  GTA |

Family 2

| | | |
|---|---|---|
| 181(3) | 157 | CAT  CAAGGACTTTGCCCGAAACCCTAGGTTCACG TGTGGG |

Family 4

| | | |
|---|---|---|
| 174(2) | 158 | CATTCACCATGGCCCCTTCCTACGTATGTTCTGCGGGTG |
| 122 | 159 | GCAACGTGGCCCCGTT  TAGCTCATTTGACCGTTCCATCCG |
| 239 | 160 | CCACAGACAATCGCAGTCCCCGTG  TAGCTCTGGGTGTCT |
| Consensus: | 169 | GGCCCCGT |

Family 5

| | | |
|---|---|---|
| 109 | 161 | CCACCGTGAT<u>GCACGATACA</u>TGAGGGTGTGTCAGCGCAT |
| 127 | 162 | CGAGGTAGTCGTTAT<u>AGGGTRCRCACGACACA</u>AARCRGTR |
| Consensus: | 170 | RCACGAYACA |

Family 6

| | | |
|---|---|---|
| 196 | 163 | TGGCGGTACGGGCCGTGCACCCACTTACCTGGGAAGTGA |
| 229 | 164 | CTCTGCTTACCTCATGTAGTTCCAAGCTTGGCGTAATCATG |
| Consensus: | 171 | CTTACCT |

Family 7

| | | |
|---|---|---|
| 206(2) | 165 | AGCGTTGTACGGGGTTACACACAACGATTTAGATGCTCT |

Orphans

| | | |
|---|---|---|
| 214 | 166 | TGATGCGACTTTAGTCGAACGTTACTGGGGCTCAGAGGACA |
| 102 | 167 | CGAGGATCTGATACTTATTGAACATAMCCGCACNCAGGCTT |

TABLE XIII

Dissociation Constants of Cloned Ligands from ssDNA SELEX Against L-Selectin

| Ligand | SEQ ID NO: | Room Temperature | 37° C. |
|---|---|---|---|
| Family 1 | | | |
| 111 | 149 | 330 pM | 11.8 nM |
| 128 | 148 | 310 pM | 1.8 nM |
| 108 | 155 | 160 pM | 8.5 nM |
| 112 | 135 | 300 pM | 23.2 nM |
| 137 | 136 | 520 pM | 0.65 nM |
| 139 | 150 | 210 pM | 6.8 nM |
| 145 | 130 | 920 pM | 8.8 nM |
| 179 | 137 | 180 pM | 590 pM |
| 182 | 138 | 130 pM | 2.0 nM |
| 183 | 131 | 170 pM | 1.0 nM |
| 193 | 140 | 88 pM | 970 pM |
| 201 | 142 | 110 pM | 1.2 nM |
| 204 | 129 | 100 pM | 3.7 nM |
| 208 | 155 | 110 pM | 380 pM |
| 227 | 134 | 43 pM | 160 pM |
| 230 | 132 | 57 pM | 260 pM |
| 233 | 146 | 110 nM | 380 pM |
| Family 2 | | | |
| 181 | 157 | 84 pM | 1.8 nM |
| Family 4 | | | |
| 122 | 159 | 1.8 nM | 2.1 nM |
| 174 | 158 | 43 pM | 370 pM |
| 239 | 160 | 170 pM | 1.6 nM |
| Family 5 | | | |
| 109 | 161 | 190 pM | 9.6 nM |
| 127 | 162 | 1.0 nM | 890 pM |
| Family 6 | | | |
| 196 | 163 | 130 pM | 3.4 nM |

TABLE XIII-continued

Dissociation Constants of Cloned Ligands from ssDNA SELEX Against L-Selectin

| Ligand | SEQ ID NO: | Room Temperature | 37° C. |
|---|---|---|---|
| Family 7 | | | |
| 206 | 165 | 330 pM | 6.0 nM |
| Orphans | | | |
| 102 | 167 | not determined | 7.9 nM |
| 214 | 166 | 660 pM | 8.4 nM |
| Round 15 Pool | | 160 pM | 660 pM |
| 201T1* | | | 4.8 nM |
| 201T3* | | | 43 nM |

*201T1 and 201T3 were made by solid state synthesis; the Kd of the synthetic full length 201 control was 3.8 nM while that of enzymatically synthecised 201 was 1.8 nM.

TABLE XIV

Specificities of Cloned, ssDNA Ligands*

| Ligand | SEQ ID NO: | LS-Rg | ES-Rg | PS-Rg |
|---|---|---|---|---|
| Family 1 | | | | |
| 111 | 149 | 1.1 nM | 1.2 µM | 840 nM |
| 201 | 142 | 110 nM | 37 nM | 1.0 µM |
| 204 | 129 | 450 pM | 1.5 µM | 2.9 µM |
| 227 | 134 | 64 pM | 33 nM | 560 nM |
| 230 | 132 | 44 pM | 19 nM | 600 nM |
| 233 | 146 | 120 pM | 39 nM | 420 nM |
| Family 2 | | | | |
| 181 | 157 | 200 pM | 37 nM | 1.6 µM |
| Family 4 | | | | |
| 122 | 159 | 340 pM | 400 nM | 420 nM |
| 174 | 158 | 46 pM | 28 nM | 380 nM |
| Family 5 | | | | |
| 127 | 162 | 250 pM | 1.3 µM | 780 nM |
| Family 6 | | | | |
| 196 | 163 | 220 pM | 50 nM | 3.4 µM |
| Family 7 | | | | |
| 206 | 165 | 120 pM | 100 nM | 600 nM |

*Kds were determined at room temperature. In assays with 700 nM CD22 β-Rg and 1.4 µM WGA less than 1% and 3% binding, respectively, was observed for all ligands suggesting that the dissociation constants are greater than 100 µM for these proteins.

We claim:

1. A method for identifying nucleic acid ligands and nucleic acid ligand sequences to a selectin comprising:
   a) contacting a candidate mixture of nucleic acids with a selectin, wherein nucleic acids having an increased affinity to said selectin relative to the candidate mixture may be partitioned from the remainder of the candidate mixture;
   b) partitioning the increased affinity nucleic acids from the remainder of the candidate mixture; and
   c) amplifying the increased affinity nucleic acids to yield a mixture of nucleic acids enriched for nucleic acid sequences with relatively higher affinity and specificity for binding to said selectin, whereby nucleic acid ligands of said selectin may be identified.

2. The method of claim 1 further comprising:
   d) repeating steps a), b) and c).

3. The method of claim 1 wherein said candidate mixture is comprised of single-stranded nucleic acids.

4. The method of claim 3 wherein said single-stranded nucleic acids are ribonucleic acids.

5. The method of claim 4 wherein said nucleic acids comprise modified ribonucleic acids.

6. The method of claim 5 wherein said nucleic acids comprise 2'-amino (2'NH$_2$) modified nucleic acids.

7. The method of claim 3 wherein said single-stranded nucleic acids are deoxyribonucleic acids.

8. The method of claim 1 wherein said selectin is selected from the group consisting of L-selectin, E-selectin, and P-selectin.

9. The method of claim 6 wherein said selectin is L-selectin.

* * * * *

UNITED STATES PATENT AND TRADEMARK OFFICE
CERTIFICATE OF CORRECTION

Page 1 of 3

PATENT NO. : 5,766,853
DATED : June 16, 1998
INVENTOR(S) : David H. Parma, Brian James Hicke and Larry Gold It is certified that error appears in the above-identified patent and that said Letters Patent is hereby corrected as shown below:

On the title page, after the Assignee, please insert --[*] The term of this patent shall not extend beyond the expiration date of Pat. No. 5,780,228.--.

At column 1, line 13, please delete "Methods of Producing."
At column 1, line 14, after "Ligands" please insert --to HIV-RT and HIV-1 Rev--.
At column 1, line 33, please delete "susceptability" and insert --susceptibility--.
At column 2, line 30, please delete "selecting" and insert --selectins--.
At column 2, line 31, please delete "recognise" and insert --recognize--.
At column 2, line 48 please delete "effacacious" and insert --efficacious--.
At column 3, line 20, please delete "recognise" and insert --recognize--.
At column 3, line 26, please delete "prerequiste" and insert --prerequisite--.
At column 3, line 35, please delete "Stretococcus" and insert --Streptococcus--.
At column 3, line 61, please delete "erthrocytes" and insert --erythrocytes--.
At column 3, line 63, please delete "theraputics for dysentary" and insert --therapeutics for dysentery--.
At column 4, line 12, please delete "oriental" and insert --Oriental--.
At column 4, line 12, please delete "caucasian" and insert --Caucasian--.
At column 4, line 15, please delete "arthritus" and insert --arthritis--.
At column 4, line 53, please delete "116" and insert --3116--.
At column 5, line 15, please delete "N-acetylglcosamine" and insert --N-acetylglucosamine--.
At column 5, line 19, please delete "theraputics" and insert --therapeutics--.
At column 5, line 33, please delete "the the" and insert --the--.
At column 5, line 42, please delete "75500" and insert --7550--.
At column 6, line 6, please delete "specifity" and insert --specificity--.
At column 6, line 17, before "Nucleic" please insert --Methods of Identifying--.
At column 6, line 48, please delete "Methods of Producing".
At column 6, line 48 after "Ligands" please insert --to HIV-RT and HIV-1 Rev--.

UNITED STATES PATENT AND TRADEMARK OFFICE
CERTIFICATE OF CORRECTION

Page 2 of 3

PATENT NO. : 5,766,853
DATED : June 16, 1998
INVENTOR(S) : David H. Parma, Brian James Hicke and Larry Gold It is certified that error appears in the above-identified patent and that said Letters Patent is hereby corrected as shown below:

At column 7, lines 22-24, please delete "2' Modified Pyrimidine" and insert --Known and Novel 2'-Modified Nucleosides--.

At column 7, line 31, after "SELEX" please insert --, now United States Patent No. 5,637,459--.

At column 7, line 34, after "SELEX",", please insert --now United States Patent No. 5,683,867--.

At column 9, line 31, please delete "occurances" and insert --occurrences--.
At column 9, line 44, after "entitled" please insert --Methods for Identifying--.
At column 11, line 66, please delete "September 9" and insert --September 8--.
At column 12, line 51, please delete "repefusion" and insert --reperfusion--.
At column 15, line 50, please delete "stiochiometry" and insert --stoichiometry--.
At column 15, line 51, please delete "stiochiometry" and insert --stoichiometry--.
At column 17, line 4, please delete "nonrandomess" and insert --non-randomness--.
At column 17, line 5, please delete "progess" and insert --progress--.
At column 17, line 25, please delete "forllowing" and insert --following--.
At column 17, lines 29-30, please delete "disappearnce" and insert --disappearance--.
At column 17, line 33, please delete "familes" and insert --families--.
At column 17, line 34, please delete "constrast" and insert --contrast--.
At column 18, line 19, please delete "affinty" and insert --affinity--.
At column 18, line 24, please delete "serveral" and insert --several--.
At column 18, line 31, please delete "improvent" and insert --improvement--.
At column 18, line 51, please delete "specificty" and insert --specificity--.
At column 18, lines 60-61, please delete "competively" and insert --competitively--.
At column 19, line 8, please delete "possiblity" and insert --possibility--.
At column 19, line 31, please delete "varifies" and insert --verifies--.
At column 19, lines 45-46, please delete "erthrocytes" and insert --erythrocytes--.
At column 20, line 36, please delete "anitbodies" and insert --antibodies--.

UNITED STATES PATENT AND TRADEMARK OFFICE
CERTIFICATE OF CORRECTION

PATENT NO. : 5,766,853
DATED : June 16, 1998
INVENTOR(S) : David H. Parma, Brian James Hicke and Larry Gold It is certified that error appears in the above-identified patent and that said Letters Patent is hereby corrected as shown below:

At column 21, line 33, please delete "obervations" and insert --observations--.
At column 23, line 18, please delete "polyproylene" and insert --polypropylene--.
At column 23, line 42, please delete "scintilation" and insert --scintillation--.
At column 23, line 56, please delete "competive" and insert --competitive--.
At column 24, line 41, please delete "non-randomess" and insert --non-randomness--.
At column 24, line 47, please delete "repectively" and insert --respectively--.
At column 24, line 55, please delete "occuring" and insert --occurring--.
At column 25, line 53, please delete "serveral" and insert --several--.
At column 26, line 28, please delete "feasibilty" and insert --feasibility--.
At column 26, line 34, please delete "Sialy" and insert --Sialyl--.
At column 27, line 60, please delete "biotintylation" and insert --biotinylation--.
At column 28, line 62, please delete "mannually" and insert --manually--.
At column 28, line 63, please delete "Nexstar" and insert --NeXstar--.
At column 28, line 64, please delete "occuring" and insert --occurring--.
At column 29, line 23, please delete "respresented" and insert --represented--.
At column 30, line 24, please delete "feasibilty" and insert --feasibility--.
At column 30, line 43, please delete "concensus" and insert --consensus--.
At column 30, line 45, please delete "occurances" and insert --occurrences--.

Signed and Sealed this

Nineteenth Day of January, 1999

Attest:

Attesting Officer

*Acting Commissioner of Patents and Trademarks*